US012673039B2

(12) United States Patent
Lithgow et al.

(10) Patent No.: US 12,673,039 B2
(45) Date of Patent: Jul. 7, 2026

(54) METHODS OF INDUCING AUTOPHAGY USING COUMARIN DERIVATIVES AND RELATED COMPOUNDS

(71) Applicant: Buck Institute for Research on Aging, Novato, CA (US)

(72) Inventors: Gordon J. Lithgow, Novato, CA (US); Julie K. Andersen, Novato, CA (US); Shankar J. Chinta, Novato, CA (US); Manish Chamoli, San Mateo, CA (US)

(73) Assignee: Buck Institute for Research on Aging, Novato, CA (US)

( * ) Notice: Subject to any disclaimer, the term of this patent is extended or adjusted under 35 U.S.C. 154(b) by 1276 days.

(21) Appl. No.: 17/428,600

(22) PCT Filed: Feb. 5, 2020

(86) PCT No.: PCT/US2020/016857

§ 371 (c)(1),
(2) Date: Aug. 4, 2021

(87) PCT Pub. No.: WO2020/163510

PCT Pub. Date: Aug. 13, 2020

(65) Prior Publication Data

US 2022/0265605 A1 Aug. 25, 2022

Related U.S. Application Data

(60) Provisional application No. 62/802,146, filed on Feb. 6, 2019.

(51) Int. Cl.

| | |
|---|---|
| ***A61K 31/37*** | (2006.01) |
| ***A61K 31/4745*** | (2006.01) |
| ***A61K 31/5377*** | (2006.01) |
| ***A61P 25/28*** | (2006.01) |

(52) U.S. Cl.

CPC .......... *A61K 31/37* (2013.01); *A61K 31/4745* (2013.01); *A61K 31/5377* (2013.01); *A61P 25/28* (2018.01)

(58) Field of Classification Search

CPC ............................ A61K 31/37; A61K 31/4745
See application file for complete search history.

(56) References Cited

PUBLICATIONS

Fallarero A., et al., "Inhibition of Acetylcholinesterase by Coumarins: The Case of Coumarin 106," Pharmacological Research, Sep.-Oct. 2008, vol. 58, pp. 215-221. (Year: 2008).*
Uddin, Autophagy and Alzheimer's Disease: From Molecular Mechanisms to Therapeutic Implications, 2018, Frontiers in Aging Neuroscience, vol. 10, No. 4, p. 1-18 (Year: 2018).*
Fallarero A., et al., "Inhibition of Acetylcholinesterase by Coumarins: The Case of Coumarin 106," Pharmacological Research, Sep.-Oct. 2008, vol. 58, pp. 215-221.
International Preliminary Report on Patentability dated Aug. 10, 2021 in PCT Application No. PCT/US2020/016857.
International Search Report and Written Opinion dated May 20, 2020 in PCT/US2020/016857.
Siddiqui A., et al., "Mitochondrial Quality Control via the PGC1 α-TFEB Signaling Pathway Is Compromised by Parkin Q311X Mutation But Independently Restored by Rapamycin," The Journal of Neuroscience, Sep. 16, 2015, vol. 35(37), doi: 10.1523/JNEUROSCI.0109-15.2015, pp. 12833-12844.
Yusufzai et al., "Molecular Docking Studies of Coumarin Hybrids as Potential Acetylcholinesterase, Butyrylcholinesterase, Monoamine Oxidase A/B and [beta]-Amyloid Inhibitors for Alzheimer's Disease," Chemistry Central Journal, Dec. 4, 2018, vol. 12(128), pp. 1-58.
Zhang E., et al., "Glycycoumarin Inhibits Hepatocyte Lipoapoptosis Through Activation of Autophagy and Inhibition of ER Stress/GSK-3-Mediated Mitochondrial Pathway" Sci Rep, Nov. 30, 2016; vol. 6, pp. 1-12.
Ullah, R. et al. (2021). "Abnormal amyloid beta metabolism in systemic abnormalities and Alzheimer's pathology: Insights and therapeutic approaches from periphery," *Ageing Res Rev* 71:101451.
Xu, H. et al. (2017). "Highly Enantioselective Catalytic Vinylogous Propargylation of Coumarins Yields a Class of Autophagy Inhibitors," *Angew Chem Int Ed* 56(37):11232-11236.

* cited by examiner

*Primary Examiner* — Adam C Milligan
*Assistant Examiner* — Kareen Cheng
(74) *Attorney, Agent, or Firm* — Mintz, Levin, Cohn, Ferris, Glovsky and Popeo, P.C.

(57) ABSTRACT

In various embodiments compounds that induce and/or promote autophagy are provided as wells as methods of use thereof (e.g., in the prophylaxis or treatment of chronic pathologies associated with aging). In one illustrative, but non-limiting embodiments the compound(s) comprise, inter alia, coumarin 106.

2 Claims, 56 Drawing Sheets

Specification includes a Sequence Listing.

C1 (coumarin 106)
(AIC106)

H4

D2

C3

E6

E2

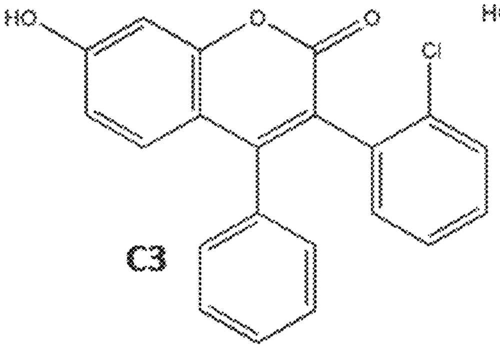
C3
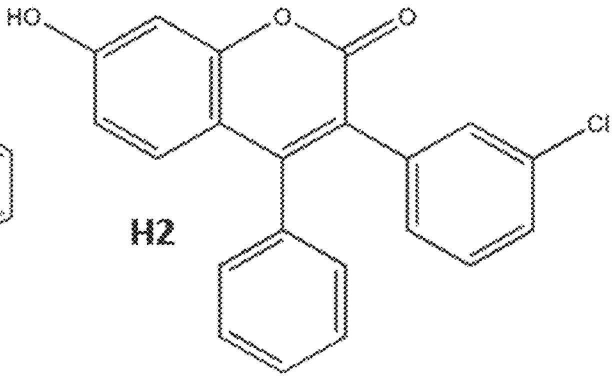
H2
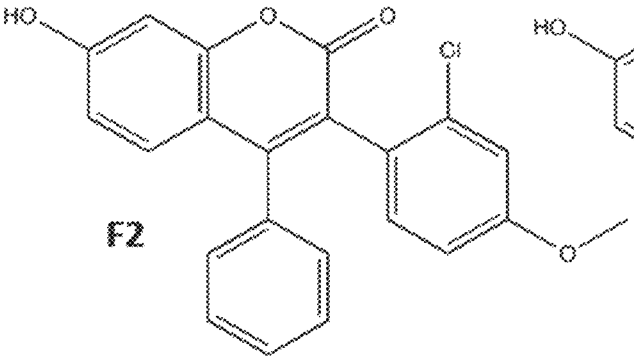
F2
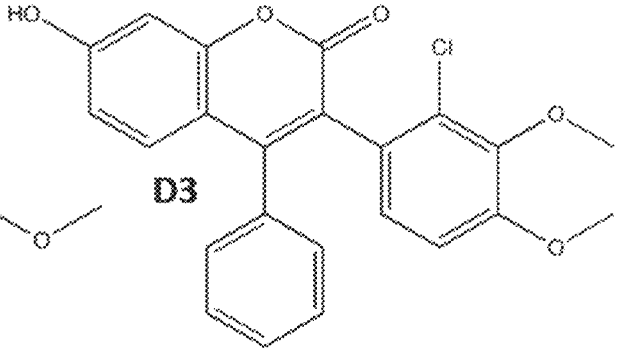
D3
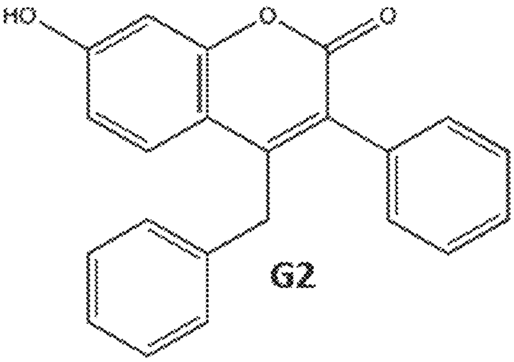
G2
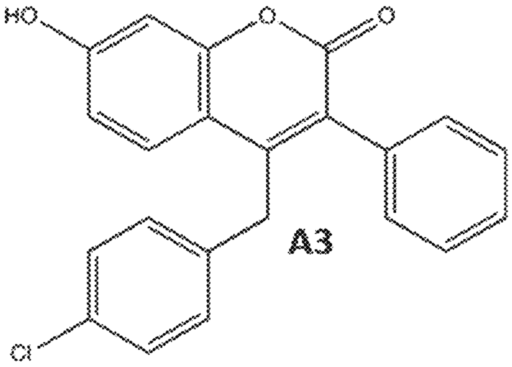
A3
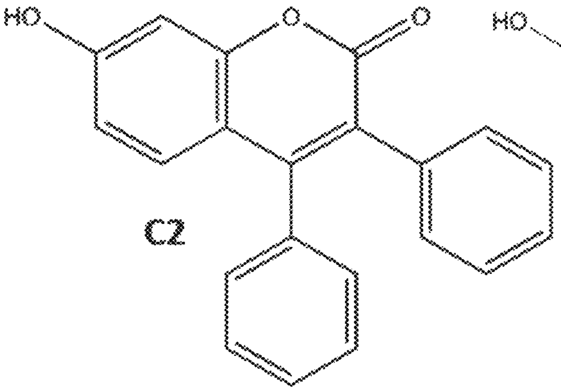
C2
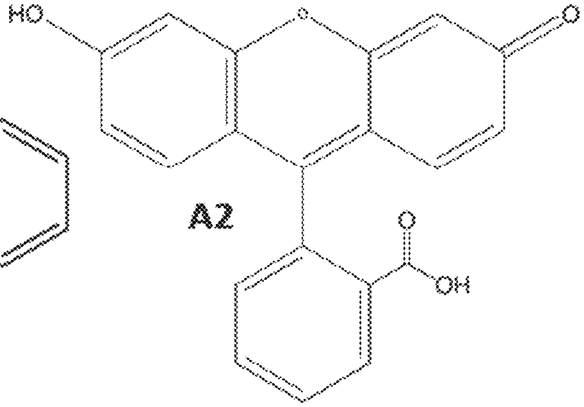
A2
*FIG. 1, cont'd.*

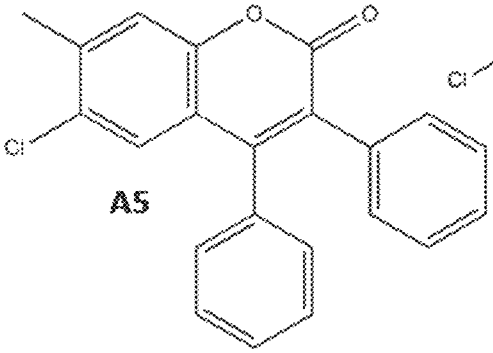
A5
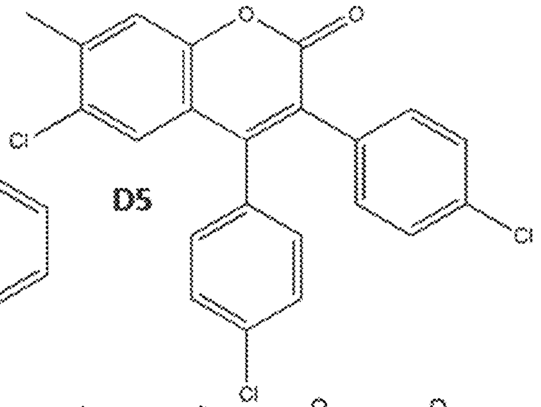
D5
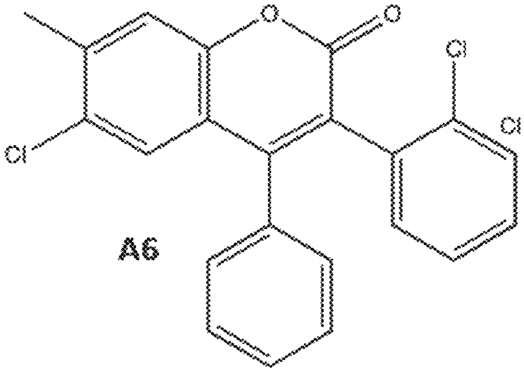
A6
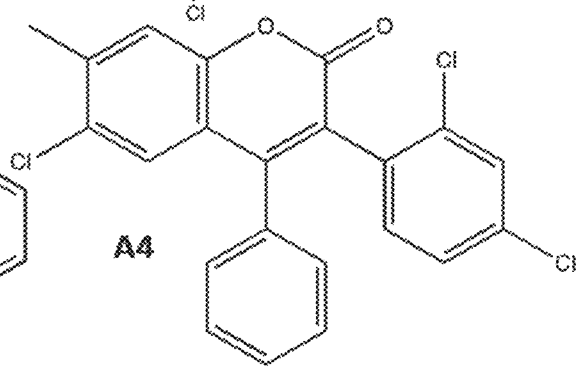
A4
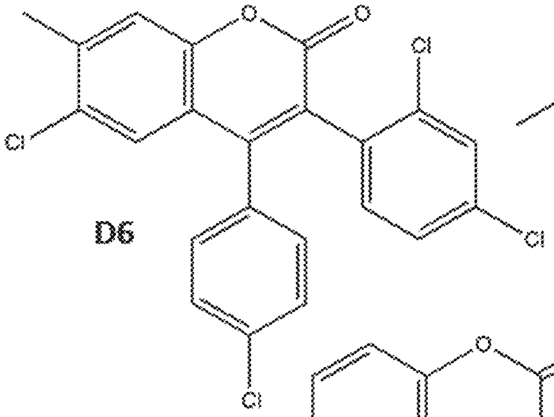
D6
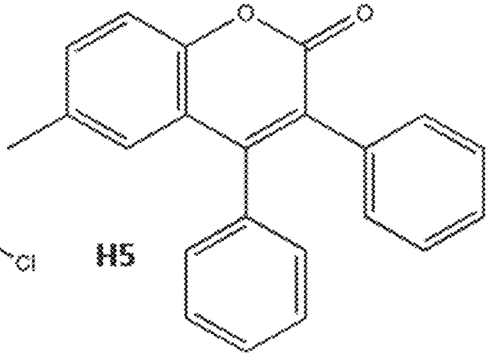
H5
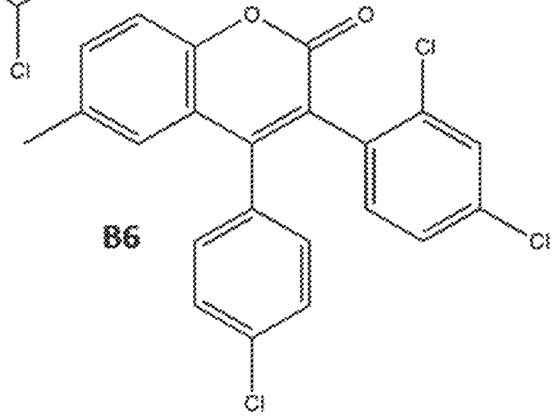
B6
FIG. 1, cont'd.

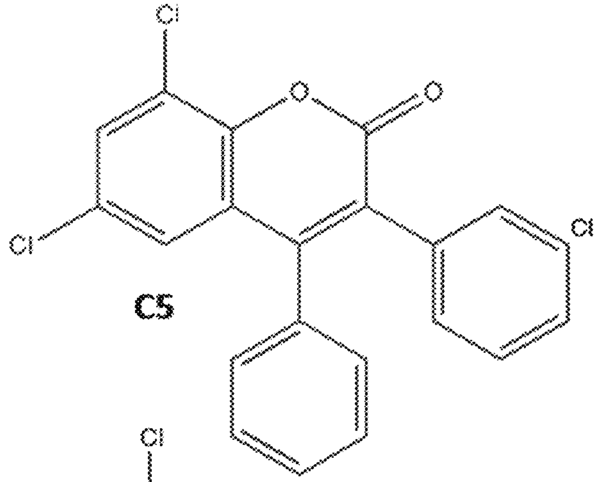
C5
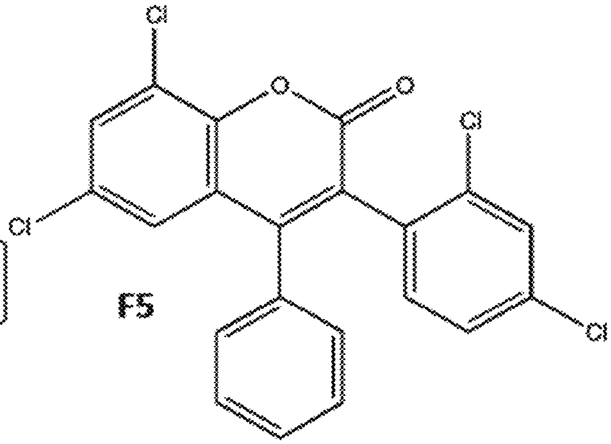
F5
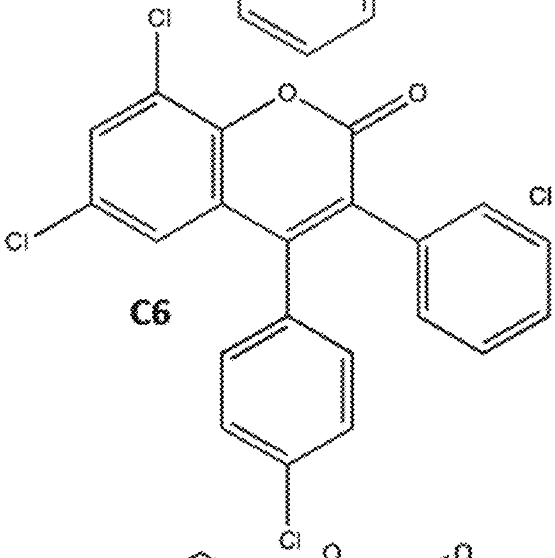
C6
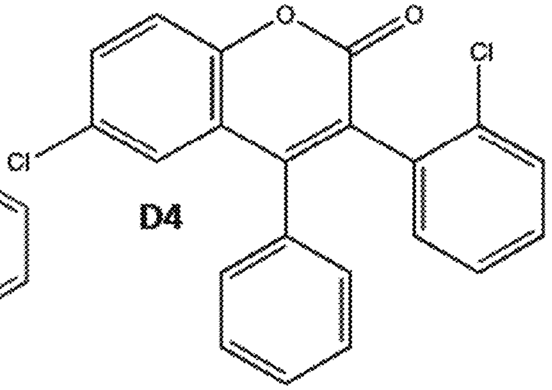
D4
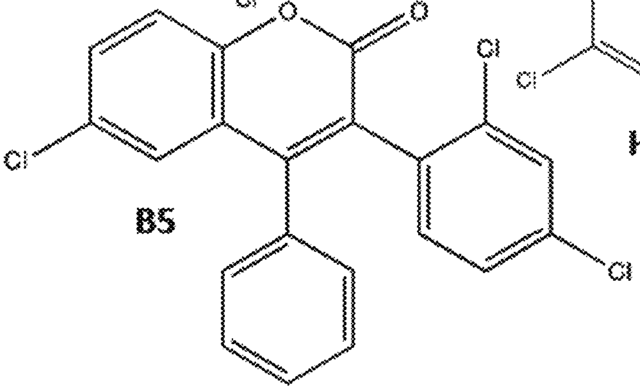
B5
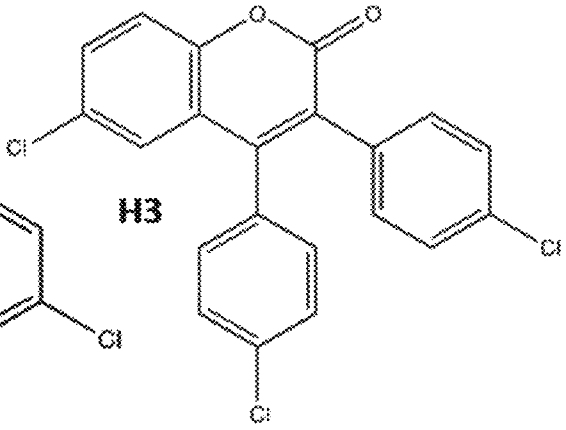
H3
*FIG. 1, cont'd.*

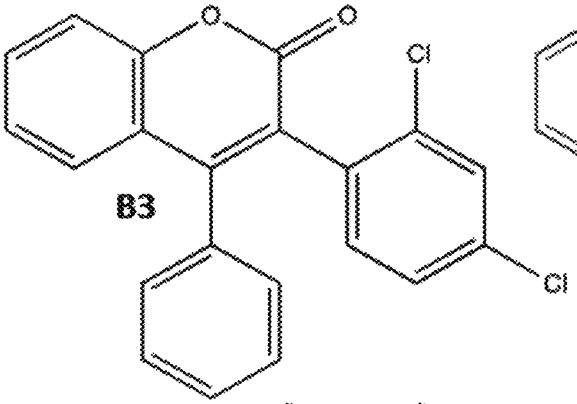
B3
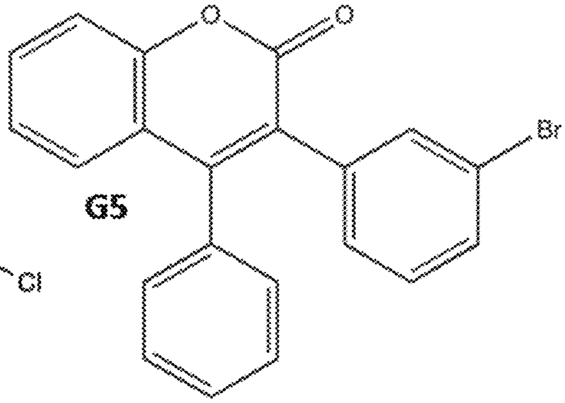
G5
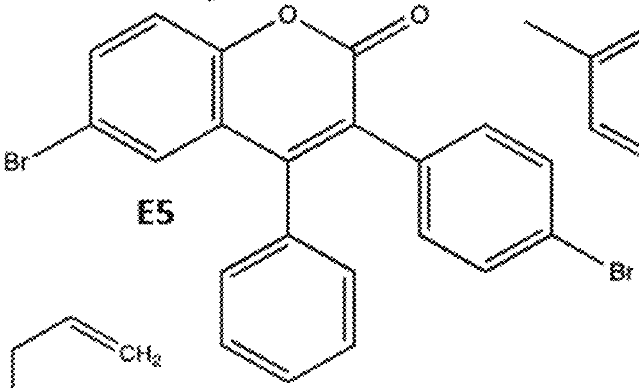
E5
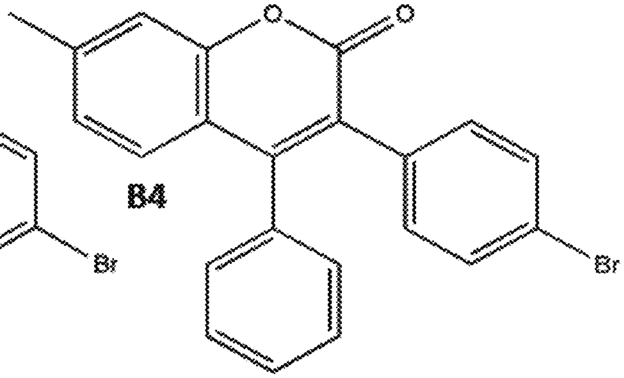
B4
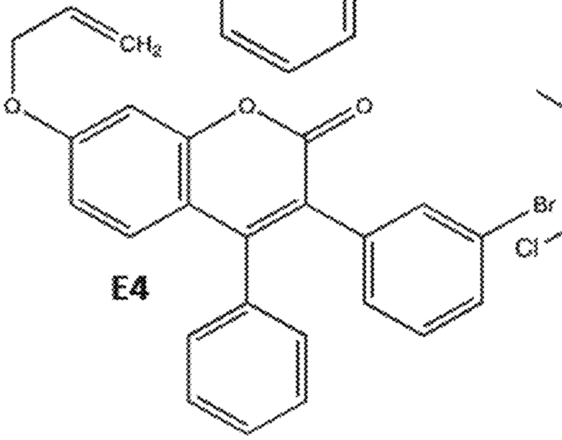
E4
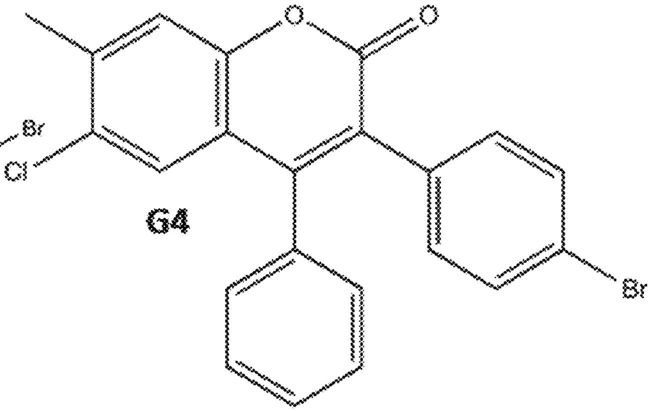
G4
FIG. 1, cont'd.

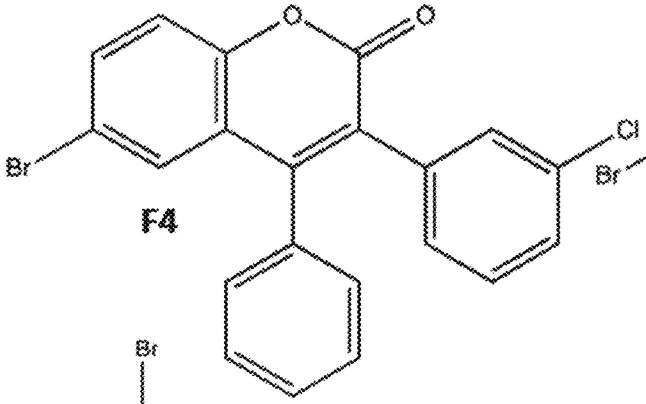
F4
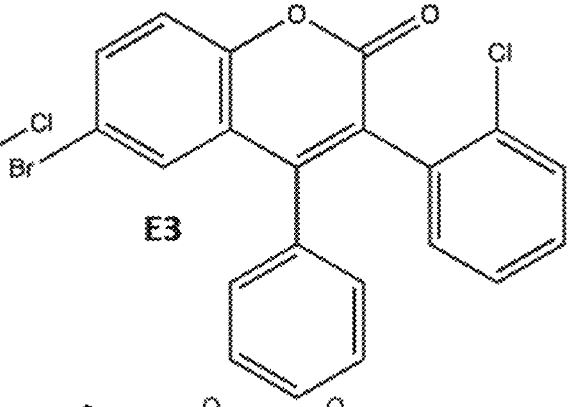
E3
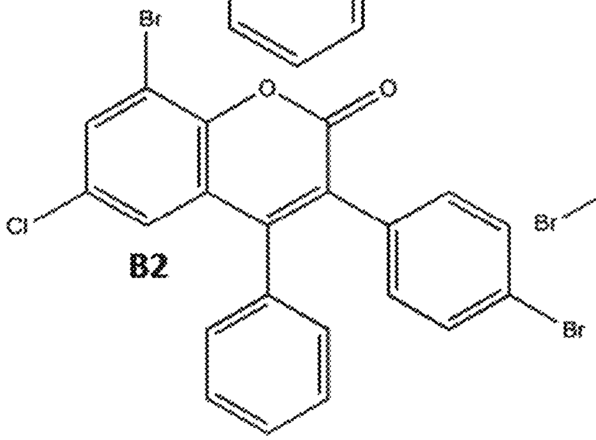
B2
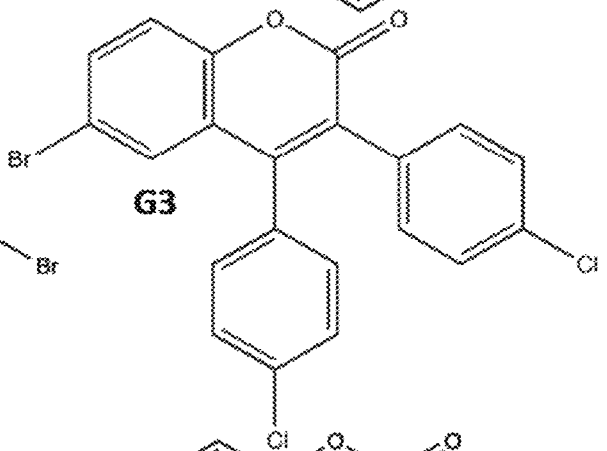
G3
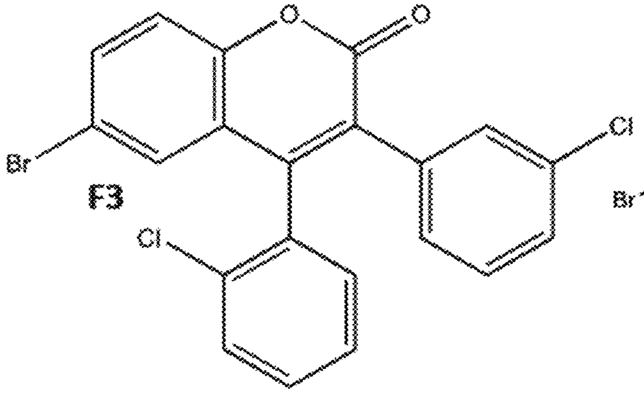
F3
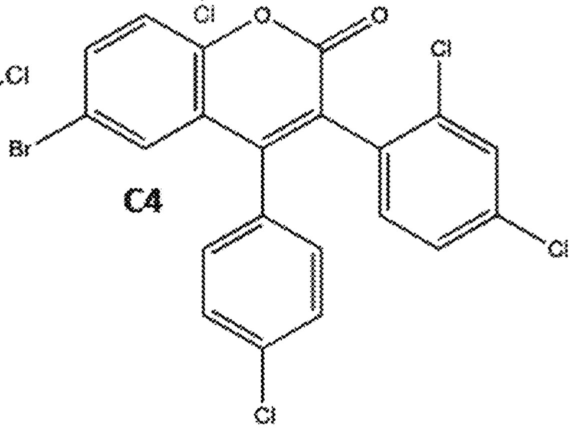
C4
FIG. 1, cont'd.

DAF-12/FXR inhibition impacts mitochondrial health: Mitobiogenesis

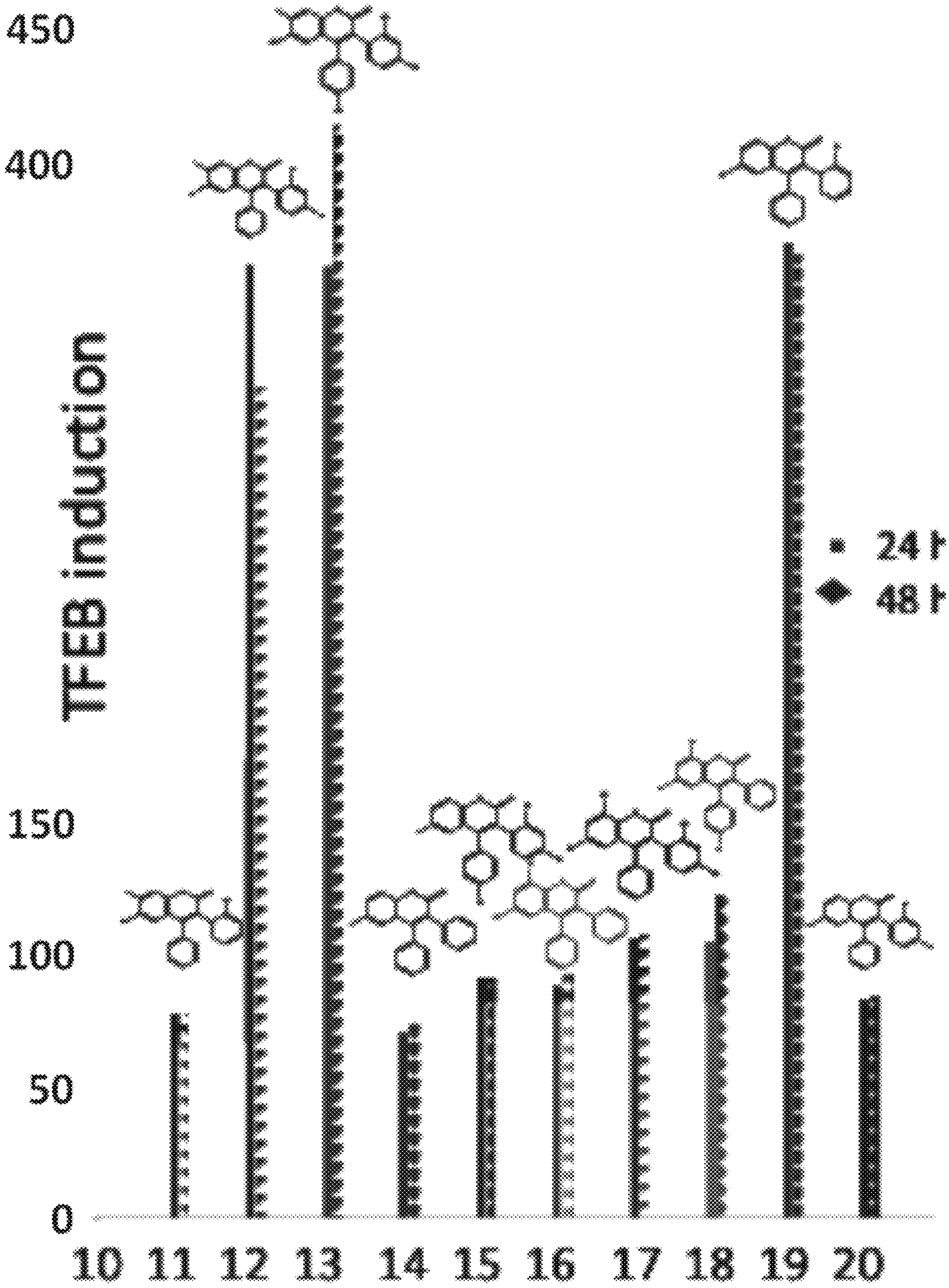
*FIG. 17, cont'd.*

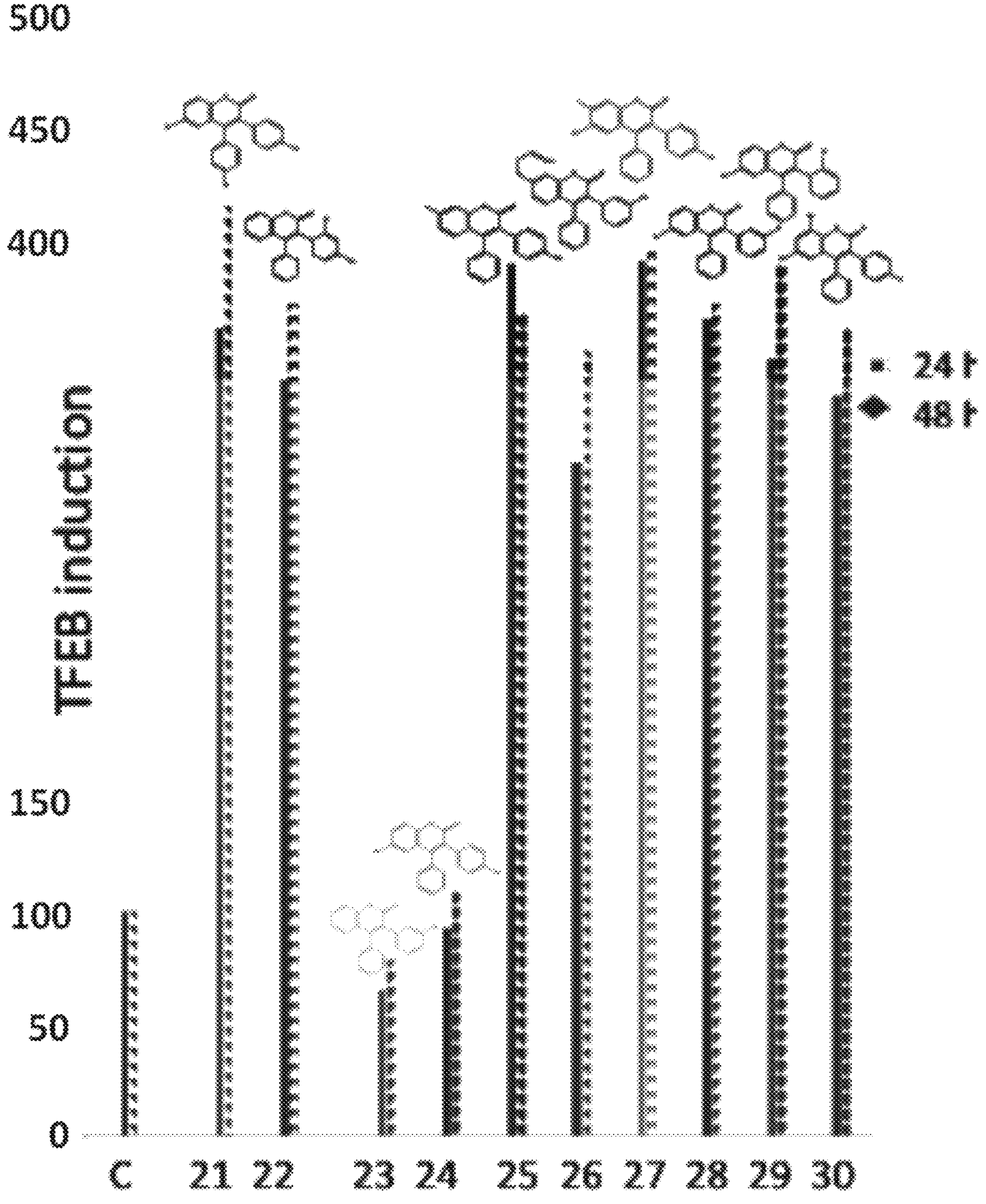
FIG. 17, cont'd.

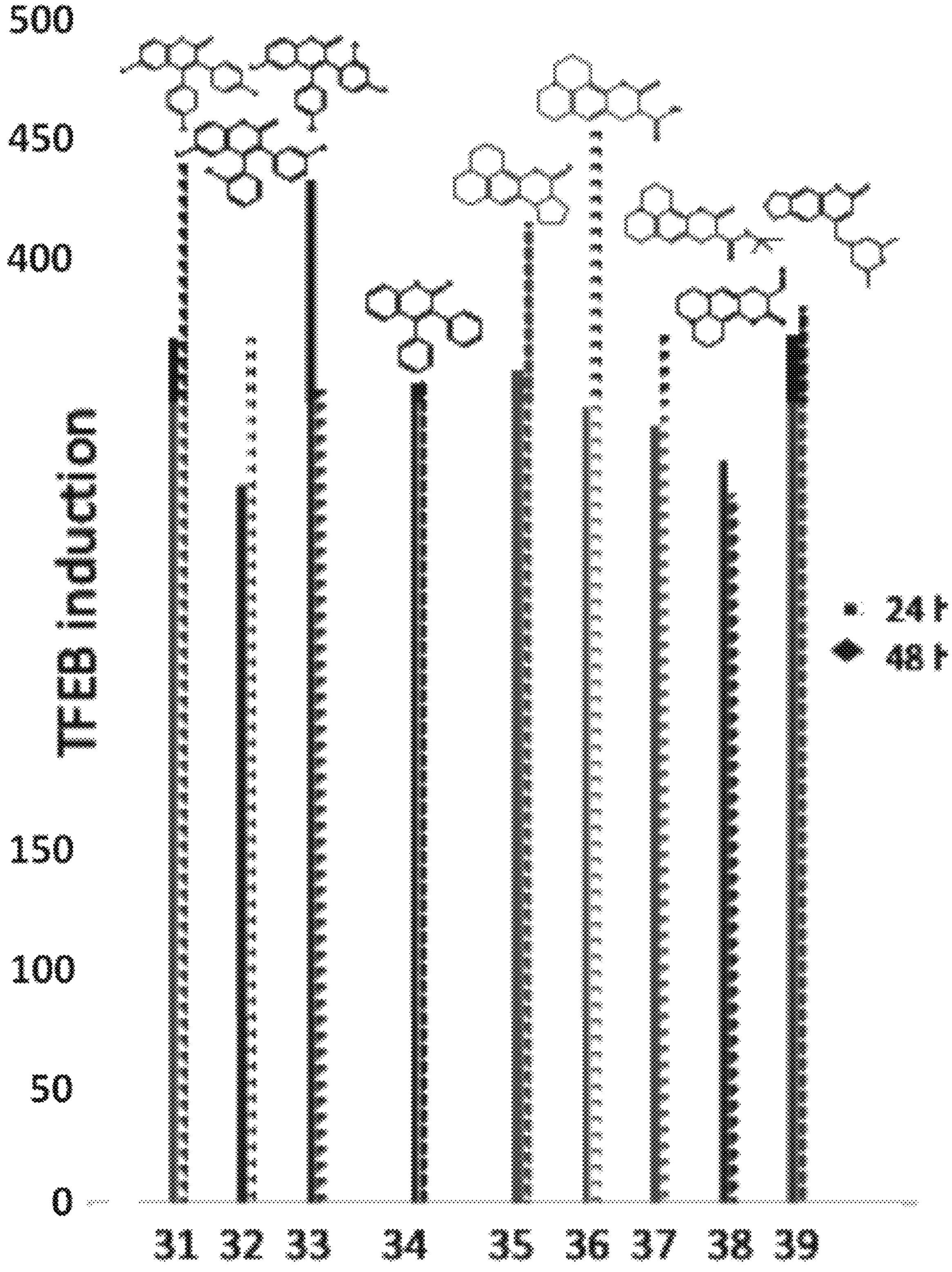
*FIG. 17, cont'd.*

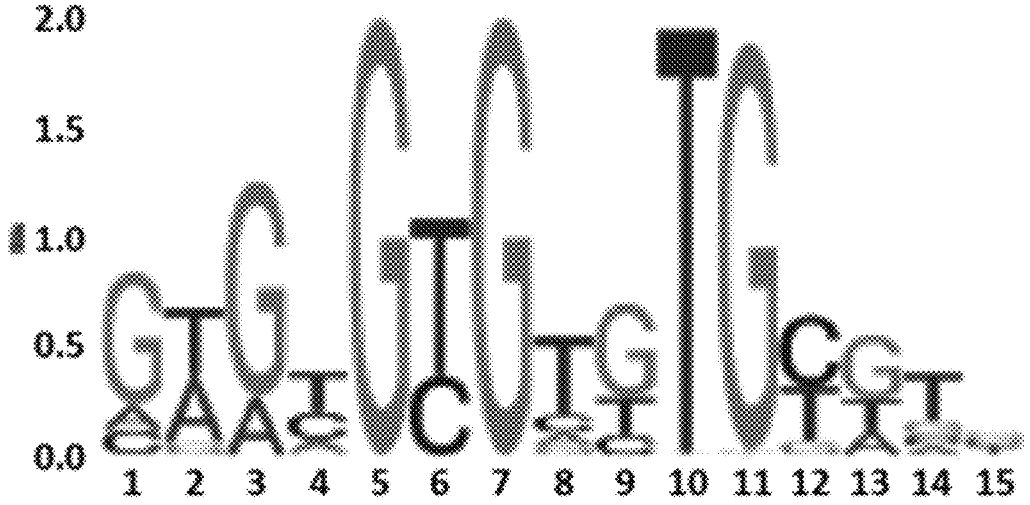

| | Matrix ID | Name | Score | Relative Score | Seq. ID | Start/End | Strand | Predicted Sequence |
|---|---|---|---|---|---|---|---|---|
| 1 | MAO538.1 | daf-12 | 11.19 | 0.87 | HLH-30 Pr | 589/603 | - | gagtgtgtatgcgaa |
| 2 | MAO538.1 | daf-12 | 8.71 | 0.83 | HLH-30 Pr | 593/6078 | - | atacgagtgtgtatg |
| 3 | MAO538.1 | daf-12 | 7.29 | 0.81 | HLH-30 Pr | 983/997 | + | gtctgtgtctccgtg |
| 4 | MAO538.1 | daf-12 | 7.20 | 0.81 | HLH-30 Pr | 1171/1185 | - | gtgtgtgtatgatgt |
| 5 | MAO538.1 | daf-12 | 8.97 | 0.83 | HLH-30 Pr | 1173/1187 | - | ctgtgtgtgtatgat |
| 6 | MAO538.1 | daf-12 | 8.17 | 0.82 | HLH-30 Pr | 1175/1189 | - | ttctgtgtgtgtatg |
| 7 | MAO538.1 | daf-12 | 10.48 | 0.86 | HLH-30 Pr | 1186/1200 | - | gtgtgtgtgtattct |
| 8 | MAO538.1 | daf-12 | 17.87 | 0.97 | HLH-30 Pr | 1188/1202 | - | gtgtgtgtgtgtatt |
| 9 | MAO538.1 | daf-12 | 18.08 | 0.97 | HLH-30 Pr | 1190/1204 | - | gtgtgtgtgtgtgta |
| 10 | MAO538.1 | daf-12 | 17.42 | 0.96 | HLH-30 Pr | 1192/1206 | - | atgtgttgtgtgtgtg |
| 11 | MAO538.1 | daf-12 | 15.50 | 0.93 | HLH-30 Pr | 1194/1208 | - | ctatgtgtgtgtgtg |
| 12 | MAO538.1 | daf-12 | 8.63 | 0.84 | HLH-30 Pr | 1196/1210 | - | gtctatgtgtgtgtg |

SH-SY5Y neuronal cells

FIG. 29A

| Genes | No of binding sites | CHIP Enrichment |
|---|---|---|
| Vacuolar H ATPase(vha-19) | 3 | 9.6307 |
| Protein lgg(lgg-2) | 4 | 9.17402 |
| Ectopic P Granules(epg-9) | 9 | 9.01744 |
| NIP3 homolog(dct-1) | 3 | 8.19413 |
| related to yeast Vacuolar Protein Sorting factor(vps-32.1) | 3 | 8.07398 |
| UBiQuitin(ubq-1) | 3 | 7.69851 |
| Beclin homolog(bec-1) | 6 | 7.32092 |
| Ectopic P Granules(epg-7) | 3 | 7 |
| CaThepSin A homolog(ctsa-1) | 3 | 6.60062 |
| AuTophaGy (yeast Atg homolog)(atg-9) | 4 | 6.15112 |
| UBiQuiLin(ubql-1) | 3 | 5.77579 |
| Probable V-type proton ATPase 116 kDa subunit a(unc-32) | 3 | 5.49849 |
| Helix Loop Helix(hlh-30) | 12 | 5.38675 |
| related to yeast Vacuolar Protein Sorting factor(vps-4) | 3 | 5.1374 |
| V-type proton ATPase catalytic subunit A(vha-13) | 5 | 5.12051 |
| CREB Homolog(crh-2) | 3 | 5.11895 |
| LAMP family protein lmp-1(lmp-1) | 3 | 5.08712 |
| Vacuolar H ATPase(vha-8) | 3 | 4.91889 |
| TRansport Protein Particle(trpp-8) | 8 | 4.76887 |
| AuTophaGy (yeast Atg homolog)(atg-2) | 5 | 4.6761 |
| Probable V-type proton ATPase subunit B(vha-12) | 3 | 4.37955 |
| Probable V-type proton ATPase subunit G(vha-10) | 5 | 4.37011 |
| AuTophaGy (yeast Atg homolog)(atg-18) | 3 | 4.21353 |
| Calpain clp-1(clp-1) | 3 | 4.21149 |
| V-type proton ATPase 16 kDa proteolipid subunit 1(vha-1) | 3 | 4.14303 |
| V-type proton ATPase 16 kDa proteolipid subunit 2/3(vha-2) | 3 | 4.14303 |
| ATP synthase subunit(atp-3) | 3 | 4.12165 |
| Vacuolar H ATPase(vha-16) | 3 | 4.07111 |
| Cation-transporting ATPase(catp-5) | 3 | 3.83834 |
| Sodium/potassium-transporting ATPase subunit alpha(catp-4) | 3 | 3.45932 |
| S. cerevisiae FIS1-related(fis-2) | 3 | 3.20721 |

SEQUENCE LISTING

```
<160> NUMBER OF SEQ ID NOS: 13

<210> SEQ ID NO 1
<211> LENGTH: 15
<212> TYPE: DNA
<213> ORGANISM: Caenorhabditis elegans

<400> SEQUENCE: 1

gagtgtgtat gcgaa                                                    15
```

-continued

<210> SEQ ID NO 2
<211> LENGTH: 15
<212> TYPE: DNA
<213> ORGANISM: Caenorhabditis elegans

<400> SEQUENCE: 2
atacgagtgt gtatg 15

<210> SEQ ID NO 3
<211> LENGTH: 15
<212> TYPE: DNA
<213> ORGANISM: Caenorhabditis elegans

<400> SEQUENCE: 3
gtctgtgtct ccgtg 15

<210> SEQ ID NO 4
<211> LENGTH: 15
<212> TYPE: DNA
<213> ORGANISM: Caenorhabditis elegans

<400> SEQUENCE: 4
gtgtgtgtat gatgt 15

<210> SEQ ID NO 5
<211> LENGTH: 15
<212> TYPE: DNA
<213> ORGANISM: Caenorhabditis elegans

<400> SEQUENCE: 5
ctgtgtgtgt atgat 15

<210> SEQ ID NO 6
<211> LENGTH: 15
<212> TYPE: DNA
<213> ORGANISM: Caenorhabditis elegans

<400> SEQUENCE: 6
ttctgtgtgt gtatg 15

<210> SEQ ID NO 7
<211> LENGTH: 15
<212> TYPE: DNA
<213> ORGANISM: Caenorhabditis elegans

<400> SEQUENCE: 7
gtgtgtgtgt attct 15

<210> SEQ ID NO 8
<211> LENGTH: 15
<212> TYPE: DNA
<213> ORGANISM: Caenorhabditis elegans

<400> SEQUENCE: 8
gtgtgtgtgt gtatt 15

<210> SEQ ID NO 9
<211> LENGTH: 15
<212> TYPE: DNA
<213> ORGANISM: Caenorhabditis elegans

<400> SEQUENCE: 9
gtgtgtgtgt gtgta 15

-continued

<210> SEQ ID NO 10
<211> LENGTH: 16
<212> TYPE: DNA
<213> ORGANISM: Caenorhabditis elegans

<400> SEQUENCE: 10
atgtgttgtg tgtgtg 16

<210> SEQ ID NO 11
<211> LENGTH: 15
<212> TYPE: DNA
<213> ORGANISM: Caenorhabditis elegans

<400> SEQUENCE: 11
ctatgtgtgt gtgtg 15

<210> SEQ ID NO 12
<211> LENGTH: 15
<212> TYPE: DNA
<213> ORGANISM: Caenorhabditis elegans

<400> SEQUENCE: 12
gtctatgtgt gtgtg 15

<210> SEQ ID NO 13
<211> LENGTH: 20
<212> TYPE: DNA
<213> ORGANISM: Artificial
<220> FEATURE:
<223> OTHER INFORMATION: CRISPR guide sequence

<400> SEQUENCE: 13
ggcccaacaa gcaaatgtcg 20

METHODS OF INDUCING AUTOPHAGY USING COUMARIN DERIVATIVES AND RELATED COMPOUNDS

CROSS-REFERENCE TO RELATED APPLICATIONS

This application is a U.S. 371 National Phase of PCT/US2020/016857, filed on Feb. 5, 2020, which claims benefit of and priority to U.S. Ser. No. 62/802,146, filed on Feb. 6, 2019, both of which is incorporated herein by reference in their entirety for all purposes.

STATEMENT OF GOVERNMENTAL SUPPORT

[Not Applicable]

INCORPORATION BY REFERENCE OF SEQUENCE LISTING PROVIDED AS A TEXT FILE

This application contains references to nucleic acid sequences that have been submitted concurrently herewith as the sequence listing text file "BUCK-P058US_ST25.txt", file size 2,608 bytes, created on May 8, 2022, which is incorporated by reference in its entirety pursuant to 37 C.F.R. § 1.52(e)(5).

BACKGROUND

Autophagy encompasses the different routes that cells use to deliver cytoplasmic substrates to lysosomes for degradation. These include macroautophagy, chaperone-mediated autophagy, and microautophagy. In particular, macroautophagy (referred to herein as autophagy), is a process of cellular self-cannibalism in which portions of the cytoplasm are sequestered within double- or multimembraned vesicles (autophagosomes) and then delivered to lysosomes for bulk degradation. The initial phases of macroautophagy consist of the formation of a phagophore (also called isolation membrane), the engulfment of cytoplasmic material by the phagophore, the elongation of the phagophore membrane, and fusion of its edges to close the autophagosome. The outer membrane of the autophagosome fuses with the lysosome to form the autolysosome (also called autophagolysosome) in which the luminal material including the internal membrane is degraded. The resulting breakdown products are released through permeases and are recycled in the cytosol (Ravikumar et al. (2005) *Nat. Genet.,* 37: 771-776). Thus, autophagy is the mechanism through which the non-nuclear (cytoplasmic) parts of the cell can be renewed and through which cytoplasmic macromolecules can be mobilized to generate energy-rich compounds that can meet the bioenergetic demand of the cell in conditions of dwindling external or internal resources.

Autophagy is a predominantly cytoprotective (rather than a self-destructive) process (see, e.g., Kroemer & Levine (2008) *Nat. Rev. Mol. Cell Biol.,* 9: 004-1010). Autophagy has been observed to mediate protective effects in multiple rodent models of organ damage affecting the liver (see, e.g., Zang & Cuervo (2008) *Nat. Med.,* 14: 959-965), heart (see, e.g., Gottlieb & Mentzer (2010) *Annu. Rev. Physiol.,* 72: 45-59), nervous system (see, e.g., Ravikumar et al. (2005) *Nat. Genet.,* 37: 771-776), and kidney (see, e.g., Jiang et al. (2010) *Am. J. Pathol.,* 176: 1181-1192), just to mention a few examples.

Beyond its function in the adaptation of individual cells or organs to changing conditions, autophagy has a prominent role in determining the life span of many organisms. Reduced autophagy has been associated with accelerated aging, whereas stimulation of autophagy might have potent anti-aging effects (see, e.g., Madeo et al. (2010) *Nat. Cell Biol.,* 12: 842-846).

Ageing is typically characterized, inter alia, by the increasing occurrence of chronic disease. Such chronic diseases include but are not limited to Alzheimer's disease, dementia and mild cognitive impairment (MCI), Parkinson's disease, chronic obstructive pulmonary disease (COPD), depression, heart failure, liver failure, chronic kidney disease (CKD), diabetes and metabolic syndrome, ischemic heart disease, arthritis, hypertension, and the like. These and other chronic diseases in late life are a massive economic and social burden. Between 2005 and 2030 the number of adults aged 65 and older in the United States is expected to increase from 37 million to over 70 million (Institute of Medicine. Retooling for an aging America: Building the health care workforce. Washington, D.C: National Academics Press, Inc.; 2008). An epidemic of chronic disease" confronts the American health care system (see, e.g., Anderson & Horvath (2004) Pub. Health Rep., 119: 263-270). Even now, chronic disease accounts for three-quarters of America's direct health expenditures (see, e.g., Center for Technology and Aging Technologies for Remote Patient Monitoring in Older Adults. Position Paper, Discussion Draft, December 2009; Nobel & Norman (2003) *Disease Management.* 6: 219-231), with eight out of ten older individuals challenged by one or more chronic diseases (Id.).

SUMMARY

Our long-term goal is to develop general therapeutic approaches that are effective against multiple disease states. We propose that transient activation of autophagy is one such strategy as this process removes intracellular damage associated with many chronic diseases. We have conducted chemical screens for autophagy inducers and identified compounds that are promising drug candidates.

Various embodiments contemplated herein may include, but need not be limited to, one or more of the following:

Embodiment 1: A method of promoting autophagy in cells, said method comprising:

contacting said cells with an effective amount of one or more compounds that promote autophagy, where said compounds are selected from the group consisting of 2,3,6,7,10,11-Hexahydro-1H,5H-cyclopenta(3,4)(1)benzopyrano(6,7,8-ij)quinolizin-12(9H)-one (Coumarin 106; CAS Registry No. 41175-45-5), C3, H2, F2, D3, G2, A3, C2, A2, A5, D5, A6, A4, D6, H5, B6, C5, F5, C6, D4, B5, H3, B3, G5, E5, B4, E4, G4, F4, E3, B2, G3, F3, C4, H4, D2, C3, E2, and E6, or a pharmaceutically acceptable salt thereof.

Embodiment 2: The method of embodiment 1, wherein the cells are in vivo in a mammal and the method comprises administering said compounds to said mammal.

Embodiment 3: A method for the treatment or prophylaxis of a disease or condition that responds favorably to the induction or promotion of autophagy a subject, said method comprising:

administering to said subject a therapeutically effective amount, or a prophylactically effective amount of one or more compounds that promote autophagy where said compounds comprise one or more compounds selected from the group consisting of 2,3,6,7,10,11-Hexahydro- 1H,5H-cyclopenta(3,4)(1)benzopyrano(6,7,8-ij)quinolizin-12(9H)-one (Coumarin 106; CAS Registry No. 41175-45-5), C3, H2, F2, D3, G2, A3, C2, A2, A5, D5, A6, A4, D6, H5, B6, C5, F5, C6, D4, B5, H3, B3, G5, E5, B4, E4, G4, F4, E3, B2, G3, F3, C4, H4, D2, C3, E2, and E6, or a pharmaceutically acceptable salt thereof.

Embodiment 4: The method according to any one of embodiments 1-3, wherein said one or more compounds comprise compound C1, or a pharmaceutically acceptable salt thereof.

Embodiment 5: The method according to any one of embodiments 1-4, wherein said one or more compounds comprise compound C3, or a pharmaceutically acceptable salt thereof.

Embodiment 6: The method according to any one of embodiments 1-5, wherein said one or more compounds comprise compound H2, or a pharmaceutically acceptable salt thereof.

Embodiment 7: The method according to any one of embodiments 1-6, wherein said one or more compounds comprise compound F2, or a pharmaceutically acceptable salt thereof.

Embodiment 8: The method according to any one of embodiments 1-7, wherein said one or more compounds comprise compound D3, or a pharmaceutically acceptable salt thereof.

Embodiment 9: The method according to any one of embodiments 1-8, wherein said one or more compounds comprise compound G2, or a pharmaceutically acceptable salt thereof.

Embodiment 10: The method according to any one of embodiments 1-9, wherein said one or more compounds comprise compound A3, or a pharmaceutically acceptable salt thereof.

Embodiment 11: The method according to any one of embodiments 1-10, wherein said one or more compounds comprise compound C2, or a pharmaceutically acceptable salt thereof.

Embodiment 12: The method according to any one of embodiments 1-11, wherein said one or more compounds comprise compound A2, or a pharmaceutically acceptable salt thereof.

Embodiment 13: The method according to any one of embodiments 1-12, wherein said one or more compounds comprise compound A5, or a pharmaceutically acceptable salt thereof.

Embodiment 14: The method according to any one of embodiments 1-13, wherein said one or more compounds comprise compound D5, or a pharmaceutically acceptable salt thereof.

Embodiment 15: The method according to any one of embodiments 1-14, wherein said one or more compounds comprise compound A6, or a pharmaceutically acceptable salt thereof.

Embodiment 16: The method according to any one of embodiments 1-15, wherein said one or more compounds comprise compound A4, or a pharmaceutically acceptable salt thereof.

Embodiment 17: The method according to any one of embodiments 1-16, wherein said one or more compounds comprise compound D6, or a pharmaceutically acceptable salt thereof.

Embodiment 18: The method according to any one of embodiments 1-17, wherein said one or more compounds comprise compound, H5, or a pharmaceutically acceptable salt thereof.

Embodiment 19: The method according to any one of embodiments 1-18, wherein said one or more compounds comprise compound B6, or a pharmaceutically acceptable salt thereof.

Embodiment 20: The method according to any one of embodiments 1-19, wherein said one or more compounds comprise compound C5, or a pharmaceutically acceptable salt thereof.

Embodiment 21: The method according to any one of embodiments 1-20, wherein said one or more compounds comprise compound F5, or a pharmaceutically acceptable salt thereof.

Embodiment 22: The method according to any one of embodiments 1-21, wherein said one or more compounds comprise compound C6, or a pharmaceutically acceptable salt thereof.

Embodiment 23: The method according to any one of embodiments 1-22, wherein said one or more compounds comprise compound D4, or a pharmaceutically acceptable salt thereof.

Embodiment 24: The method according to any one of embodiments 1-23, wherein said one or more compounds comprise compound B5, or a pharmaceutically acceptable salt thereof.

Embodiment 25: The method according to any one of embodiments 1-24, wherein said one or more compounds comprise compound, H3, or a pharmaceutically acceptable salt thereof.

Embodiment 26: The method according to any one of embodiments 1-25, wherein said one or more compounds comprise compound B3, or a pharmaceutically acceptable salt thereof.

Embodiment 27: The method according to any one of embodiments 1-26, wherein said one or more compounds comprise compound G5, or a pharmaceutically acceptable salt thereof.

Embodiment 28: The method according to any one of embodiments 1-27, wherein said one or more compounds comprise compound E5, or a pharmaceutically acceptable salt thereof.

Embodiment 29: The method according to any one of embodiments 1-28, wherein said one or more compounds comprise compound B4, or a pharmaceutically acceptable salt thereof.

Embodiment 30: The method according to any one of embodiments 1-29, wherein said one or more compounds comprise compound E4, or a pharmaceutically acceptable salt thereof.

Embodiment 31: The method according to any one of embodiments 1-30, wherein said one or more compounds comprise compound G4, or a pharmaceutically acceptable salt thereof.

Embodiment 32: The method according to any one of embodiments 1-31, wherein said one or more compounds comprise compound F4, or a pharmaceutically acceptable salt thereof.

Embodiment 33: The method according to any one of embodiments 1-32, wherein said one or more compounds comprise compound E3, or a pharmaceutically acceptable salt thereof.

Embodiment 34: The method according to any one of embodiments 1-33, wherein said one or more compounds comprise compound B2, or a pharmaceutically acceptable salt thereof.

Embodiment 35: The method according to any one of embodiments 1-34, wherein said one or more compounds comprise compound G3, or a pharmaceutically acceptable salt thereof.

Embodiment 36: The method according to any one of embodiments 1-35, wherein said one or more compounds comprise compound F3, or a pharmaceutically acceptable salt thereof.

Embodiment 37: The method according to any one of embodiments 1-36, wherein said one or more compounds comprise compound C4, or a pharmaceutically acceptable salt thereof.

Embodiment 38: The method according to any one of embodiments 1-37, wherein said one or more compounds comprise compound H4, or a pharmaceutically acceptable salt thereof.

Embodiment 39: The method according to any one of embodiments 1-38, wherein said one or more compounds comprise compound D2, or a pharmaceutically acceptable salt thereof.

Embodiment 40: The method according to any one of embodiments 1-39, wherein said one or more compounds comprise compound C3, or a pharmaceutically acceptable salt thereof.

Embodiment 41: The method according to any one of embodiments 1-40, wherein said one or more compounds comprise compound E2, or a pharmaceutically acceptable salt thereof.

Embodiment 42: The method according to any one of embodiments 1-41, wherein said one or more compounds comprise compound E6, or a pharmaceutically acceptable salt thereof.

Embodiment 43: The method according to any one of embodiments 3-42, wherein said method comprises prophylaxis of said disease or condition and said administering comprises administering to a subject that is asymptomatic for said disease or condition.

Embodiment 44: The method according to any one of embodiments 3-42, wherein said method comprises treatment of said disease or condition and said method mitigates one or more symptoms of said disease or condition, or slows or stops the progression of said disease or condition.

Embodiment 45: The method according to any one of embodiments 3-44, wherein said disease or condition comprises a disorder selected from the group consisting of a neurodegenerative disease, sarcopenia, liver disease, type 2 diabetes, metabolic syndrome, a cardiac disorder, kidney disease, stroke, arthritis, and cancer.

Embodiment 46: The method of embodiment 45, wherein said disease or condition comprises a neurodegenerative disease.

Embodiment 47: The method of embodiment 46, wherein the neurodegenerative disease is selected from the group consisting of Alzheimer's disease, Parkinson's Disease, mild cognitive impairment, and age-related dementia.

Embodiment 48: The method of embodiment 46, wherein the neurodegenerative disease is selected from the group consisting of Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), MELAS—Mitochondrial Encephalopathy, Lactic Acidosis and Stroke, Multiple System Atrophy, Multiple sclerosis, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Spinocerebellar ataxia (multiple types with varying characteristics), Spinal muscular atrophy, Steele-Richardson-Olszewski disease, Tabes dorsalis, Tay-Sachs Disease, and Toxic encephalopathy.

Embodiment 49: The method of embodiment 45, wherein said disease or condition comprises a liver disease.

Embodiment 50: The method of embodiment 49, wherein the liver disease comprises a disease selected from the group consisting of SERPINA1/α1-anti-trypsin (ATT) deficiency, nonalcoholic fatty liver disease (NAFLD), alcoholic liver disease (ALD), drug-induced liver injury, ischemia/reperfusion injury, hepatitis, and liver cirrhosis.

Embodiment 51: The method of embodiment 45, wherein said disease or condition comprises type II diabetes and/or metabolic syndrome.

Embodiment 52: The method of embodiment 45, wherein said disease or condition comprises a cancer.

Embodiment 53: The method of embodiment 52, wherein said cancer comprise a cancer selected from the group consisting of hepatocarcinoma, acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 54: The method of embodiment 45, wherein said disease or condition is not a cancer.

Embodiment 55: The method of embodiment 46, wherein the neurodegenerative disease is not Parkinson's disease.

Embodiment 56: The method of embodiment 46, wherein the neurodegenerative disease is not a psychiatric disorder (e.g., is not schizophrenia, bipolar disorder, depression, social anxiety disorder, or another psychiatric disorder).

Embodiment 57: A method of improving a measure of life span and/or health span in a mammalian subject, said method comprising:

administering to said subject an effective amount of one or more compounds selected from the group consisting of 2,3,6,7,10,11-Hexahydro-1H,5H-cyclopenta(3,4)(1)benzopyrano(6,7,8-ij)quinolizin-12(9H)-one (Coumarin 106; CAS Registry No. 41175-45-5), C3, H2, F2, D3, G2, A3, C2, A2, A5, D5, A6, A4, D6, H5, B6, C5, F5, C6, D4, B5, H3, B3, G5, E5, B4, E4, G4, F4, E3, B2, G3, F3, C4, H4, D2, C3, E2, and E6, or a pharmaceutically acceptable salt thereof.

Embodiment 58: The method of embodiment 57, wherein said one or more compounds comprise compound C1, or a pharmaceutically acceptable salt thereof.

Embodiment 59: The method according to any one of embodiments 57-58, wherein said one or more compounds comprise compound C3, or a pharmaceutically acceptable salt thereof.

Embodiment 60: The method according to any one of embodiments 57-59, wherein said one or more compounds comprise compound H2, or a pharmaceutically acceptable salt thereof.

Embodiment 61: The method according to any one of embodiments 57-60, wherein said one or more compounds comprise compound F2, or a pharmaceutically acceptable salt thereof.

Embodiment 62: The method according to any one of embodiments 57-61, wherein said one or more compounds comprise compound D3, or a pharmaceutically acceptable salt thereof.

Embodiment 63: The method according to any one of embodiments 57-62, wherein said one or more compounds comprise compound G2, or a pharmaceutically acceptable salt thereof.

Embodiment 64: The method according to any one of embodiments 57-63, wherein said one or more compounds comprise compound A3, or a pharmaceutically acceptable salt thereof.

Embodiment 65: The method according to any one of embodiments 57-64, wherein said one or more compounds comprise compound C2, or a pharmaceutically acceptable salt thereof.

Embodiment 66: The method according to any one of embodiments 57-65, wherein said one or more compounds comprise compound A2, or a pharmaceutically acceptable salt thereof.

Embodiment 67: The method according to any one of embodiments 57-66, wherein said one or more compounds comprise compound A5, or a pharmaceutically acceptable salt thereof.

Embodiment 68: The method according to any one of embodiments 57-67, wherein said one or more compounds comprise compound D5, or a pharmaceutically acceptable salt thereof.

Embodiment 69: The method according to any one of embodiments 57-68, wherein said one or more compounds comprise compound A6, or a pharmaceutically acceptable salt thereof.

Embodiment 70: The method according to any one of embodiments 57-69, wherein said one or more compounds comprise compound A4, or a pharmaceutically acceptable salt thereof.

Embodiment 71: The method according to any one of embodiments 57-70, wherein said one or more compounds comprise compound D6, or a pharmaceutically acceptable salt thereof.

Embodiment 72: The method according to any one of embodiments 57-71, wherein said one or more compounds comprise compound, H5, or a pharmaceutically acceptable salt thereof.

Embodiment 73: The method according to any one of embodiments 57-72, wherein said one or more compounds comprise compound B6, or a pharmaceutically acceptable salt thereof.

Embodiment 74: The method according to any one of embodiments 57-73, wherein said one or more compounds comprise compound C5, or a pharmaceutically acceptable salt thereof.

Embodiment 75: The method according to any one of embodiments 57-74, wherein said one or more compounds comprise compound F5, or a pharmaceutically acceptable salt thereof.

Embodiment 76: The method according to any one of embodiments 57-75, wherein said one or more compounds comprise compound C6, or a pharmaceutically acceptable salt thereof.

Embodiment 77: The method according to any one of embodiments 57-76, wherein said one or more compounds comprise compound D4, or a pharmaceutically acceptable salt thereof.

Embodiment 78: The method according to any one of embodiments 57-77, wherein said one or more compounds comprise compound B5, or a pharmaceutically acceptable salt thereof.

Embodiment 79: The method according to any one of embodiments 57-78, wherein said one or more compounds comprise compound, H3, or a pharmaceutically acceptable salt thereof.

Embodiment 80: The method according to any one of embodiments 57-79, wherein said one or more compounds comprise compound B3, or a pharmaceutically acceptable salt thereof.

Embodiment 81: The method according to any one of embodiments 57-80, wherein said one or more compounds comprise compound G5, or a pharmaceutically acceptable salt thereof.

Embodiment 82: The method according to any one of embodiments 57-81, wherein said one or more compounds comprise compound E5, or a pharmaceutically acceptable salt thereof.

Embodiment 83: The method according to any one of embodiments 57-82, wherein said one or more compounds comprise compound B4, or a pharmaceutically acceptable salt thereof.

Embodiment 84: The method according to any one of embodiments 57-83, wherein said one or more compounds comprise compound E4, or a pharmaceutically acceptable salt thereof.

Embodiment 85: The method according to any one of embodiments 57-84, wherein said one or more compounds comprise compound G4, or a pharmaceutically acceptable salt thereof.

Embodiment 86: The method according to any one of embodiments 57-85, wherein said one or more compounds comprise compound F4, or a pharmaceutically acceptable salt thereof.

Embodiment 87: The method according to any one of embodiments 57-86, wherein said one or more compounds comprise compound E3, or a pharmaceutically acceptable salt thereof.

Embodiment 88: The method according to any one of embodiments 57-87, wherein said one or more compounds comprise compound B2, or a pharmaceutically acceptable salt thereof.

Embodiment 89: The method according to any one of embodiments 57-88, wherein said one or more compounds comprise compound G3, or a pharmaceutically acceptable salt thereof.

Embodiment 90: The method according to any one of embodiments 57-89, wherein said one or more compounds comprise compound F3, or a pharmaceutically acceptable salt thereof.

Embodiment 91: The method according to any one of embodiments 57-90, wherein said one or more compounds comprise compound C4, or a pharmaceutically acceptable salt thereof.

Embodiment 92: The method according to any one of embodiments 57-91, wherein said one or more compounds comprise compound H4, or a pharmaceutically acceptable salt thereof.

Embodiment 93: The method according to any one of embodiments 57-92, wherein said one or more compounds comprise compound D2, or a pharmaceutically acceptable salt thereof.

Embodiment 94: The method according to any one of embodiments 57-93, wherein said one or more compounds comprise compound C3, or a pharmaceutically acceptable salt thereof.

Embodiment 95: The method according to any one of embodiments 57-94, wherein said one or more compounds comprise compound E2, or a pharmaceutically acceptable salt thereof.

Embodiment 96: The method according to any one of embodiments 57-95, wherein said one or more compounds comprise compound E6, or a pharmaceutically acceptable salt thereof.

Embodiment 97: The method according to any one of embodiments 57-96, wherein the improved measure of life span and/or health span comprises one or more of the following: a reduction in frailty, an improvement in function in an age-related disability, the mitigation of a symptom of an age-related disease, and/or a delay in onset of frailty, age-related disability, or age-related disease, relative to the condition of the subject before administration of the Coumarin 106 to a control population.

Embodiment 98: The method of embodiment 97, wherein the improved measure of life span and/or health span comprises a reduction in frailty.

Embodiment 99: The method of embodiment 98, wherein the reduction in frailty comprises one or more of the following: increased strength, weight gain, faster mobility, increased energy, increased levels of activity, increased endurance, and enhanced behavioral response to a sensory cue, wherein the reduction is relative to the condition of the subject before administration of the Coumarin 106 to a control population.

Embodiment 100: The method of embodiment 97, wherein the improved measure of life span and/or health span comprises one or more changes selected from the group consisting of a decrease in one or more inflammatory biomarkers, an improvement in glucose homeostasis, and a decrease in one of more biomarkers of clotting activation.

Embodiment 101: The method according to any one of embodiments 97-100, wherein the improved measure of life span and/or health span comprises an improvement in one or more parameters selected from the group consisting of cholesterol level, triglyceride level, high density lipoprotein level, and blood pressure.

Embodiment 102: The method according to any one of embodiments 97-101, wherein the improved measure of life span and/or health span comprises a reduction in, a reversal of, or delay in onset of sarcopenia, relative to the condition of the subject before administration of the coumarin compound(s).

Embodiment 103: The method according to any one of embodiments 97-102, wherein the improved measure of life span and/or health span comprises a reduction in, a reversal of, or delay in onset of sarcopenia, relative to the condition of the subject as compared to a control population.

Embodiment 104: The method according to any one of embodiments 97-103, wherein the improved measure of life span and/or health span comprises a reduction in, a reversal of, or delay in onset of an age-related increase in lipofuscin accumulation in one or more tissues selected from the group consisting of brain, heart, liver, spleen, and kidney, relative to the condition of the subject before administration of the coumarin compound(s).

Embodiment 105: The method according to any one of embodiments 97-104, wherein the improved measure of life span and/or health span comprises a reduction in, a reversal of, or delay in onset of an age-related increase in lipofuscin accumulation in one or more tissues selected from the group consisting of brain, heart, liver, spleen, and kidney, relative to a control population.

Embodiment 106: The method according to any one of embodiments 97-105, wherein the improved measure of life span and/or health span comprises an amelioration of one or more symptoms, and/or a reduction in the rate of progression of a disease is selected from the group consisting of osteoporosis, arthritis, cataracts, macular degeneration, and cardiovascular disease.

Embodiment 107: The method of any one of embodiments 97 to 106, wherein the subject is suffering from, or determined to be at risk for, frailty, an age-related disability, or an age-related disease.

Embodiment 108: The method of embodiment 107, wherein the subject is suffering from, or determined to be at risk for, frailty.

Embodiment 109: The method of any one of embodiments 97 to 108, wherein the subject is determined to have at least three symptoms selected from the group consisting of weakness, weight loss, slowed mobility, fatigue, low levels of activity, poor endurance, and impaired behavioral response to a sensory cue.

Embodiment 110: The method of any one of embodiments 97 to 109, wherein the subject is determined to have one or more symptoms selected from the group consisting of an increase in one or more inflammatory biomarkers, glucose homeostasis impairment, and an increase in one of more biomarkers of clotting activation.

Embodiment 111: The method of any one of embodiments 97 to 110, wherein the subject is suffering from sarcopenia.

Embodiment 112: The method of any one of embodiments 97 to 111, wherein the subject has lipofuscin accumulation in one or more tissues selected from the group consisting of brain, heart, liver, spleen, and kidney.

Embodiment 113: The method of any one of embodiments 97 to 112, wherein the improvement in a measure of life span and/or health span comprises an enhanced ability to maintain homeostasis during the application of a stressor and/or a reduced time required to return to homeostasis after the application of a stressor.

Embodiment 114: The method of embodiment 113, wherein the stressor is selected from drug-induced oxidative stress, exposure to heat, and exposure to cold.

Embodiment 115: The method of any one of embodiments 113 to 114, wherein the subject has been determined to have a reduced ability to maintain homeostasis during the application of a stressor and/or an extended time required to return to homeostasis after the application of a stressor, wherein the reduced ability or extended time is relative to the condition of the subject at a previous time or relative to a normal ability or time.

Embodiment 116: The method of any one of embodiments 97 to 115, wherein the measure of life span and/or health span comprises the level and/or activity of a molecule that plays a role in protein trafficking, the autophagy pathway, ubiquitination, and/or lysosomal degradation of proteins.

Embodiment 117: The method of any one of embodiments 97 to 116, wherein the subject has been determined to have an abnormal level and/or activity of a molecule that plays a role in protein trafficking, the autophagy pathway, ubiquitination, and/or lysosomal degradation of proteins.

Embodiment 118: The method of any one of embodiments 116 to 117, wherein the molecule comprises lysosome-associated membrane protein-2 (LAMP-2).

Embodiment 119: The method of any one of embodiments 97 to 118, wherein the measure of life span and/or health span comprises the number of inclusion bodies in muscle tissue.

Embodiment 120: The method of any one of embodiments 97 to 119, wherein the subject has been determined to have abnormal inclusion bodies in muscle tissue.

Embodiment 121: The method of any one of embodiments 97 to 120, wherein the measure of life span and/or health span comprises mitochondrial function and/or morphology.

Embodiment 122: The method of any one of embodiments 97 to 121, wherein the subject has been determined to have an abnormality in mitochondrial function and/or morphology.

Embodiment 123: The method of any one of embodiments 97 to 122, wherein the improvement in the measure of life span and/or health span is at least about 40%, e.g., at least about 50%, 60%, or more, relative to the condition of the subject before administration of the coumarin compound(s).

Embodiment 124: A method of mitigating in a subject one or more symptoms associated with a neurodegenerative condition or slowing the progression of a neurodegenerative condition, or preventing or delaying the onset of a neurodegenerative condition, said method comprising:

administering to the subject one or more compounds selected from the group consisting of 2,3,6,7,10,11-Hexahydro-1H,5H-cyclopenta(3,4)(1)benzopyrano(6, 7,8-ij)quinolizin-12(9H)-one (Coumarin 106; CAS Registry No. 41175-45-5), C3, H2, F2, D3, G2, A3, C2, A2, A5, D5, A6, A4, D6, H5, B6, C5, F5, C6, D4, B5, H3, B3, G5, E5, B4, E4, G4, F4, E3, B2, G3, F3, C4, H4, D2, C3, E2, and E6, or a pharmaceutically acceptable salt thereof.

Embodiment 125: The method of embodiment 124, wherein said one or more compounds comprise compound C1, or a pharmaceutically acceptable salt thereof.

Embodiment 126: The method according to any one of embodiments 124-125, wherein said one or more compounds comprise compound C3, or a pharmaceutically acceptable salt thereof.

Embodiment 127: The method according to any one of embodiments 124-126, wherein said one or more compounds comprise compound H2, or a pharmaceutically acceptable salt thereof.

Embodiment 128: The method according to any one of embodiments 124-127, wherein said one or more compounds comprise compound F2, or a pharmaceutically acceptable salt thereof.

Embodiment 129: The method according to any one of embodiments 124-128, wherein said one or more compounds comprise compound D3, or a pharmaceutically acceptable salt thereof.

Embodiment 130: The method according to any one of embodiments 124-129, wherein said one or more compounds comprise compound G2, or a pharmaceutically acceptable salt thereof.

Embodiment 131: The method according to any one of embodiments 57-130, wherein said one or more compounds comprise compound A3, or a pharmaceutically acceptable salt thereof.

Embodiment 132: The method according to any one of embodiments 57-131, wherein said one or more compounds comprise compound C2, or a pharmaceutically acceptable salt thereof.

Embodiment 133: The method according to any one of embodiments 57-132, wherein said one or more compounds comprise compound A2, or a pharmaceutically acceptable salt thereof.

Embodiment 134: The method according to any one of embodiments 57-133, wherein said one or more compounds comprise compound A5, or a pharmaceutically acceptable salt thereof.

Embodiment 135: The method according to any one of embodiments 57-134, wherein said one or more compounds comprise compound D5, or a pharmaceutically acceptable salt thereof.

Embodiment 136: The method according to any one of embodiments 57-135, wherein said one or more compounds comprise compound A6, or a pharmaceutically acceptable salt thereof.

Embodiment 137: The method according to any one of embodiments 57-136, wherein said one or more compounds comprise compound A4.

Embodiment 138: The method according to any one of embodiments 57-137, wherein said one or more compounds comprise compound D6, or a pharmaceutically acceptable salt thereof.

Embodiment 139: The method according to any one of embodiments 57-138, wherein said one or more compounds comprise compound, H5, or a pharmaceutically acceptable salt thereof.

Embodiment 140: The method according to any one of embodiments 57-139, wherein said one or more compounds comprise compound B6, or a pharmaceutically acceptable salt thereof.

Embodiment 141: The method according to any one of embodiments 57-140, wherein said one or more compounds comprise compound C5, or a pharmaceutically acceptable salt thereof.

Embodiment 142: The method according to any one of embodiments 57-141, wherein said one or more compounds comprise compound F5, or a pharmaceutically acceptable salt thereof.

Embodiment 143: The method according to any one of embodiments 57-142, wherein said one or more compounds comprise compound C6, or a pharmaceutically acceptable salt thereof.

Embodiment 144: The method according to any one of embodiments 57-143, wherein said one or more compounds comprise compound D4, or a pharmaceutically acceptable salt thereof.

Embodiment 145: The method according to any one of embodiments 57-144, wherein said one or more compounds comprise compound B5, or a pharmaceutically acceptable salt thereof.

Embodiment 146: The method according to any one of embodiments 57-145, wherein said one or more compounds comprise compound, H3, or a pharmaceutically acceptable salt thereof.

Embodiment 147: The method according to any one of embodiments 57-146, wherein said one or more compounds comprise compound B3, or a pharmaceutically acceptable salt thereof.

Embodiment 148: The method according to any one of embodiments 57-147, wherein said one or more compounds comprise compound G5, or a pharmaceutically acceptable salt thereof.

Embodiment 149: The method according to any one of embodiments 57-148, wherein said one or more compounds comprise compound E5, or a pharmaceutically acceptable salt thereof.

Embodiment 150: The method according to any one of embodiments 57-149, wherein said one or more compounds comprise compound B4, or a pharmaceutically acceptable salt thereof.

Embodiment 151: The method according to any one of embodiments 57-150, wherein said one or more compounds comprise compound E4, or a pharmaceutically acceptable salt thereof.

Embodiment 152: The method according to any one of embodiments 57-151, wherein said one or more compounds comprise compound G4, or a pharmaceutically acceptable salt thereof.

Embodiment 153: The method according to any one of embodiments 57-152, wherein said one or more compounds comprise compound F4, or a pharmaceutically acceptable salt thereof.

Embodiment 154: The method according to any one of embodiments 57-153, wherein said one or more compounds comprise compound E3, or a pharmaceutically acceptable salt thereof.

Embodiment 155: The method according to any one of embodiments 57-154, wherein said one or more compounds comprise compound B2, or a pharmaceutically acceptable salt thereof.

Embodiment 156: The method according to any one of embodiments 57-155, wherein said one or more compounds comprise compound G3, or a pharmaceutically acceptable salt thereof.

Embodiment 157: The method according to any one of embodiments 57-156, wherein said one or more compounds comprise compound F3, or a pharmaceutically acceptable salt thereof.

Embodiment 158: The method according to any one of embodiments 57-157, wherein said one or more compounds comprise compound C4, or a pharmaceutically acceptable salt thereof.

Embodiment 159: The method according to any one of embodiments 57-158, wherein said one or more compounds comprise compound H4, or a pharmaceutically acceptable salt thereof.

Embodiment 160: The method according to any one of embodiments 57-159, wherein said one or more compounds comprise compound D2, or a pharmaceutically acceptable salt thereof.

Embodiment 161: The method according to any one of embodiments 57-160, wherein said one or more compounds comprise compound C3, or a pharmaceutically acceptable salt thereof.

Embodiment 162: The method according to any one of embodiments 57-161, wherein said one or more compounds comprise compound E2, or a pharmaceutically acceptable salt thereof.

Embodiment 163: The method according to any one of embodiments 57-162, wherein said one or more compounds comprise compound E6, or a pharmaceutically acceptable salt thereof.

Embodiment 164: The method according to any one of embodiments 124-163, wherein said neurodegenerative condition comprises Parkinson's disease.

Embodiment 165: The method according to any one of embodiments 124-163, wherein said neurodegenerative condition comprises mild cognitive impairment or age-related dementia.

Embodiment 166: The method of embodiment 124, wherein said neurodegenerative condition comprises Alzheimer's disease.

Embodiment 167: The method according to any one of embodiments 124-166, wherein said subject is asymptomatic and said method is prophylactic.

Embodiment 168: The method of embodiment 167, wherein administration of the compound delays or prevents the progression of MCI to Alzheimer's disease, and/or delays the onset of Alzheimer's disease, or delays the onset of Parkinson's Disease.

Embodiment 169: The method of any one of embodiments 167 to 168, wherein the subject is at risk of developing Alzheimer's disease or Parkinson's Disease.

Embodiment 170: The method of any one of embodiments 167 to 169, wherein the subject has a familial risk for having Alzheimer's disease or Parkinson's Disease.

Embodiment 171: The method of any one of embodiments 167 to 170, wherein the subject has a familial Alzheimer's disease (FAD) mutation.

Embodiment 172: The method of any one of embodiments 167 to 171, wherein the subject exhibits or has exhibited olfactory impairment in an olfactory challenge test.

Embodiment 173: The method of any one of embodiments 124 to 172, wherein said method produces a reduction in the CSF of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio.

Embodiment 174: The method of any one of embodiments 124 to 173, wherein the method provides a reduction of misfolded protein deposit (e.g., plaque) load in the brain of the subject.

Embodiment 175: The method of any one of embodiments 124 to 174, wherein the method produces an improvement in the cognitive abilities of the subject.

Embodiment 176: The method of any one of embodiments 124 to 175, wherein the method produces an improvement in, a stabilization of, or a reduction in the rate of decline of the clinical dementia rating (CDR) of the subject.

Embodiment 177: The method of any one of embodiments 1 to 176, wherein the coumarin compound(s) are administered in more than one dose.

Embodiment 178: The method of any one of embodiments 1 to 177, wherein the administering is over a period of at least 1 month.

Embodiment 179: The method of any one of embodiments 1 to 178, wherein the administering is over a period of at least 6 months.

Embodiment 180: The method of any one of embodiments 1 to 179, wherein the administering is over a period of at least 1 year.

Embodiment 181: The method of any one of embodiments 1 to 180, wherein the coumarin(s) are administered via a route selected from the group consisting of intravenous, intraarterial, intrathecal, intradermal, intracavitary, oral, rectal, intramuscular, subcutaneous, intracisternal, intravaginal, intraperitoneal, topical, buccal, intranasal, intrapulmonary, isophoretic, and transdermal.

Embodiment 182: The method of any one of embodiments 1 to 181, wherein the subject is human.

Embodiment 183: The method of embodiment 182, where the human perceives an improvement in quality of life.

Embodiment 184: The method of any one of embodiments 1 to 181, wherein the subject is a non-human mammal.

Embodiment 185: A pharmaceutical formulation, said pharmaceutical formulation comprising:

one or more compounds selected from the group consisting of 2,3,6,7,10,11-Hexahydro-1H,5H-cyclopenta(3,4)(1)benzopyrano(6,7,8-ij)quinolizin-12(9H)-one (Coumarin 106; CAS Registry No. 41175-45-5), C3, H2, F2, D3, G2, A3, C2, A2, A5, D5, A6, A4, D6, H5, B6, C5, F5, C6, D4, B5, H3, B3, G5, E5, B4, E4, G4, F4, E3, B2, G3, F3, C4, H4, D2, C3, E2, and E6, or a pharmaceutically acceptable salt thereof.

Embodiment 186: The pharmaceutical formulation of embodiment 185, wherein said one or more compounds comprise compound C1, or a pharmaceutically acceptable salt thereof.

Embodiment 187: The pharmaceutical formulation according to any one of embodiments 124-186, wherein said one or more compounds comprise compound C3, or a pharmaceutically acceptable salt thereof.

Embodiment 188: The pharmaceutical formulation according to any one of embodiments 124-187, wherein said one or more compounds comprise compound H2, or a pharmaceutically acceptable salt thereof.

Embodiment 189: The pharmaceutical formulation according to any one of embodiments 124-188, wherein said one or more compounds comprise compound F2, or a pharmaceutically acceptable salt thereof.

Embodiment 190: The pharmaceutical formulation according to any one of embodiments 124-189, wherein said one or more compounds comprise compound D3, or a pharmaceutically acceptable salt thereof.

Embodiment 191: The pharmaceutical formulation according to any one of embodiments 124-190, wherein said one or more compounds comprise compound G2, or a pharmaceutically acceptable salt thereof.

Embodiment 192: The pharmaceutical formulation according to any one of embodiments 57-191, wherein said one or more compounds comprise compound A3, or a pharmaceutically acceptable salt thereof.

Embodiment 193: The pharmaceutical formulation according to any one of embodiments 57-192, wherein said one or more compounds comprise compound C2, or a pharmaceutically acceptable salt thereof.

Embodiment 194: The pharmaceutical formulation according to any one of embodiments 57-193, wherein said one or more compounds comprise compound A2, or a pharmaceutically acceptable salt thereof.

Embodiment 195: The pharmaceutical formulation according to any one of embodiments 57-194, wherein said one or more compounds comprise compound A5, or a pharmaceutically acceptable salt thereof.

Embodiment 196: The pharmaceutical formulation according to any one of embodiments 57-195, wherein said one or more compounds comprise compound D5, or a pharmaceutically acceptable salt thereof.

Embodiment 197: The pharmaceutical formulation according to any one of embodiments 57-196, wherein said one or more compounds comprise compound A6, or a pharmaceutically acceptable salt thereof.

Embodiment 198: The pharmaceutical formulation according to any one of embodiments 57-197, wherein said one or more compounds comprise compound A4, or a pharmaceutically acceptable salt thereof.

Embodiment 199: The pharmaceutical formulation according to any one of embodiments 57-198, wherein said one or more compounds comprise compound D6, or a pharmaceutically acceptable salt thereof.

Embodiment 200: The pharmaceutical formulation according to any one of embodiments 57-199, wherein said one or more compounds comprise compound, H5, or a pharmaceutically acceptable salt thereof.

Embodiment 201: The pharmaceutical formulation according to any one of embodiments 57-200, wherein said one or more compounds comprise compound B6, or a pharmaceutically acceptable salt thereof.

Embodiment 202: The pharmaceutical formulation according to any one of embodiments 57-201, wherein said one or more compounds comprise compound C5, or a pharmaceutically acceptable salt thereof.

Embodiment 203: The pharmaceutical formulation according to any one of embodiments 57-202, wherein said one or more compounds comprise compound F5, or a pharmaceutically acceptable salt thereof.

Embodiment 204: The pharmaceutical formulation according to any one of embodiments 57-203, wherein said one or more compounds comprise compound C6, or a pharmaceutically acceptable salt thereof.

Embodiment 205: The pharmaceutical formulation according to any one of embodiments 57-204, wherein said one or more compounds comprise compound D4, or a pharmaceutically acceptable salt thereof.

Embodiment 206: The pharmaceutical formulation according to any one of embodiments 57-205, wherein said one or more compounds comprise compound B5, or a pharmaceutically acceptable salt thereof.

Embodiment 207: The pharmaceutical formulation according to any one of embodiments 57-206, wherein said one or more compounds comprise compound, H3, or a pharmaceutically acceptable salt thereof.

Embodiment 208: The pharmaceutical formulation according to any one of embodiments 57-207, wherein said one or more compounds comprise compound B3, or a pharmaceutically acceptable salt thereof.

Embodiment 209: The pharmaceutical formulation according to any one of embodiments 57-208, wherein said one or more compounds comprise compound G5, or a pharmaceutically acceptable salt thereof.

Embodiment 210: The pharmaceutical formulation according to any one of embodiments 57-209, wherein said one or more compounds comprise compound E5, or a pharmaceutically acceptable salt thereof.

Embodiment 211: The pharmaceutical formulation according to any one of embodiments 57-210, wherein said one or more compounds comprise compound B4, or a pharmaceutically acceptable salt thereof.

Embodiment 212: The pharmaceutical formulation according to any one of embodiments 57-211, wherein said one or more compounds comprise compound E4, or a pharmaceutically acceptable salt thereof.

Embodiment 213: The pharmaceutical formulation according to any one of embodiments 57-212, wherein said one or more compounds comprise compound G4, or a pharmaceutically acceptable salt thereof.

Embodiment 214: The pharmaceutical formulation according to any one of embodiments 57-213, wherein said one or more compounds comprise compound F4, or a pharmaceutically acceptable salt thereof.

Embodiment 215: The pharmaceutical formulation according to any one of embodiments 57-214, wherein said one or more compounds comprise compound E3, or a pharmaceutically acceptable salt thereof.

Embodiment 216: The pharmaceutical formulation according to any one of embodiments 57-215, wherein said one or more compounds comprise compound B2, or a pharmaceutically acceptable salt thereof.

Embodiment 217: The pharmaceutical formulation according to any one of embodiments 57-216, wherein said one or more compounds comprise compound G3, or a pharmaceutically acceptable salt thereof.

Embodiment 218: The pharmaceutical formulation according to any one of embodiments 57-217, wherein said one or more compounds comprise compound F3, or a pharmaceutically acceptable salt thereof.

Embodiment 219: The pharmaceutical formulation according to any one of embodiments 57-218, wherein said one or more compounds comprise compound C4, or a pharmaceutically acceptable salt thereof.

Embodiment 220: The pharmaceutical formulation according to any one of embodiments 57-219, wherein said one or more compounds comprise compound H4, or a pharmaceutically acceptable salt thereof.

Embodiment 221: The pharmaceutical formulation according to any one of embodiments 57-220, wherein said one or more compounds comprise compound D2, or a pharmaceutically acceptable salt thereof.

Embodiment 222: The pharmaceutical formulation according to any one of embodiments 57-221, wherein said one or more compounds comprise compound C3, or a pharmaceutically acceptable salt thereof.

Embodiment 223: The pharmaceutical formulation according to any one of embodiments 57-222, wherein said one or more compounds comprise compound E2, or a pharmaceutically acceptable salt thereof.

Embodiment 224: The pharmaceutical formulation according to any one of embodiments 57-223, wherein said one or more compounds comprise compound E6, or a pharmaceutically acceptable salt thereof.

Embodiment 225: The pharmaceutical formulation according to any one of embodiments 185-224, wherein said formulation is substantially sterile.

Embodiment 226: The pharmaceutical formulation according to any one of embodiments 185-225, wherein said formulation is a unit dosage formulation.

Embodiment 227: The pharmaceutical formulation according to any one of embodiments 185-226, wherein said formulation is formulated for administration via a route selected from the group consisting of oral delivery, isophoretic delivery, subdermal delivery, transdermal delivery, parenteral delivery, aerosol administration, administration via inhalation, intravenous administration, and rectal administration.

Embodiment 228: The pharmaceutical formulation according to any one of embodiments 185-227, wherein said compound(s) comprise substantially pure R enantiomers.

Embodiment 229: The pharmaceutical formulation according to any one of embodiments 185-227, wherein said compound(s) comprise substantially pure S enantiomers.

Definitions

The terms "subject," "individual," and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase “a subject in need thereof” refers to a subject, as described infra, that is characterized by a disease and/or pathology that can respond favorably by induction and/or promotion of autophagy (e.g., a subject having a chronic disease of aging). In certain embodiments a subject in need thereof comprises a subject diagnosed with a a neurodegenerative condition described herein (e.g., Alzheimer’s disease, Parkinson’s Disease, mild cognitive impairment (MCI), age related dementia, and the like) or a subject at risk for such a neurodegenerative condition.

The term “treat” when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment, which includes a delay in the onset or the prevention of the onset of a pathology or disease.

The term “substantially pure” when used with respect to enantiomers indicates that one particular enantiomer (e.g. an S enantiomer) is substantially free of its stereoisomer. In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art.

BRIEF DESCRIPTION OF THE DRAWINGS

FIG. 8 A) Representative Western blot analysis of detergent-insoluble tau levels in control versus three independent TSC1-mutant SY5Y cell lines (A1, A3, A3A9) treated with 10 μM C1 (AIC106) versus vehicle. FIG. 8B) Quantitation of insoluble tau levels in control (Emty) versus mutant TSC1 lines treated with C1 (AIC106) versus vehicle (−). Values represent fold change versus vehicle-treated controls, *$p<0.01$.

FIG. 9A) Nuclear TFEB homologue HLH-30 levels in HLH-30 GFP tagged worms grown from day 1 at 20° C. as a measure of TFEB activation. Values are reported as average GFP intensity visualized at a young adult stage, day-5; $p<0.0002$ versus control. FIG. 9**B) TFEB mRNA levels by qPCR following 24 hrs of C1 treatment (10 μM 20 μM) in worms+/−HLH30 RNAi. Values represent RNA levels versus DMSO-only control RNAi; *$p<0.001$ versus control RNAi.

FIG. 11A) Transgenic worm strain expressing human alpha-synuclein under control of the dopamine-specific promoter grown on control or HLH-30 RNAi were exposed to 20 μM C1 versus DMSO-only controls on day-1 of adulthood. GFP+ cell counts were performed in young adults. Values represent number of animals displaying no DAergic cell loss; pooled results from 2 independent experiments. FIG. 11B) Transgenic worm strain expressing human alpha-synuclein under control of the muscle-specific promoter grown on control or HLH-30 RNAi were exposed to 20 μM C1 versus DMSO-only control on day-1 of adulthood followed by transfer to fresh plates every alternative day. Number of trashes per 30 sec were measured at day-6 and day-7 (n>60). *$p<0.03$, *$p<0.0008$, $p<0.0001$. FIG. 11C) Transgenic worms expressing Abeta tagged with GFP within glutaminergic neurons grown on control or HLH-30 RNAi were exposed to 50 or 200 μM C1 versus DMSO-only controls on day-1 of adulthood. GFP+ cell counts were performed in young adults. Values represent % intact neurons. FIG. 11**D) Transgenic worm strain expressing human Abeta under control of the muscle-specific promoter grown on control or HLH-30 RNAi were exposed to 10 μM or 20 μM C1 versus DMSO-only control on day-1 of adulthood followed by transfer to fresh plates every alternative day. Number of trashes per 30 sec were measured at day-6 and day-7 (n>60). *$p<0.03$, ****$p<0.0001$.

FIG. 12A) Increased APG:APL fusion as assessed by green to red fluorescence shift following addition of 20 μM C1 versus DMSO-only control to ttdLGG-1:GFP worms expressing a pH sensitive GFP. FIG. 12B) Increases in autophagic flux as assessed by increased GFP fluorescence within p62::GFP and plmp-1::GFP expressing worms following addition of 20 μM C1 versus DMSO-only controls.

FIG. 13A) Representative images and GFP quantification of mitochondrial content at day-5 adult worms (pges-1mtGFP; bottom) of mito::GFP reporter strains (GFP tagged to mitochondrial localizing signals) treated with C1 or DMSO control. FIG. 13B) Visualizing mitochondrial fission using mito::GFP (pmyo-3mtGFP) reporter strain. Representative GFP image shown in upper panel. Representative images (lower panel) showing mitochondrial fission after 48 hrs of C1 or control treatment (63× oil). Images converted to black & white format using NIH ImageJ software for quantification of fragmented mitochondria, denoted as white puncta here.

FIG. 14A) Basal and maximal respiration measured in live worms in the Seahorse following addition of C1 (50, 200 μM). Values are reported as oxygen consumption rate (OCR, pmol/min/mg protein)+/− FCCP addition; *p<0.05; p<0.01. FIG. 14**B) Sensitivity to treatment for with increasing concentrations of the mitochondrial uncoupler FCCP in the absence and presence of C1 (20, 50 μM; 1 hr). Values are reported as % of live worms per plate, *p<0.01 versus FCCP alone.

DETAILED DESCRIPTION

Chronic disease in late life is a massive economic and social burden. No treatments that halt or reverse many of these diseases exist. Our goal is to develop general therapeutic approaches that are effective against multiple disease states. Transient activation of autophagy is one such strategy as this process removes intracellular damage associated with many chronic diseases. In particular, we proposed that transient activation of autophagy is can provide an effective strategy for treating many diseases of aging or the aging process itself, as this process removes intracellular damage associated with many chronic diseases.

In view of this we conducted chemical screens for autophagy inducers and identified numerous coumarin scaffold compounds exhibiting autophagy induction activity.

Initially, it was contemplated that autophagy-inducing compounds would be identified for the treatment and/or prophylaxis of age-related neurodegenerative conditions such as Parkinson's Disease (PD) and Alzheimer's disease. A dominant hypothesis for both of these disorders has centered on the accumulation of neurotoxic protein species (Aβ, tau, and alpha-synuclein) and damaged mitochondria. We have previously demonstrated that chemically engaging endogenous repair processes is protective in mouse PD models. Enhancement of autophagy, which removes both neurotoxic protein aggregates and damaged mitochondria ("mitophagy") is one such mechanism.

We conducted a chemical screen in a neuronal cell line for chemical compounds that induce a master positive regulator of autophagy and lysosomal function, transcription factor EB (TFEB). Hit compounds were then tested across a wide range of disease models in the nematode *C. elegans*, in an in vitro human neuronal tauopathy model, and in an age-related mouse model of PD. It was discovered that one coumarin derivative, 2,3,6,7,10,11-Hexahydro-1H,5H-cyclopenta(3,4)(1)benzopyrano(6,7,8-ij)quinolizin-12(9H)-one (Coumarin 106; CAS Registry No. 41175-45-5) (also referred to herein as "C1") prevents neurotoxic protein accumulation and enhances mitochondrial function by transiently inducing autophagy including mitophagy. It is believed that this compound engages a novel target for neurological disease to enhance TFEB activity that transiently induces autophagy.

Figure 2:
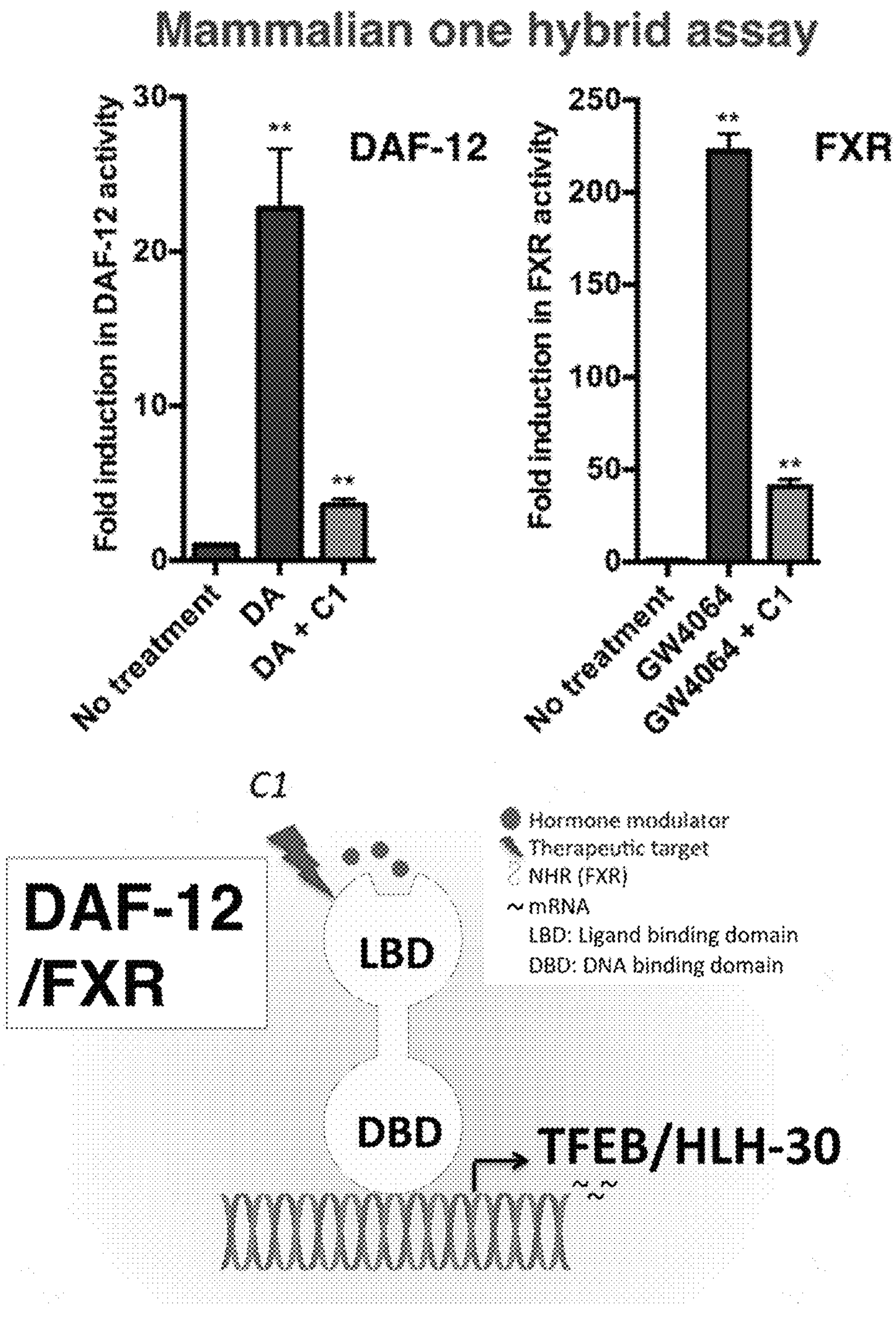
FIG. 2 shows that C1 (AIC106) inhibits DAF-12/FXR activity.
Figure 3:
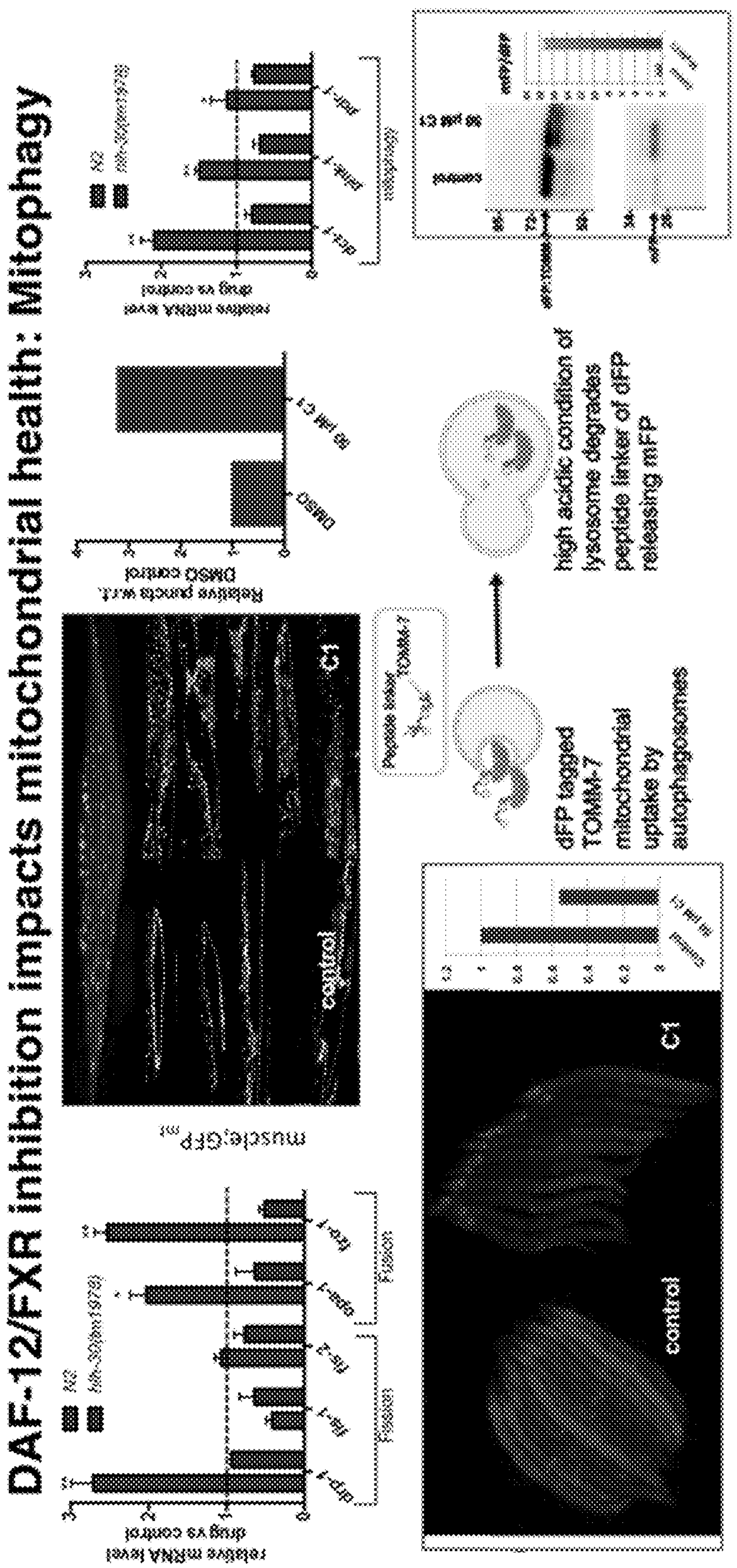
FIG. 3 shows that C1 (AIC106) mediated inhibition of DAF-12/FXR impacts mitochondrial health by increasing mitophagy.
Figure 4:
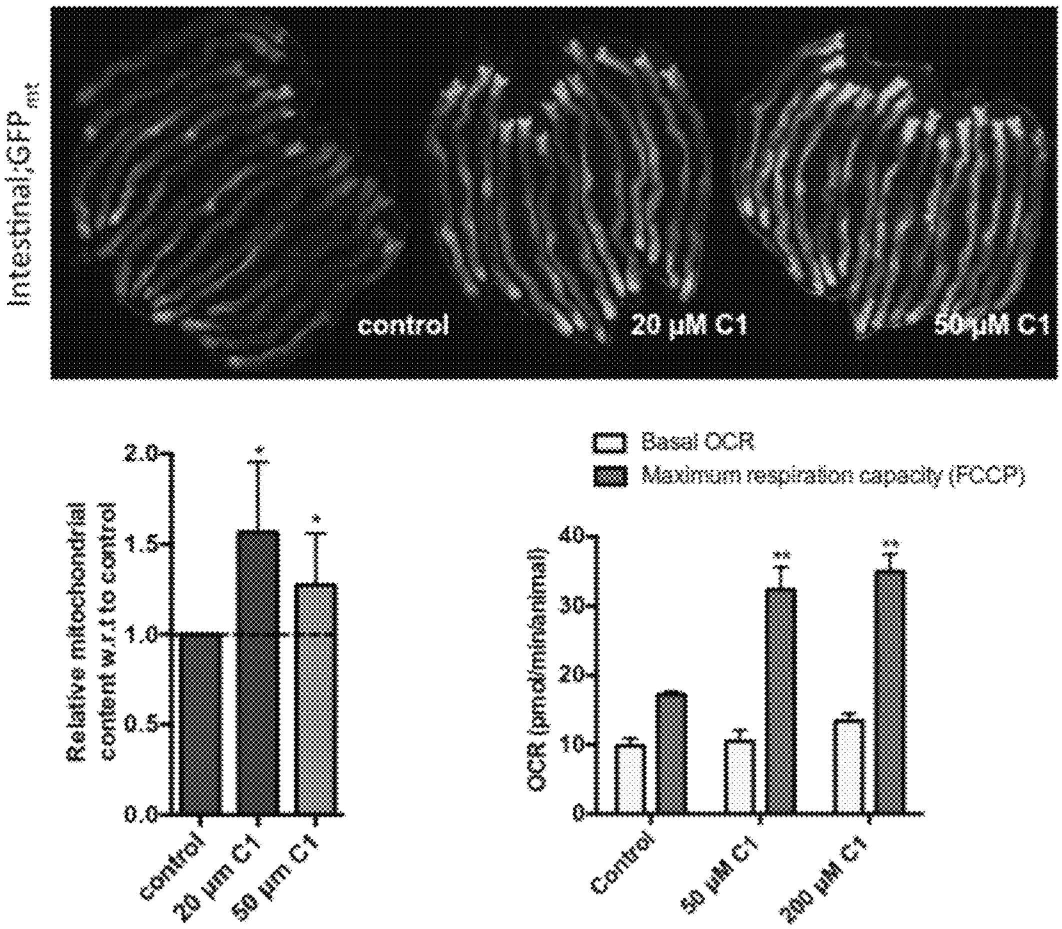
FIG. 4 shows that C1 (AIC106) mediated inhibition of DAF-12/FXR increases mitobiogenesis.
Figure 5:
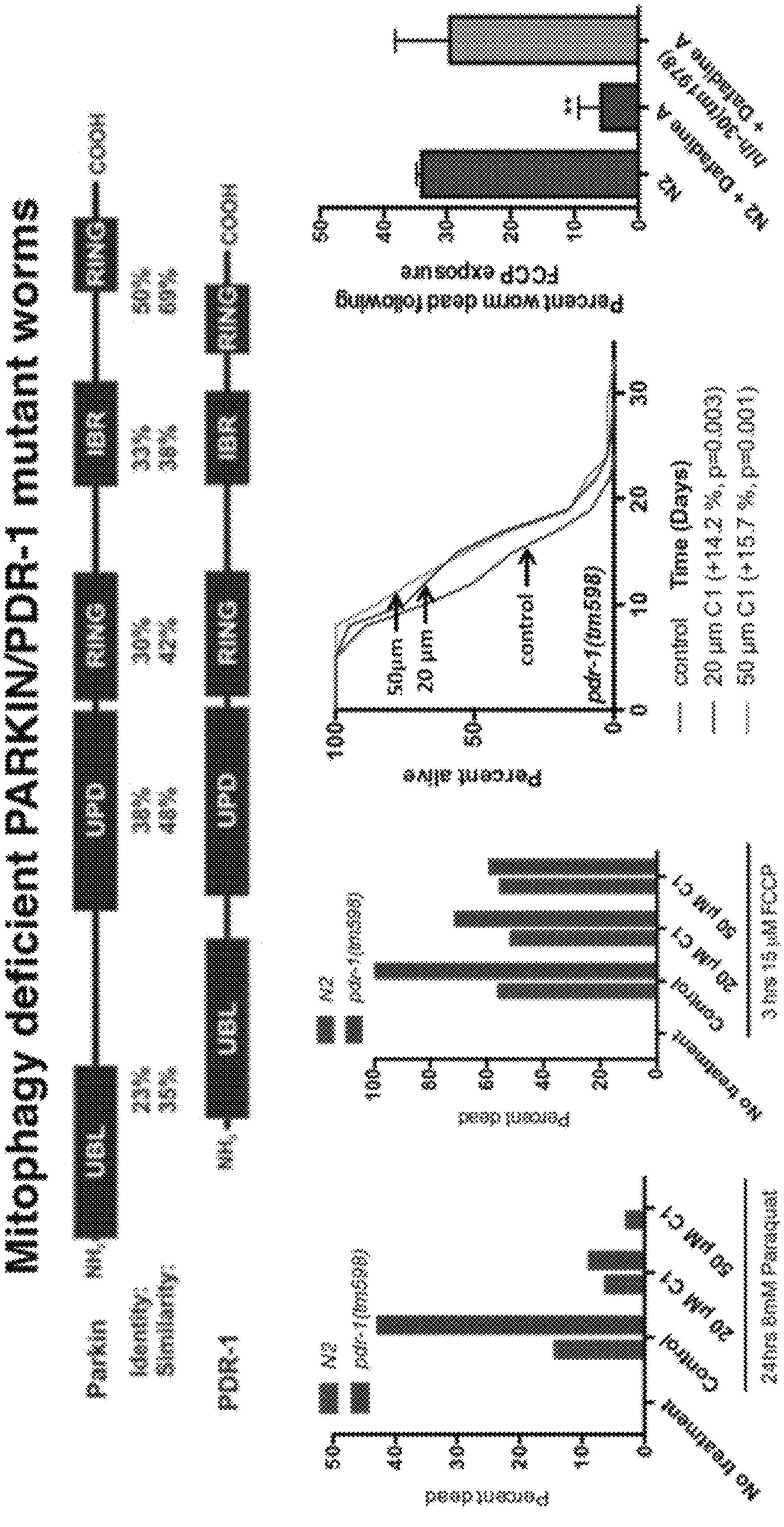
FIG. 5 shows that C1 (AIC106) can rescue mitophagy deficient PARKIN/PDR-1 mutant worms.

In particular, without being bound to a particular theory, it is believed that C1 induces TFEB by modulating FXR activity. It appears that C1 acts as an FXR antagonist that results in up-regulation of the worm TFEB homologue HLH-30 resulting in increased autophagic function and removal of damaged mitochondria and proteotoxic species. In this regard, it was demonstrated, for example, that C1 inhibits DAF-12FXR activity (see, e.g., FIG. 2). C1 is capable of increasing mitophagy (see, e.g. FIG. 3), increase mitobiogenesis (see, e.g., FIG. 4) and is capable of rescuing mitophagy deficient PRKIN/PDR-1 mutant worms.

In view of this and the additional data presented in Example 1, it is believed that C1 is an effective master positive regulator of autophagy and lysosomal function, transcription factor EB (TFEB).

In view of these data, is believe that C1 can be effectively used in the treatment and/or prophylaxis of age-related disorders such as Alzheimer's disease, Parkinson's disease, age-related mild cognitive impairment (MCI), and the like.

Moreover, in addition to targeting neurological disorders, induction of autophagy is protective in other disease states. For example, over-expression of TFEB in a mouse model of hepatic disease caused by alpha-1-anti-trypsin (AAT) deficiency prevents toxic protein accumulation (ATZ, a mutant form of AAT) and promotes liver health. ATT deficiency is a childhood disease with no cure other than liver transplantation. Although this is not an age-related disease, it shares with aging a critical loss in protein homeostasis and provides a rapid assay of compound efficacy.

Compounds that Promote Autophagy

As noted above, coumarin 106 (also designated C1 herein) was identified as a compound that effectively induces or promotes autophagy. Without being bound by a particular theory, it is believed the coumarin induces TFEB by modulating FXR activity. It appears that C1 acts as an FXR antagonist that results in up-regulation of the worm TFEB homologue HLH-30 resulting in increased autophagic function and removal of damaged mitochondria and proteotoxic species.

Figure 1:
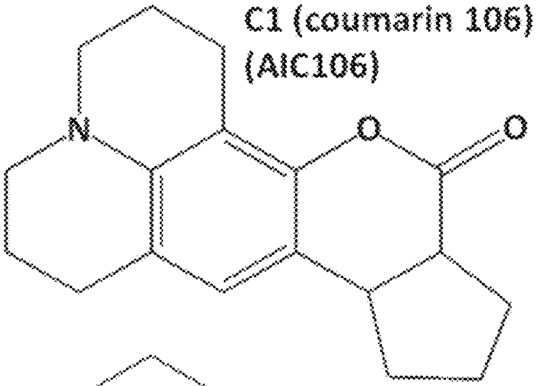
FIG. 1 illustrates the structure of C1 coumarin 106 (AIC106) and other compounds described herein that promote autophagy.
Figure 1:
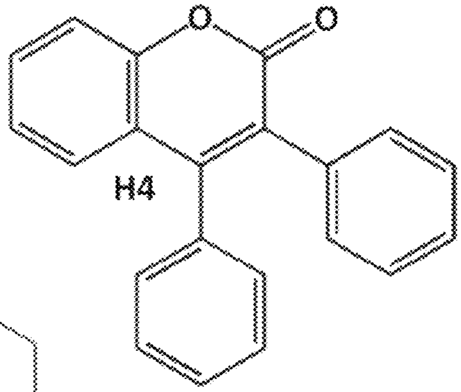
Figure 1:
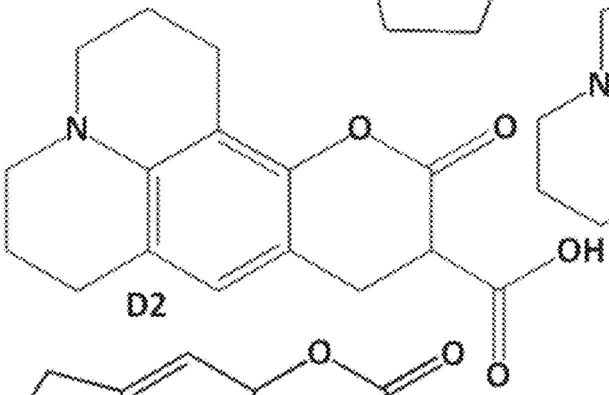
Figure 1:
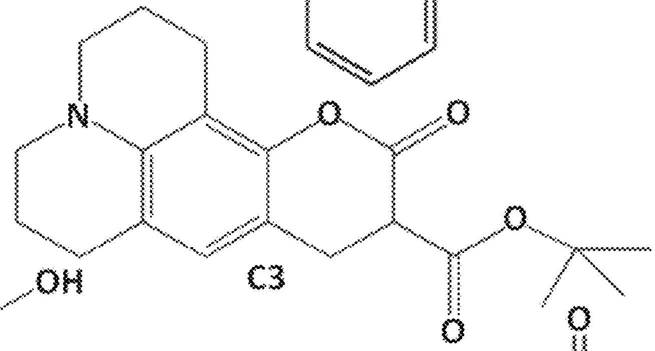
Figure 1:
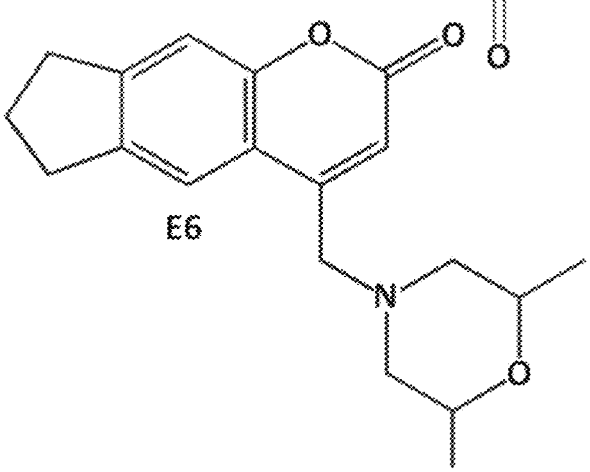
Figure 1:
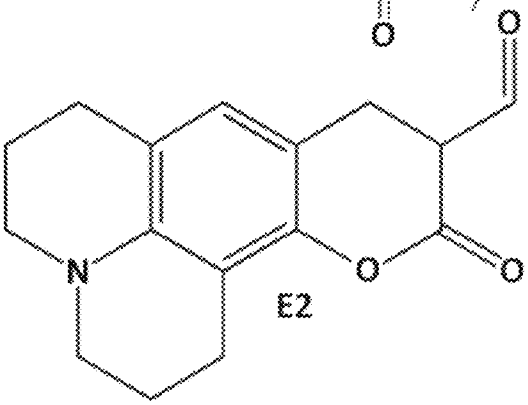

It was discovered that small structural alterations in the C1 compound can have significant effects on the degree of TFEB activation (see, e.g., FIG. 17) the screening systems described herein identified a number of structures related to C1 that similarly induce TFEB. Such compounds include but are not limited to C1 and the other compounds shown in Table 1 (see, also, FIG. 1).

TABLE 1

C1 and other compounds that activate TFEB.

| Cmpd./ ID # | % activation/ Control 24 hrs 48 hrs | Structure |
|---|---|---|
| C1 ST083674 | 350.83 413.96 | 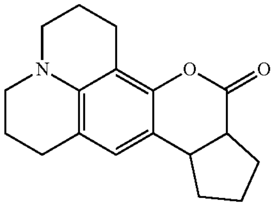 [SMILES: O=C1Oc2c(cc3c4c2CCCN4CCC3)C2CCCC12] |
| C3 ST081388 | 316.91 382.31 | 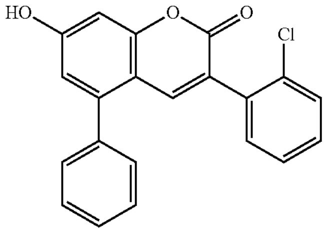 [SMILES: O=c1oc2cc(O)cc(-c3ccccc3)c2cc1-c1ccccc1Cl] |
| H2 ST079566 | 333.53 393.36 | 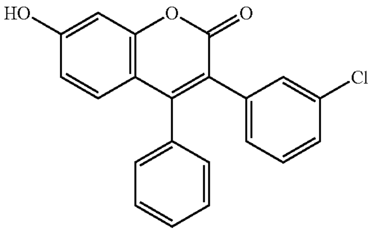 [SMILES: O=c1oc2cc(O)ccc2c(-c2ccccc2)c1-c1cccc(Cl)c1] |

TABLE 1-continued

C1 and other compounds that activate TFEB.

| Cmpd./ ID # | % activation/ Control 24 hrs 48 hrs | Structure |
|---|---|---|
| F2 ST079564 | 340.84 368.09 | 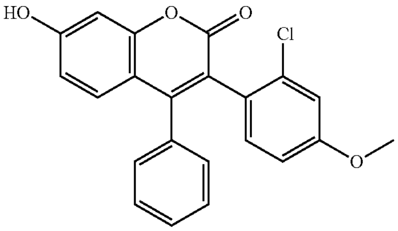 [SMILES: COc1ccc(-c2c(-c3ccccc3)c3ccc(O)cc3oc2=O)c(Cl)c1] |
| D3 ST085906 | 380.51 390.83 | 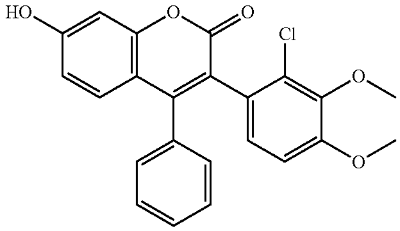 [SMILES: COc1ccc(-c2c(-c3ccccc3)c3ccc(O)cc3oc2=O)c(Cl)c1OC] |
| G2 ST079565 | 341.49 418.42 | 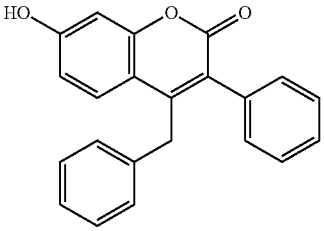 [SMILES: O=c1oc2cc(O)ccc2c(Cc2ccccc2)c1-c1ccccc1] |
| A3 ST079567 | 323.60 368.56 | 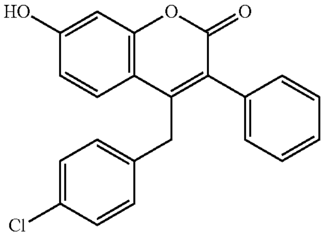 [SMILES: O=c1oc2cc(O)ccc2c(Cc2ccc(Cl)cc2)c1-c1ccccc1] |
| C2 ST058434 | 311.20 366.86 | 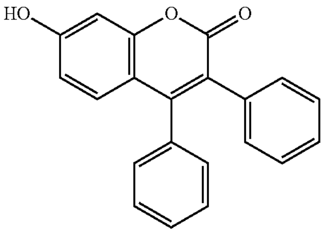 [SMILES: O=c1oc2cc(O)ccc2c(-c2ccccc2)c1-c1ccccc1] |
| A2 ST009474 | 293.09 306.93 | 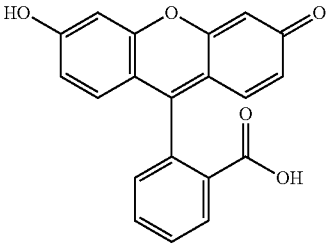 [SMILES: O=C(O)c1ccccc1-c1c2ccc(=O)cc-2oc2cc(O)ccc12] |

TABLE 1-continued
C1 and other compounds that activate TFEB.
| Cmpd./ ID # | % activation/ Control 24 hrs 48 hrs | Structure |
|---|---|---|
| A5 ST098977 | 62.32 64.73 | 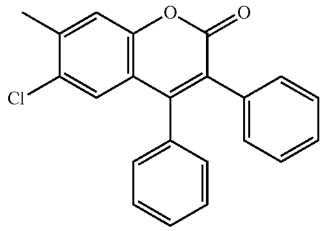 [SMILES: Cc1cc2oc(=O)c(-c3ccccc3)c(-c3ccccc3)c2cc1Cl] |
| D5 ST098990 | 102.95 115.05 | 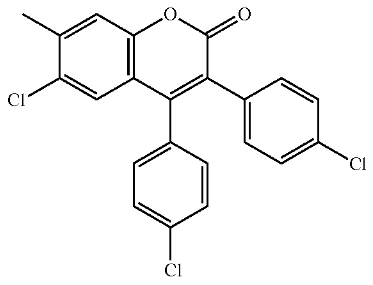 [SMILES: Cc1cc2oc(=O)c(-c3ccc(Cl)cc3)c(-c3ccc(Cl)cc3)c2cc1Cl] |
| A6 ST099012 | 76.64 77.71 | 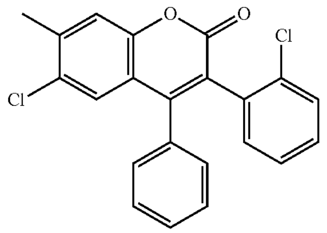 [SMILES: Cc1cc2oc(=O)c(-c3ccccc3Cl)c(-c3ccccc3)c2cc1Cl] |
| A4 ST098958 | 361.32 314.48 | 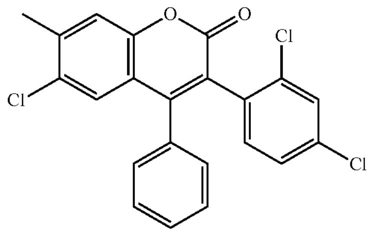 [SMILES: Cc1cc2oc(=O)c(-c3ccc(Cl)cc3Cl)c(-c3ccccc3)c2cc1Cl] |
| D6 ST099021 | 359.98 412.99 | 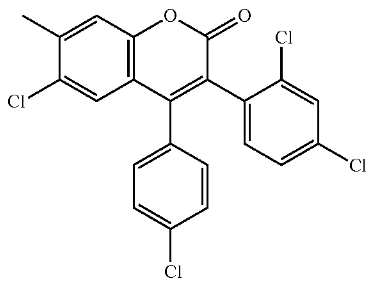 [SMILES: Cc1cc2oc(=O)c(-c3ccc(Cl)cc3Cl)c(-c3ccc(Cl)cc3)c2cc1Cl] |
TABLE 1-continued
C1 and other compounds that activate TFEB.
| Cmpd./ ID # | % activation/ Control 24 hrs 48 hrs | Structure |
|---|---|---|
| H5 ST099008 | 70.13 75.00 | 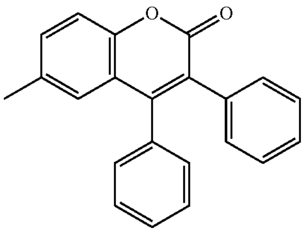 [SMILES: Cc1ccc2oc(=O)c(-c3ccccc3)c(-c3ccccc3)c2c1] |
| B6 ST099016 | 91.23 90.64 | 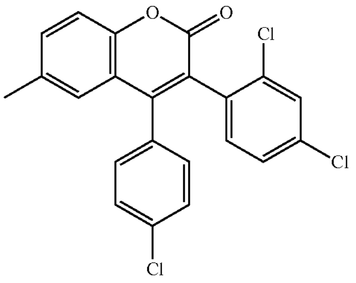 [SMILES: Cc1ccc2oc(=O)c(-c3ccc(Cl)cc3Cl)c(-c3ccc(Cl)cc3)c2c1] |
| C5 ST098984 | 87.23 92.03 | 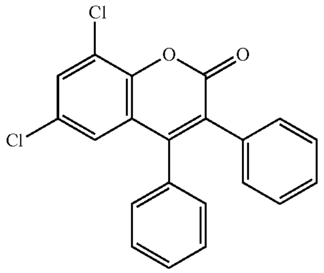 [SMILES: O=c1oc2c(Cl)cc(Cl)cc2c(-c2ccccc2)c1-c1ccccc1] |
| F5 ST098997 | 105.27 107.50 | 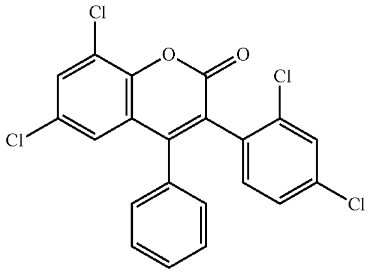 [SMILES: O=c1oc2c(Cl)cc(Cl)cc2c(-c2ccccc2)c1-c1ccc(Cl)cc1Cl] |
| C6 ST099019 | 104.37 122.46 | 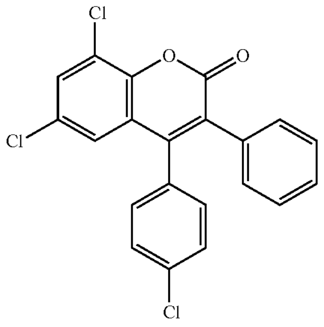 [SMILES: O=c1oc2c(Cl)cc(Cl)cc2c(-c2ccc(Cl)cc2)c1-c1ccccc1] |

TABLE 1-continued
C1 and other compounds that activate TFEB.
| Cmpd./ ID # | % activation/ Control 24 hrs 48 hrs | Structure |
| --- | --- | --- |
| D4 ST098963 | 368.68 364.48 | 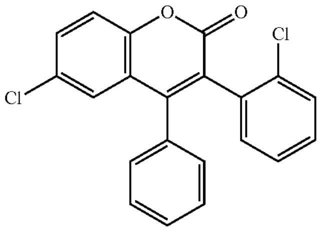 [SMILES: O=c1oc2ccc(Cl)cc2c(-c2ccccc2)c1-c1ccccc1Cl] |
| B5 ST098981 | 83.15 84.08 | 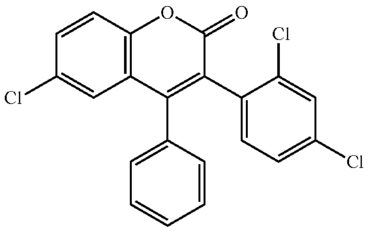 [SMILES: O=c1oc2ccc(Cl)cc2c(-c2ccccc2)c1-c1ccc(Cl)cc1Cl] |
| H3 ST098952 | 360.71 415.28 | 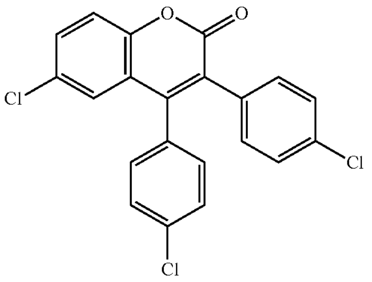 [SMILES: O=c1oc2ccc(Cl)cc2c(-c2ccc(Cl)cc2)c1-c1ccc(Cl)cc1] |
| B3 ST081387 | 337.52 371.81 | 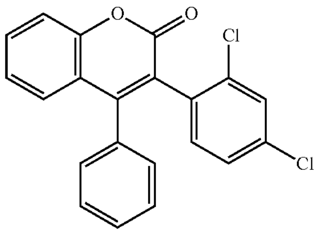 [SMILES: O=c1oc2ccccc2c(-c2ccccc2)c1-c1ccc(Cl)cc1Cl] |
| G5 ST099003 | 65.12 78.40 | 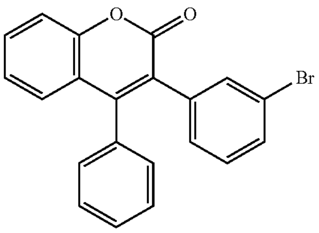 [SMILES: O=c1oc2ccccc2c(-c2ccccc2)c1-c1cccc(Br)c1] |
| E5 ST098996 | 92.48 110.20 | 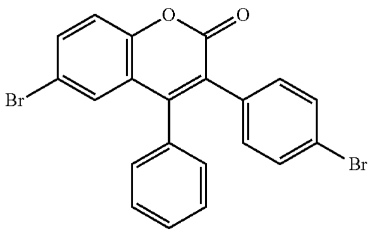 [SMILES: O=c1oc2ccc(Br)cc2c(-c2ccccc2)c1-c1ccc(Br)cc1] |
TABLE 1-continued
C1 and other compounds that activate TFEB.
| Cmpd./ ID # | % activation/ Control 24 hrs 48 hrs | Structure |
| --- | --- | --- |
| B4 ST098960 | 390.04 367.49 | 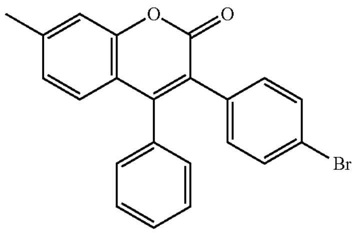 [SMILES: Cc1ccc2c(-c3ccccc3)c(-c3ccc(Br)cc3)c(=O)oc2c1] |
| E4 ST098970 | 399.82 350.34 | 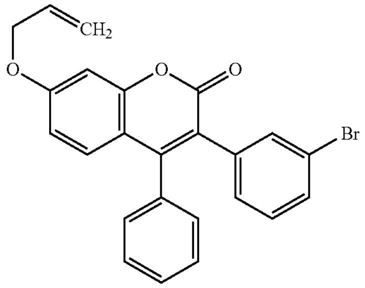 [SMILES: C=CCOc1ccc2c(-c3ccccc3)c(-c3cccc(Br)c3)c(=O)oc2c1] |
| G4 ST098972 | 390.30 397.86 | 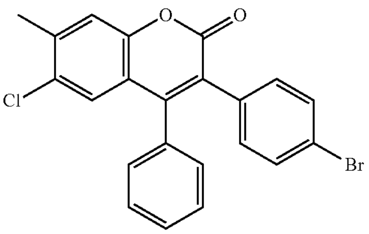 [SMILES: Cc1cc2oc(=O)c(-c3ccc(Br)cc3)c(-c3ccccc3)c2cc1Cl] |
| F4 ST098971 | 364.76 371.44 | 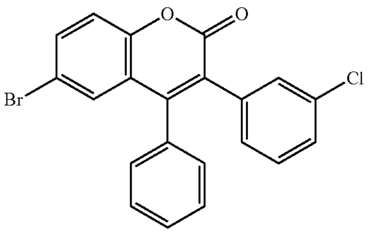 [SMILES: O=c1oc2ccc(Br)cc2c(-c2ccccc2)c1-c1cccc(Cl)c1] |
| E3 ST098947 | 346.57 389.15 | 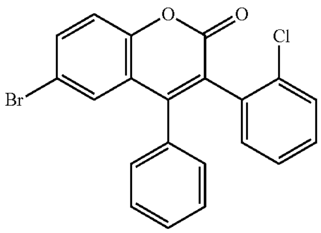 |

TABLE 1-continued

| Cmpd./ ID # | % activation/ Control 24 hrs 48 hrs | Structure |
|---|---|---|
| C1 and other compounds that activate TFEB. | | |
| B2 ST058410 | 330.90 361.44 | 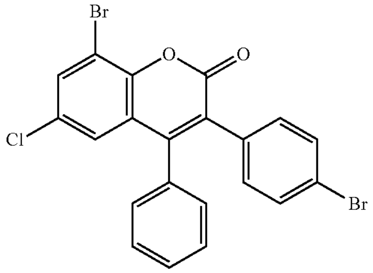 [SMILES: O=c1oc2c(Br)cc(Cl)cc2c(-c2ccccc2)c1-c1ccc(Br)cc1] |
| G3 ST098951 | 364.98 439.04 | 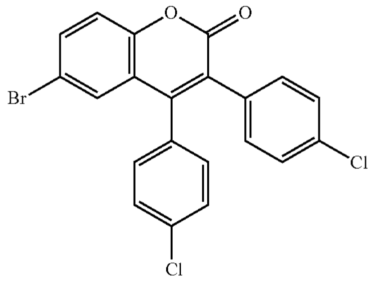 |
| F3 ST098949 | 302.47 364.86 | 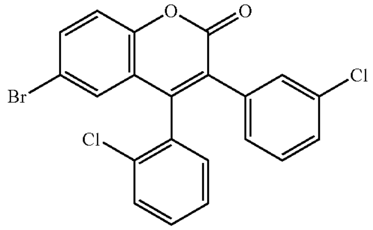 [SMILES: O=c1oc2ccc(Br)cc2c(-c2ccccc2Cl)c1-c1cccc(Cl)c1] |
| C4 ST098961 | 431.92 342.88 | 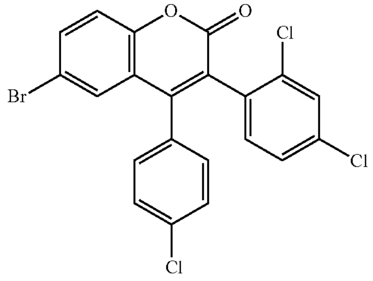 |
| H4 ST098974 | 345.96 346.51 | 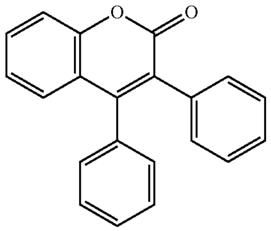 [SMILES: O=c1oc2ccccc2c(-c2ccccc2)c1-c1ccccc1] |

TABLE 1-continued

| Cmpd./ ID # | % activation/ Control 24 hrs 48 hrs | Structure |
|---|---|---|
| C1 and other compounds that activate TFEB. | | |
| D2 ST069309 | 336.28 452.77 | 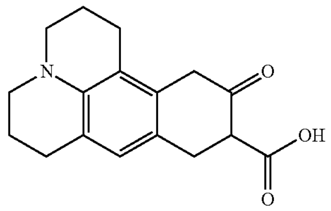 [SMILES: O=C(O)C1Cc2cc3c4c(c2CC1=O)CCCN4CCC3] |
| C3 ST083673 | 327.69 368.17 | 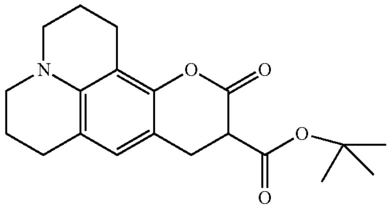 [SMILES: CC(C)(C)OC(=O)C1Cc2cc3c4c(c2OC1=O)CCCN4CCC3] |
| E2 ST074407 | 3133.88 298.89 | 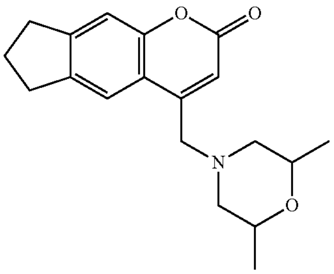 [SMILES: CC1CN(Cc2cc(=O)oc3cc4c(cc23)CCC4)CC(C)O1] |
| E6 ST107010 | 366.64 377.70 | 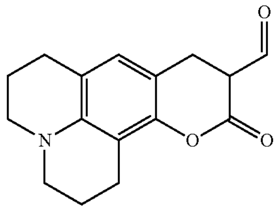 [SMILES: O=CC1Cc2cc3c4c(c2OC1=O)CCCN4CCC3] |

It will be recognized that in various embodiments substantially pure R-enantiomers or substantially pure S-enantiomers of any of these compounds are contemplated as well as various salts, solvates, clathrates, and the like of any of these compounds.

The foregoing compounds are illustrative and non-limiting. Using the teaching provided herein numerous other promoters of autophagy will be available to one of skill in the art.

Uses of Compounds that Promote Autophagy.

More generally, it is believed that C1 can be used to induce transient activation of autophagy and such activation can be used in the treatment and/or prophylaxis of a number of disease states, especially disease states that are characteristic of aging processes. As noted above, such disease states include, but are not limited to Alzheimer's disease, dementia and mild cognitive impairment (MCI), Parkinson's disease, chronic obstructive pulmonary disease (COPD), depression, heart failure, liver failure, chronic kidney disease (CKD), diabetes and metabolic syndrome, ischemic heart disease, arthritis, hypertension, cancer, Huntington's disease, and the like.

Accordingly in certain embodiment methods of promoting autophagy in cells are provided where the methods involve contacting the cells with an effective amount of a composition comprising one or more coumarin compounds that are effective to induce autophagy as described herein. In certain embodiments the cells are in vivo in a mammal (e.g., a human or a non-human mammal) and the method involves administering an effective amount of the one or more compounds to the mammal.

In certain embodiments methods for the treatment or prophylaxis of a disease or condition that responds favorably to promotion of autophagy are also provided where the method involves administering to a subject having or at risk of the disease or condition an effective amount of a composition comprising one or more compounds that are effective to induce autophagy as described herein.

Neurodegenerative Conditions.

In certain embodiments the disease or condition is an age-related neurodegenerative condition (e.g., Parkinson's disease, Alzheimer's disease, mild cognitive impairment (MCI), age-related dementia, etc.). In certain embodiments, the neurodegenerative disease comprises a disease selected from the group consisting of Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), MELAS—Mitochondrial Encephalopathy, Lactic Acidosis and Stroke, Multiple System Atrophy, Multiple sclerosis, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Spinocerebellar ataxia (multiple types with varying characteristics), Spinal muscular atrophy, Steele-Richardson-Olszewski disease, Tabes dorsalis, Tay-Sachs Disease, and Toxic encephalopathy.

Parkinson's Disease

As noted above, in certain embodiments, the compounds that induce and/or promote autophagy described herein (e.g., C1) can be used in the treatment and/or prophylaxis of Parkinson's disease (PD). Various illustrative, but non-limiting symptoms of PD are shown in Table 2.

TABLE 2

Illustrative symptoms associated with Parkinson's Disease.

| | |
|---|---|
| Tremor: | Can occur at rest, in the hands, limbs, or can be postural |
| Muscular: | Stiff muscles, difficulty standing, difficulty walking, difficulty with bodily movements, involuntary movements, muscle rigidity, problems with coordination, rhythmic muscle contractions, slow bodily movement, or slow shuffling gait |
| Sleep: | Daytime sleepiness, early awakening, nightmares, restless sleep, or sleep disturbances |
| Whole body: | Fatigue, dizziness, poor balance, or restlessness |
| Cognitive: | Amnesia, confusion in the evening hours, dementia, or difficulty thinking and understanding |
| Speech: | Impaired voice, soft speech, or voice box spasms |
| Mood: | Anxiety or apathy |
| Nasal: | Distorted sense of smell or loss of smell |
| Urinary: | Dribbling of urine or leaking of urine |
| Facial: | Jaw stiffness or reduced facial expression |
| Also common: | Blank stare, constipation, depression, difficulty swallowing, drooling, falling, fear of falling, loss in contrast sensitivity, neck tightness, small handwriting, trembling, unintentional writhing, or weight loss |

In certain prophylactic methods, the autophagy-promoting compounds described herein (e.g., C1) are administered in a prophylactically effective dose that is sufficient to prevent and/or slow the onset of one or more of the symptoms shown in Table 2.

In certain therapeutic methods, the autophagy-promoting compounds described herein (e.g., C1) are administered in a therapeutically effective dose that is sufficient to ameliorate and/or to eliminate one or more of the symptoms shown in Table 2.

Age-Related Dementia, and/or Alzheimer's Disease, and/or Mild Cognitive Impairment (MCI)

It is also believed the autophagy-promoting compounds described herein (e.g., C1) can be used in the prophylaxis and/or treatment of age-related dementia, and/or Alzheimer's disease, and/or mild cognitive impairment (MCI). Typically the methods involve administering one or autophagy-promoting compounds described herein to a subject (e.g., to a human in need thereof) in an amount sufficient to realize the desired therapeutic or prophylactic result.

In certain embodiments the autophagy-promoting compounds described herein (e.g., C1) are utilized in various prophylactic contexts. Thus, for example, in certain embodiments, the autophagy-promoting compound(s)) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. In certain embodiments, the subjects are asymptomatic. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et al. (2011) *Alzheimer's & Dementia,* 1-13) at risk for progression to AD dementia to biomarker-positive individuals who are already demonstrating very subtle decline but not yet meeting standardized criteria for MCI (see, e.g., Albert et al. (2011) *Alzheimer's and Dementia,* 1-10 (doi:10.1016/j.jalz.2011.03.008).

This latter group of individuals might be classified as "not normal, not MCI" but would be can be designated "pre-symptomatic" or "pre-clinical or "asymptomatic" or "pre-manifest"). In various embodiments this continuum of pre-symptomatic AD can also encompass, but is not necessarily limited to, (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al. (2010) *Lancet Neurol.,* 9: 119-128). This biomarker model parallels proposed pathophysiological sequence of (pre-AD/AD), and is relevant to tracking the preclinical (asymptomatic) stages of AD (see, e.g., FIG. 3 in Sperling et al. (2011) *Alzheimer's & Dementia,* 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al. (2009) *Neurology,* 73: 294-301; Yaffe et al. (2011) *JAMA* 305: 261-266).

In certain embodiments the subjects suitable for the prophylactic methods contemplated herein include, but are not limited to, subjects characterized as having asymptomatic cerebral amyloidosis. In various embodiments these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments it is contemplated that there is an identifiable preplaque stage in which only soluble forms of Aβ are present. In certain embodiments it is contemplated that oligomeric forms of amyloid may be critical in the pathological cascade, and provide useful markers. In addition, early synaptic changes may be present before evidence of amyloid accumulation.

In certain embodiments the subjects suitable for the prophylactic methods contemplated herein include, but are not limited to, subjects characterized as amyloid positive with evidence of synaptic dysfunction and/or early neurodegeneration. In various embodiments these subjects have evidence of amyloid positivity and presence of one or more markers of "downstream" AD-related neuronal injury. Illustrative, but non-limiting markers of neuronal injury include, but are not limited to (1) elevated CSF tau or phospho-tau, (2) hypometabolism in an AD-like pattern (i.e., posterior cingulate, precuneus, and/or temporoparietal cortices) on FDG-PET, and (3) cortical thinning/gray matter loss in a specific anatomic distribution (i.e., lateral and medial parietal, posterior cingulate, and lateral temporal cortices) and/or hippocampal atrophy on volumetric MRI. Other markers include, but are not limited to fMRI measures of default network connectivity. In certain embodiments early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (i.e., in later stages of preclinical (asymptomatic) AD).

In certain embodiments the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.,* 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., at about 20, about 30, about 40, about 50 years of age). Usually, however, it is not necessary to begin treatment until a patient reaches at least about 40, or at least about 50, or at least about 55, or at least about 60, or at least about 65, or at least about 70 years of age.

In some embodiments, the subject exhibits symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al. (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) *Arch. Neurol.* 61(1): 59-66; and on the internet at en.wikipedia.org/wiki/Mild_cognitive_impairment—cite_note-Grundman-1). When individuals have impairments in domains other than memory it is often classified as non-amnestic single- or multiple-domain MCI and these individuals are believed to be more likely to convert to other dementias (e.g., dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) *Arch. Neurol.* 63(5): 665-72).

The diagnosis of MCI typically involves a comprehensive clinical assessment including clinical observation, neuroimaging, blood tests and neuropsychological testing. In certain embodiments diagnostic criteria for MIC include, but are not limited to those described by Albert et al. (2011) *Alzheimer's & Dementia.* 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments clinical evaluation/diagnosis of MCI involves: (1) Concern reflecting a change in cognition reported by patient or informant or clinician (i.e., historical or observed evidence of decline over time); (2) Objective evidence of Impairment in one or more cognitive domains, typically including memory (i.e., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, and medical causes of cognitive decline, are ruled out where possible. In certain embodiments, when feasible, evidence of longitudinal decline in cognition is identified. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (i.e., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (i.e., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (i.e., mutation in APP, PS1, PS2), then the development of MCI is most likely the precursor to AD dementia. The large majority of these cases develop early onset AD (i.e., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al. (2010) *Neuron,* 21: 270-281).

In certain embodiments subjects suitable for the prophylactic methods described herein include, but need not be limited to, subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF $A\beta_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Aβ accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating can be obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 3.

TABLE 3

Illustrative clinical dementia rating (CDR) table.

| | Impairment: | | | | |
|---|---|---|---|---|---|
| | None | Questionable | Mild | Moderate | Severe |
| | CDR: | | | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home<br>Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated | Only simple chores preserved; very restricted interests, poorly maintained | No significant function in home |

TABLE 3-continued

| Illustrative clinical dementia rating (CDR) table. | | | | | |
|---|---|---|---|---|---|
| | Impairment: | | | | |
| | None | Questionable | Mild | Moderate | Severe |
| | CDR: | | | | |
| | 0 | 0.5 | 1 | 2 | 3 |
| | | | hobbies and interests abandoned | | |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments administration of one or more autophagy-promoting compounds herein (e.g., C1) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al. (2004) *Arch Neurol* 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Alzheimer's Disease (AD).

In certain embodiments the autophagy-promoting compounds described herein (e.g., C1) are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 4.

TABLE 4

| Illustrative stages of Alzheimer's disease. |
|---|
| **Moderate Cognitive Decline (Mild or early stage AD)** |
| At this stage, a careful medical interview detects clear-cut deficiencies in the following areas: |
| Decreased knowledge of recent events. |
| Impaired ability to perform challenging mental arithmetic. For example, to count backward from 100 by 7s. |
| Decreased capacity to perform complex tasks, such as marketing, planning dinner for guests, or paying bills and managing finances. |
| Reduced memory of personal history. |
| The affected individual may seem subdued and withdrawn, especially in socially or mentally challenging situations. |
| **Moderately severe cognitive decline (Moderate or mid-stage Alzheimer's disease)** |
| Major gaps in memory and deficits in cognitive function emerge. Some assistance with day-to-day activities becomes essential. At this stage, individuals may: |
| Be unable during a medical interview to recall such important details as their current address, their telephone number, or the name of the college or high school from which they graduated. |
| Become confused about where they are or about the date, day of the week or season. |
| Have trouble with less challenging mental arithmetic; for example, counting backward from 40 by 4s or from 20 by 2s. |
| Need help choosing proper clothing for the season or the occasion. |
| Usually retain substantial knowledge about themselves and know their own name and the names of their spouse or children. |
| Usually require no assistance with eating or using the toilet. |
| **Severe cognitive decline (Moderately severe or mid-stage Alzheimer's disease)** |
| Memory difficulties continue to worsen, significant personality changes may emerge, and affected individuals need extensive help with daily activities. At this stage, individuals may: |
| Lose most awareness of recent experiences and events as well as of their surroundings. |
| Recollect their personal history imperfectly, although they generally recall their own name. |
| Occasionally forget the name of their spouse or primary caregiver but generally can distinguish familiar from unfamiliar faces. |
| Need help getting dressed properly; without supervision, may make such errors as putting pajamas over daytime clothes or shoes on wrong feet. |
| Experience disruption of their normal sleep/waking cycle. |
| Need help with handling details of toileting (flushing toilet, wiping and disposing of tissue properly). |
| Have increasing episodes of urinary or fecal incontinence. |
| Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding. |

TABLE 4-continued

| Illustrative stages of Alzheimer's disease. |
|---|
| Tend to wander and become lost. |
| **Very severe cognitive decline (Severe or late-stage Alzheimer's disease)** |
| This is the final stage of the disease when individuals lose the ability to respond to their environment, the ability to speak, and, ultimately, the ability to control movement. |
| Frequently individuals lose their capacity for recognizable speech, although words or phrases may occasionally be uttered. |
| Individuals need help with eating and toileting and there is general incontinence. |
| Individuals lose the ability to walk without assistance, then the ability to sit without support, the ability to smile, and the ability to hold their head up. Reflexes become abnormal and muscles grow rigid. Swallowing is impaired. |

In various embodiments administration of one or more the autophagy-promoting compounds described herein (e.g., C1) to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

Liver Diseases, Metabolic Syndrome, and Diabetes

In certain embodiments the disease or condition is a liver disease (e.g., SERPINA1/α1-anti-trypsin (ATT) deficiency, nonalcoholic fatty liver disease (NAFLD), alcoholic liver disease (ALD), drug-induced liver injury, ischemia/reperfusion injury, hepatitis, liver cirrhosis, and the like) and the autophagy-promoting compounds described herein (e.g., C1) are administered in a therapeutically effective or prophylactically effective dose for one or more of these conditions.

In certain embodiments the disease or condition is type II diabetes and/or metabolic syndrome and the autophagy-promoting compounds described herein (e.g., C1) are administered in a therapeutically effective or prophylactically effective dose for one or more of these conditions (e.g., to slow or stop the loss of insulin sensitivity, and/or to restore insulin sensitivity).

Lifespan and/or Healthspan

In view of the data provided herein it is also believed the autophagy-promoting compounds described herein (e.g., C1) can be effective to improve life span and/or health span, e.g., as indicated by an improvement in a measure of life span and/or health span. In various embodiments any suitable measure of life/health span can be employed in the methods described herein. In certain embodiments, an improvement in life span and/or health span can be detected as a reduction in frailty, an improvement in function in an age-related disability, the mitigation of a symptom of an age-related disease, and/or a delay in onset of frailty, age-related disability, or age-related disease, relative to the condition of the subject before administration of a compound described here or relative to a control population. For example, a reduction in frailty, an improvement in function in an age-related disability, the mitigation of a symptom of an age-related disease can be measured with reference to the pre-treatment condition of the subject or relative to a control population. Delay in onset of frailty, age-related disability, or age-related disease is typically measured with reference to a control population.

In certain embodiments, an improvement (i.e., a reduction) in frailty can be measured as increased strength, weight gain, faster mobility, increased energy, increased levels of activity, increased endurance, and/or enhanced behavioral response to a sensory cue. Alternatively, or in addition, a decrease in one or more inflammatory biomarkers, an improvement in glucose homeostasis, and a decrease in one of more biomarkers of clotting activation can indicate a reduction in frailty.

The mitigation of a symptom of an age-related disease, such as osteoporosis, arthritis, cataracts, macular degeneration, and cardiovascular disease, can also indicate an improvement in a measure of life/health span in the methods described herein. For example, one or more cardiovascular parameters, such as cholesterol level, triglyceride level, high density lipoprotein level, and/or blood pressure can be measured as an indicator of life/health span.

In particular embodiments, an improvement in a measure of life/health span can be detected as a reduction in, a reversal of, or delay in onset of sarcopenia, relative to the condition of the subject before treatment or relative to a control population. More specifically, reduction and/or reversal of sarcopenia can be measured with reference to the pre-treatment condition of the subject or relative to a control population; whereas delay in onset of sarcopenia is typically measured with reference to a control population.

In certain embodiments, an improvement in a measure of life/health span can be detected as reduction in, a reversal of, or delay in onset of an age-related increase in lipofuscin accumulation, relative to the condition of the subject before administration of a compound described herein or relative to a control population. In particular, reduction and/or reversal of sarcopenia can be measured with reference to the pre-treatment condition of the subject or relative to a control population; whereas delay in onset of excess lipofuscin is typically measured with reference to a control population. Illustrative tissues in which in which lipofuscin accumulated and can be measured include brain, heart, liver, spleen, and kidney.

Alternatively or in addition, improved life/health span can be detected by detecting an enhanced ability to maintain homeostasis during the application of a stressor and/or a reduced time required to return to homeostasis after the application of a stressor. For example, responses to stressors including drug-induced oxidative stress, exposure to heat, and exposure to cold can be measured to determine whether the subject has an enhanced ability to maintain and/or return to homeostasis after being stressed.

In particular embodiments, the measure of life/health span includes the level and/or activity of a molecule that plays a role in protein trafficking, the autophagy pathway, ubiquitination, and/or lysosomal degradation of proteins. One illustrative, but non-limiting example of the latter is lysosome-associated membrane protein-2 (LAMP-2).

Other indicators of life/health span can include but are not limited to the number of inclusion bodies in muscle tissue, and/or mitochondrial function and/or morphology.

In certain embodiments the methods described herein are typically carried out using subject who are suffering from, or determined to be at risk for, a decline in a measure of life/health span. Thus, for example, these methods can be performed on a subject suffering from, or determined to be at risk for, frailty, an age-related disability, or an age-related disease. In various embodiments, where the subject is suffering from, or determined to be at risk for, frailty, the subject is determined to have at least two, three, four, five, six, or seven symptoms selected: weakness, weight loss, slowed mobility, fatigue, low levels of activity, poor endurance, and impaired behavioral response to a sensory cue. Alternatively, or in addition, the subject may have one or more symptoms selected from an increase in one or more inflammatory biomarkers, glucose homeostasis impairment, and an increase in one of more biomarkers of clotting activation.

In particular illustrative embodiments, the subject can be a subject suffering from sarcopenia and/or that has lipofuscin accumulation in one or more of brain, heart, liver, spleen, and kidney. Alternatively, or in addition, the subject may have a reduced ability to maintain homeostasis during the application of a stressor and/or may require an extended time required to return to homeostasis after the application of a stressor. In such embodiments, the reduced ability or extended time is relative to the condition of the subject at a previous time or relative to a normal ability or time.

In certain particular, but non-limiting embodiments, the subject may display an abnormal level and/or activity of a molecule that plays a role in protein trafficking, the autophagy pathway, ubiquitination, and/or lysosomal degradation of proteins (e.g., LAMP-2). Alternatively, or in addition, the subject may have abnormal inclusion bodies in muscle tissue and/or an abnormality in mitochondrial function and/or morphology. Such changes may be observed relative to the condition of the subject at a previous time or relative to a normal (e.g., non-aged adult) subject.

Pharmaceutical and/or Dietary Formulations.

In certain embodiments the compounds described herein that promote autophagy (e.g., C1) may be formulated into a medicament or a dietary supplement by mixing with a dietetically or pharmaceutically acceptable carrier or excipient. Such a carrier or excipient may comprise, but is not limited to, a solvent, dispersion medium, coating, isotonic or absorption delaying agent, sweetener or the like. These include any and all solvents, dispersion media, coatings, isotonic and absorption delaying agents, sweeteners and the like. Suitable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular dosage form. The use of such media and agents for pharmaceutically active substances is well known in the art.

The compounds described herein that promote autophagy (e.g., C1) can be administered in the "native" form or, if desired, in the form of salts, esters, amides, derivatives, and the like, provided the salt, ester, amide, or derivative is suitable pharmacologically, e.g., effective in the present method(s). Salts, esters, amides, and other derivatives of the compounds described herein that promote autophagy (e.g., C1) can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt (e.g., such as a carboxylic acid functionality of the compounds described herein). A pharmaceutically acceptable salt is any salt that retains the activity of the parent compound and does not impart any deleterious or untoward effect on the subject to which it is administered and in the context in which it is administered.

Methods of pharmaceutically formulating the compounds described herein (e.g., C1) as salts, esters, amides, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the compounds described herein can include halide salts, such as may be prepared using hydrochloric or hydrobromic acids. Conversely, preparation of basic salts of the compounds described herein can be prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, formate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent (e.g., C1, and other autophagy-promoting compounds described herein). In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the compounds identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agent(s) described herein (e.g., C1, and other autophagy-promoting compounds described herein) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the compounds described herein. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the C1 or other autophagy-promoting compounds described herein, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., C1, and other autophagy-promoting compounds described herein) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the autophagy-promoting compounds described herein and on the particular physio-chemical characteristics of the compound(s).

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the autophagy-promoting compounds described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the autophagy-promoting compounds into preparations that can be used pharmaceutically. Proper formulation is dependent upon the route of administration chosen.

Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the autophagy-promoting compound(s) described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the autophagy-promoting compound(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the autophagy-promoting compound(s) with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the autophagy-promoting compound(s) described herein are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the autophagy-promoting compound(s) described herein can be formulated in rectal or vaginal compositions such as suppositories or retention enemas, e.g., containing conventional suppository bases such as cocoa butter or other glycerides.

In addition to the formulations described previously, the autophagy-promoting compound(s) described herein may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the autophagy-promoting compound(s) described herein and/or formulations thereof are administered orally. This is readily accomplished by the use of tablets, caplets, lozenges, liquids, and the like.

In certain embodiments, the autophagy-promoting compound(s) and/or formulations described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the compound(s) and/or formulations described herein are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the autophagy-promoting compound(s) and any other materials that are present.

In certain embodiments, one or more autophagy-promoting compound(s) described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the autophagy-promoting compound(s) described herein are suitable for oral administration. In various embodiments, the compound(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the autophagy-promoting compound(s) described herein in an effective amount to achieve a pharmacological effect or therapeutic improvement without undue adverse side effects. Illustrative pharmacological effects or therapeutic improvements include, but are not limited to, upregulation of autophagy, amelioriation of one or more symptoms of a pathology that responds favorably to upregulation of autophagy, slowing or stopping of the progression of a pathology that responds favorably to upregulation of autophagy, improvement in one or more indicators of lifespan and/or healthspan, and the like.

In various embodiments, the typical daily dose of autophagy-promoting compound(s) described herein varies and will depend on various factors such as the individual requirements of the patients and the disease to be diagnosed and/or treated. In general, the daily dose of compounds can be in the range of 1-1,000 mg or 1-800 mg, or 1-600 mg, or 1-500 mg, or 1-400 mg. In one illustrative embodiment a standard approximate amount of the autophagy-promoting compound(s) described above present in the composition can be typically about 1 to 1,000 mg, or about 5 to 500 mg, or about 10 to 100 mg. In certain embodiments the probes are administered only once, or for follow-up as required. In certain embodiments the autophagy-promoting compound (s) and/or formulations thereof are administered once a day, in certain embodiments, administered twice a day, in certain embodiments, administered 3 times/day, and in certain embodiments, administered 4, or 6, or 6 or 7, or 8 times/day.

In certain embodiments the autophagy-promoting compound(s) described herein are formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the autophagy-promoting compound(s) described herein are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the autophagy-promoting compound(s) described herein may be formulated in a single liquid dosage form such as suspension containing all active ingredients or dry suspension to be reconstituted prior to use.

In certain embodiments, the autophagy-promoting compound(s) described herein are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the autophagy-promoting compound(s) described herein and formulations thereof and methods of use thereof are described herein with respect to use in humans, they are also suitable for animal, e.g., veterinary use. Thus, certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Kits.

In various embodiments, the autophagy-promoting compound(s) described herein and/or formulations thereof described herein thereof can be enclosed in multiple or single dose containers. The enclosed agent(s) can be provided in kits, for example, including component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments, a kit is provided where the kit comprises one or more autophagy-promoting compound(s) described herein and/or formulations/compositions thereof, or pharmaceutically acceptable salt or solvate of the autophagy-promoting compound(s) preferably provided as a pharmaceutical composition and in a suitable container or containers and/or with suitable packaging; optionally one or more additional active agents, which if present are preferably provided as a pharmaceutical composition and in a suitable container or containers and/or with suitable packaging; and optionally instructions for use, for example written instructions on how to administer the compound or compositions for the induction and/or promotion of autophagy.

As with any pharmaceutical product, the packaging material(s) and/or container(s) are designed to protect the stability of the product during storage and shipment. In addition, the kits can include instructions for use or other informational material that can advise the user such as, for example, a physician, technician or patient, regarding how to properly administer the composition(s) as prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign protein is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal angioedema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Experiments & Results

Figure 6:
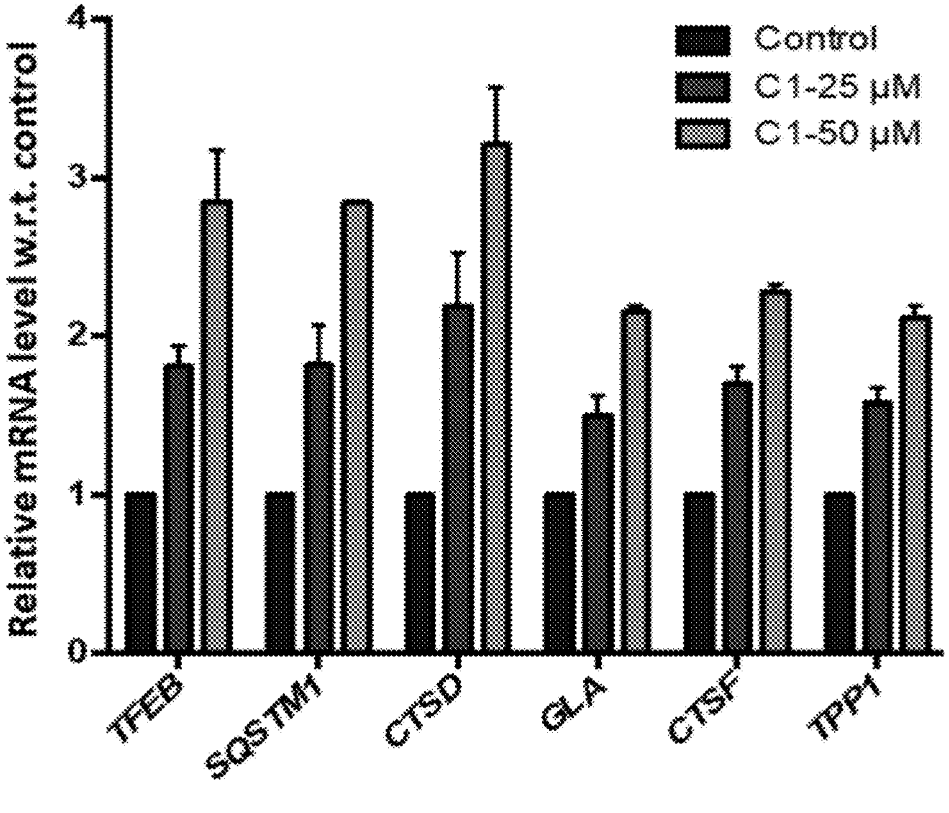
FIG. 6 illustrates that coumarin 106 (“C1”, “AIC106”) significantly up-regulates TFEB in differentiated human neuronal cells. Relative expression of TFEB and downstream target genes as assessed by qPCR from mRNA extracted from differentiated SY5Y cells treated with C1 (AIC106) versus vehicle-treated controls. Values represent fold induction versus controls, *$p<0.01$. Run in triplicate in 3 independent experiments.
Figure 7:
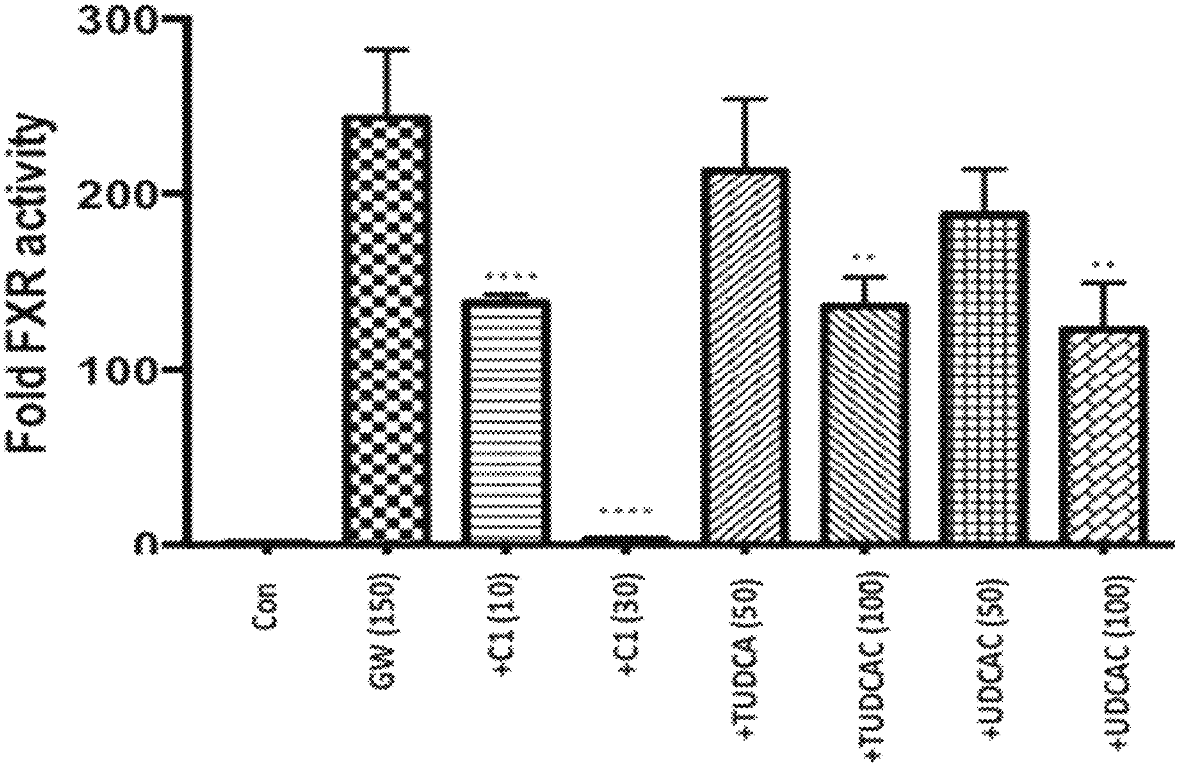
FIG. 7 illustrates that coumarin 106 (“C1”, “AIC106”) acts as a potent FXR antagonist. The ability of C1 (AIC106) (10 μM and 30 μM) to inhibit activation of the FXR agonist GW4164 (GW, 150 μM) was interrogated using a commercially available kit (Indigo Biosciences) versus the established natural FXR ligands TUDCA and UDCA (50 μM and 100 μM). Values are fold induction versus untreated controls; **$p<0.01$ versus GW; $p<0.05$ versus GW.

In vitro drug screening studies. Based on results from our recently published study demonstrating neuroprotection elicited by rapamycin in a mouse model of Parkinson's disease (PD) was dependent upon TFEB up-regulation, we carried out a small molecular screen to identify novel TFEB-inducing agents. We utilized for these studies a 3000 compound natural product derivative library (Timtec, Newark, DE) in differentiated human neuronal SY5Y cells transfected with a sensitive TFEB promotor-Gaussian luciferase construct. The lead compound identified in this screen, C1, was subsequently shown to elicit significant dose-dependent elevations in TFEB expression as well as up-regulation of several downstream TFEB target genes in these same cells (FIG. 6). C1 is a coumarin-related compound, part of a family of natural benzopyrones found in many edible plants. This family of compounds is orally available, demonstrate low toxicity, and good BBB permeability. The compound displaying several favorable characteristics as a potential CNS-acting drug including lack of rotatable bonds, a polar surface area (PSA) of 29.5 A^2, a C Log P of 4.48, lack of hydrogen bond donor sites (low p-glycoprotein affinity), and a tertiary nitrogen. Based on its structure, we noted that C1 appeared to share similarities with known FXR antagonists; preliminary ChemMine studies predicted a compound docking site within the nuclear hormone receptor. Subsequent human cell-based analyses showed that C1 significantly inhibited FXR activation elicited by the FXR agonist GW4614, superior to the effects of natural FXR antagonists (FIG. 7).

Figure 8A:
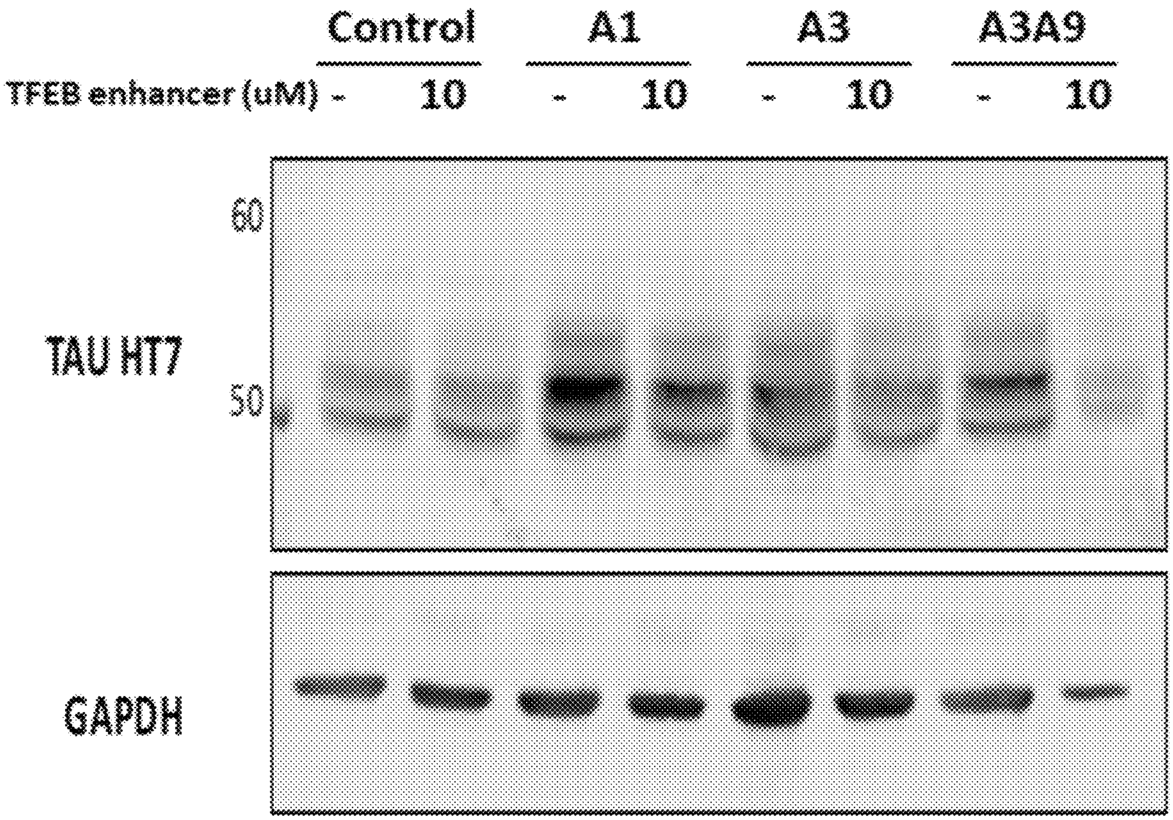
FIGS. 8A-8B illustrate that coumarin 106 (“C1”, “AIC106”) significantly reduces insoluble tau levels in a human TSC1 mutant neuronal cell model.
Figure 8B:
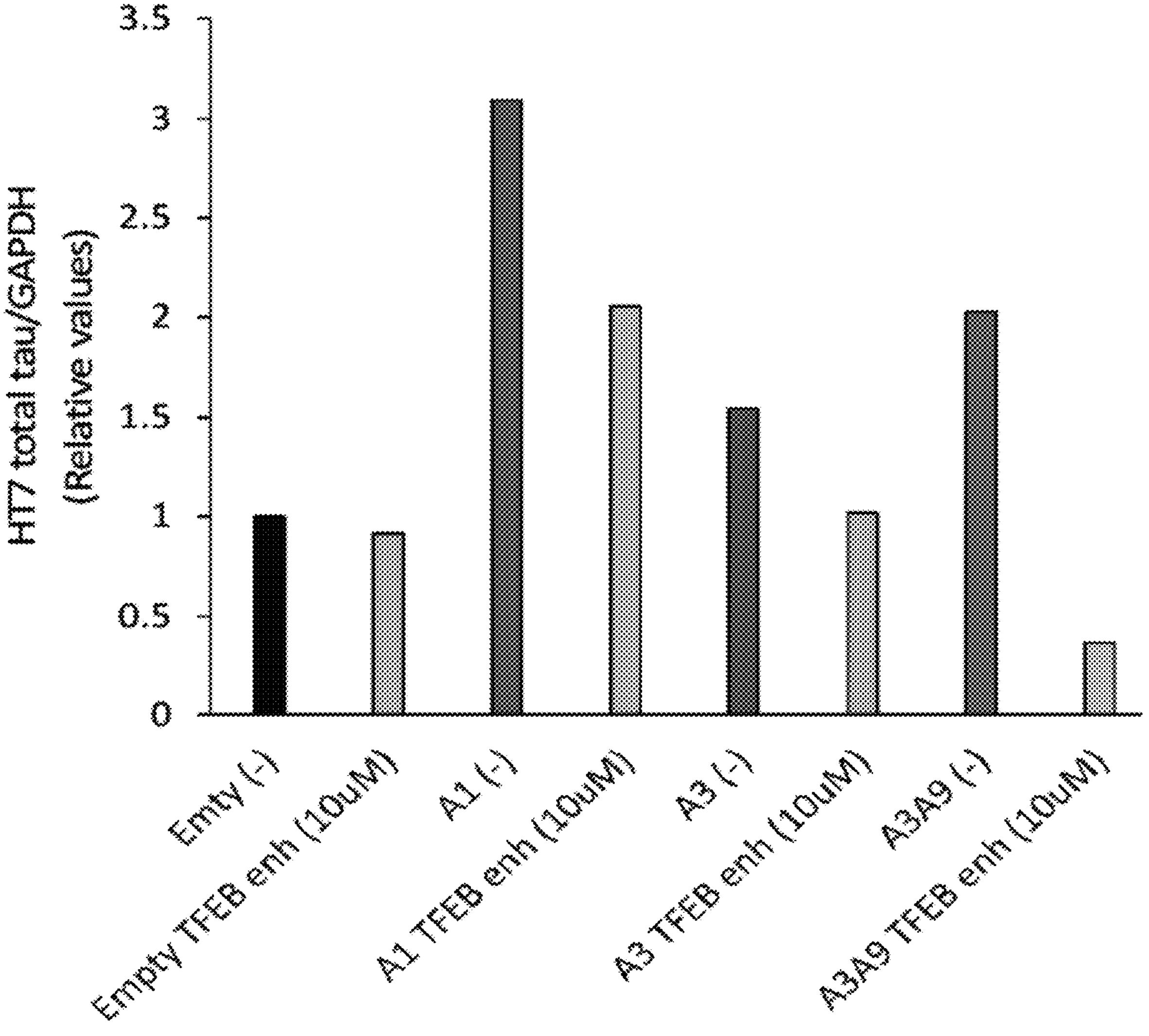

In vitro human disease efficacy studies. We recently examined the impact of C1 treatment on differentiated SY5Y cell lines expressing a mutant human tubular sclerosis (TSC1) disease gene. Mutations in this gene prevent its ability to suppress mTOR and to elevate downstream neuroprotective TFEB activity. C1 administration in these cells was shown in our studies to reduce levels of insoluble tau levels associated with the human disorder (FIG. 8).

Figure 9A:
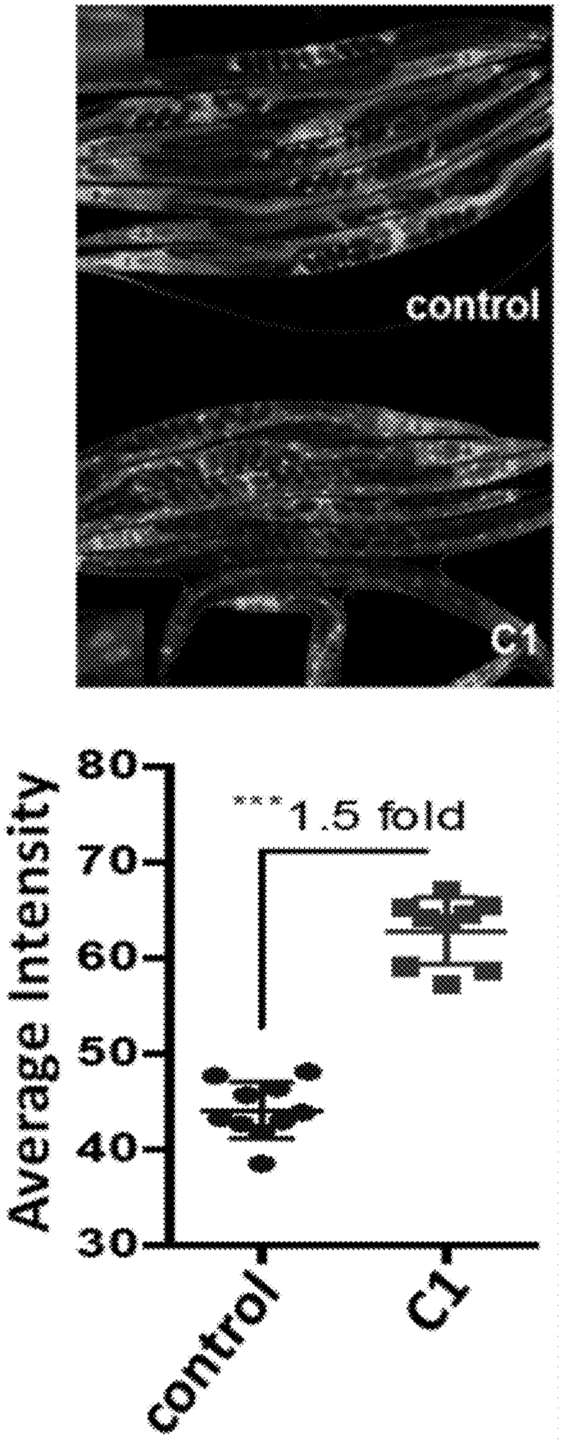
FIG. 9A-9B illustrates that coumarin 106 (“C1”. “AIC106”) induces TFEB (HLH-30) signaling in *C. elegans*.
Figure 9B:
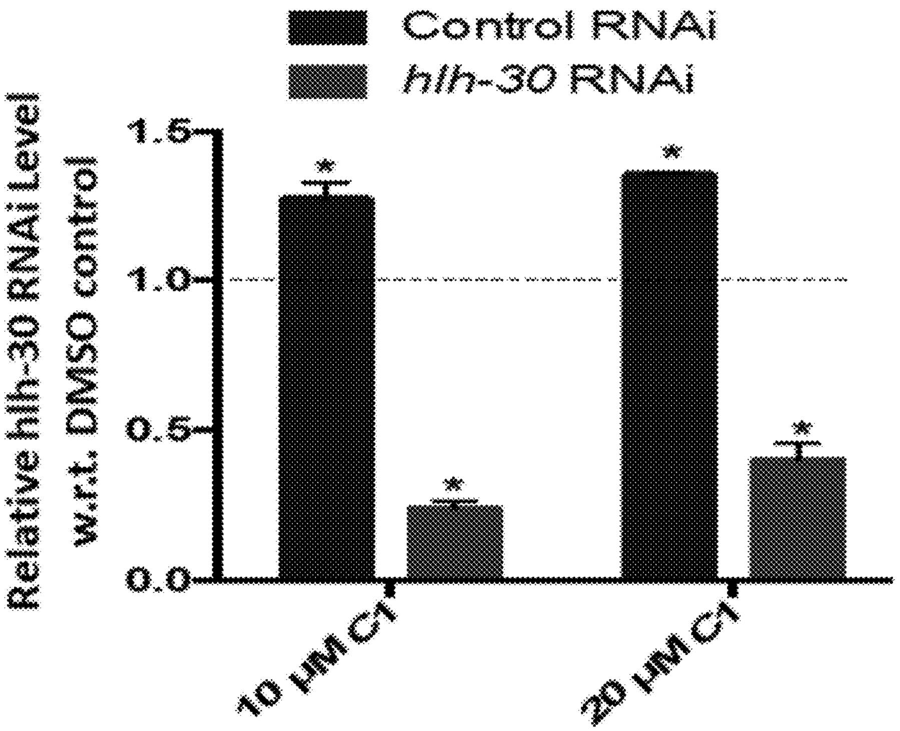
Figure 10:
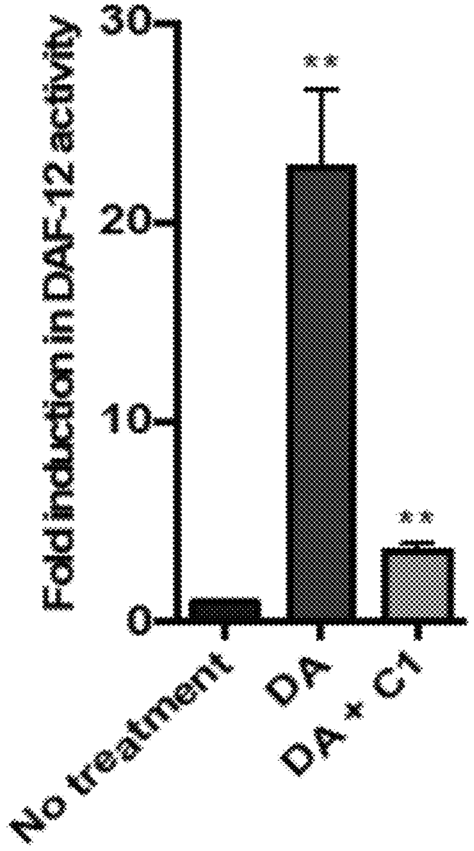
FIG. 10 illustrates that coumarin 106 (“C1”, “AIC106”) inhibits induction of the worm FXR homologue DAF-12. The ability of C1 (10 μM) to inhibit activation of the FXR worm homologue DAF-12 by its ligand dafachronic acid (Df acid); values are fold activity induction versus untreated controls; **$p<0.01$ versus GW; $p<0.05$ versus GW.
Figure 11A:
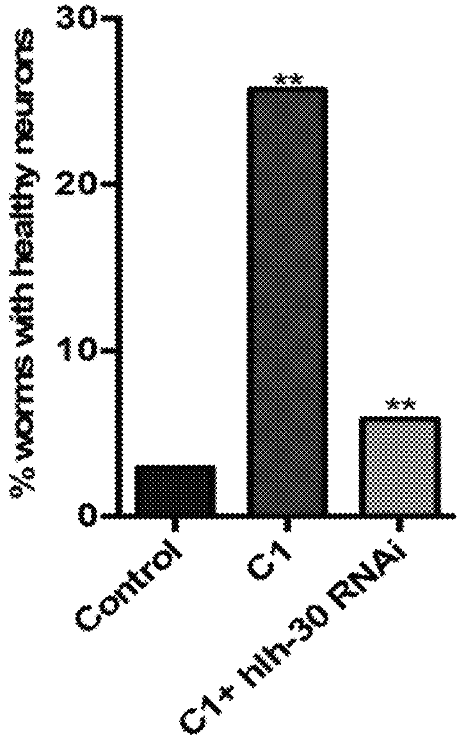
FIGS. 11A-11D illustrate that coumarin 106 (“C1”, “AIC106”) is protective in a TFEB-dependent manner in *C. elegans* models that express human neurotoxic proteins.
Figure 11B:
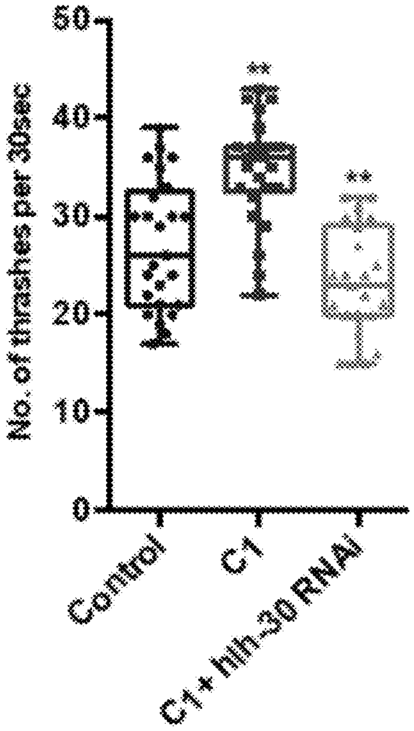
Figure 11C:
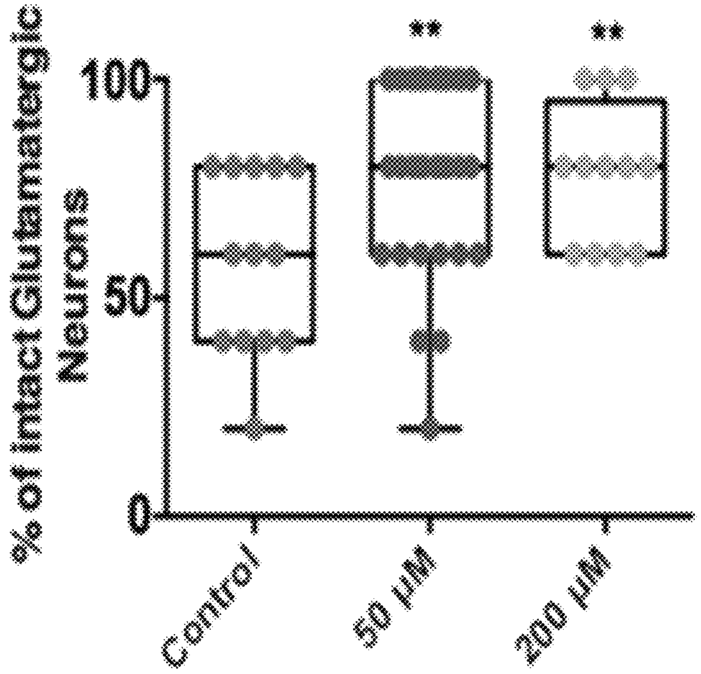
Figure 11D:
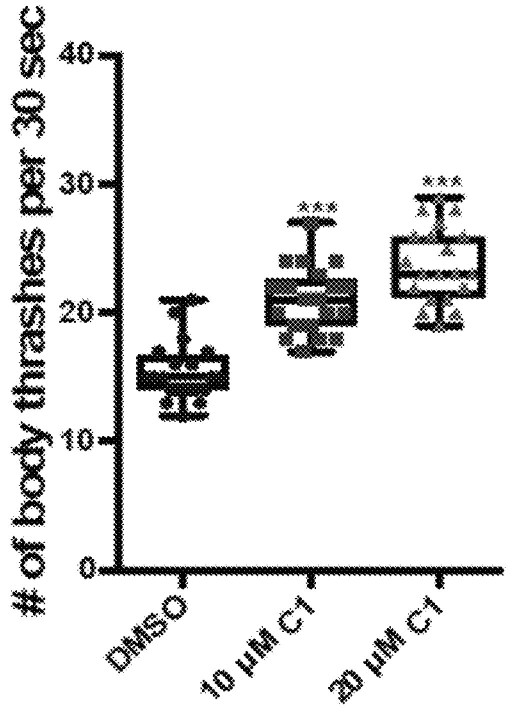
Figure 12A:
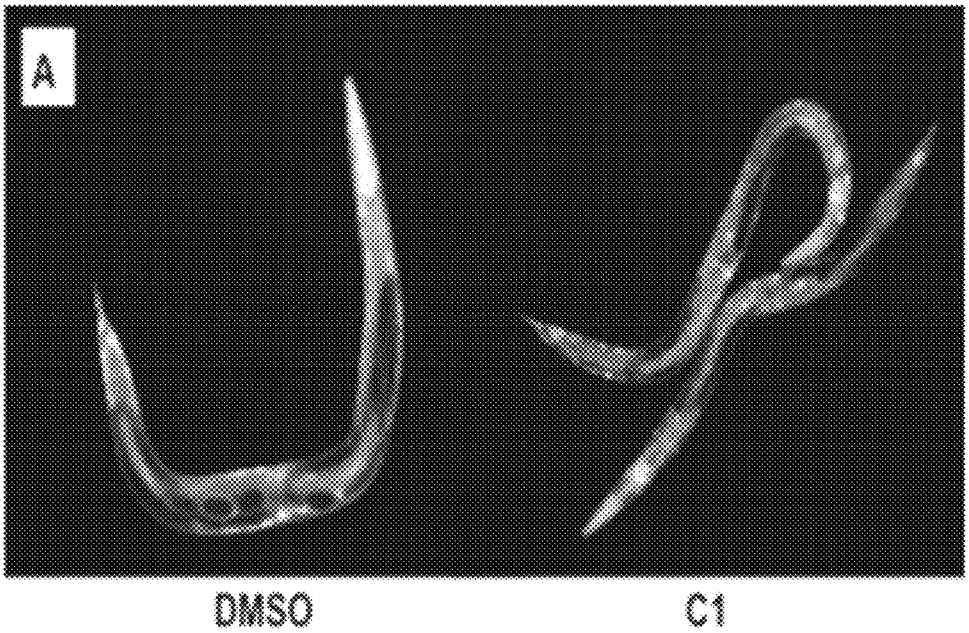
FIGS. 12A-12B illustrate that coumarin 106 (“C1”, “AIC106”) promotes induction of autophagic markers.
Figure 12B:
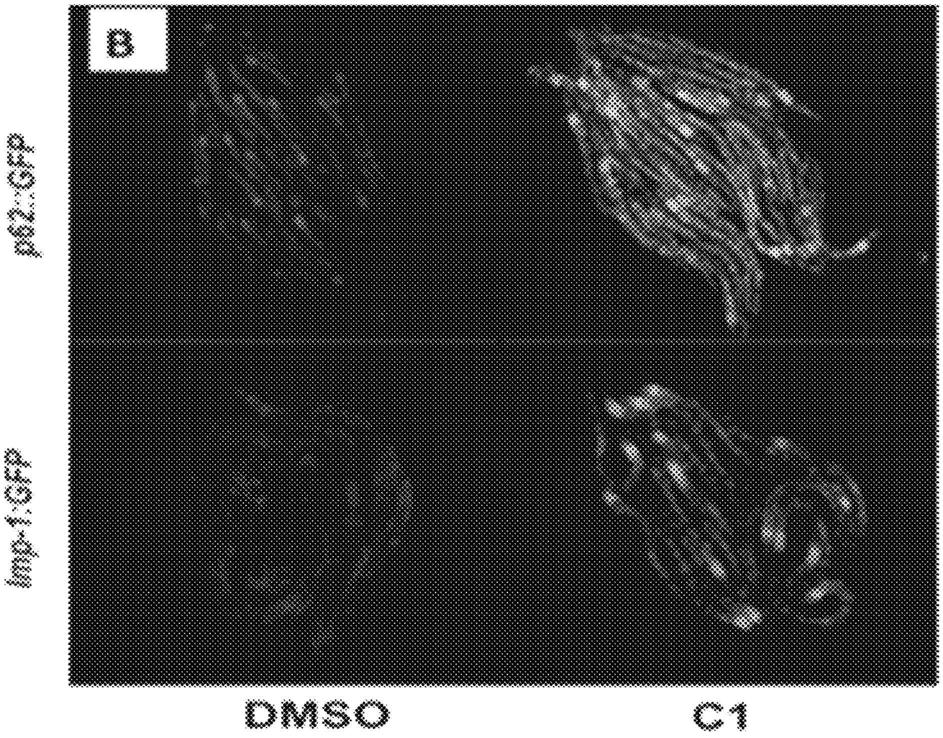
Figure 13A:
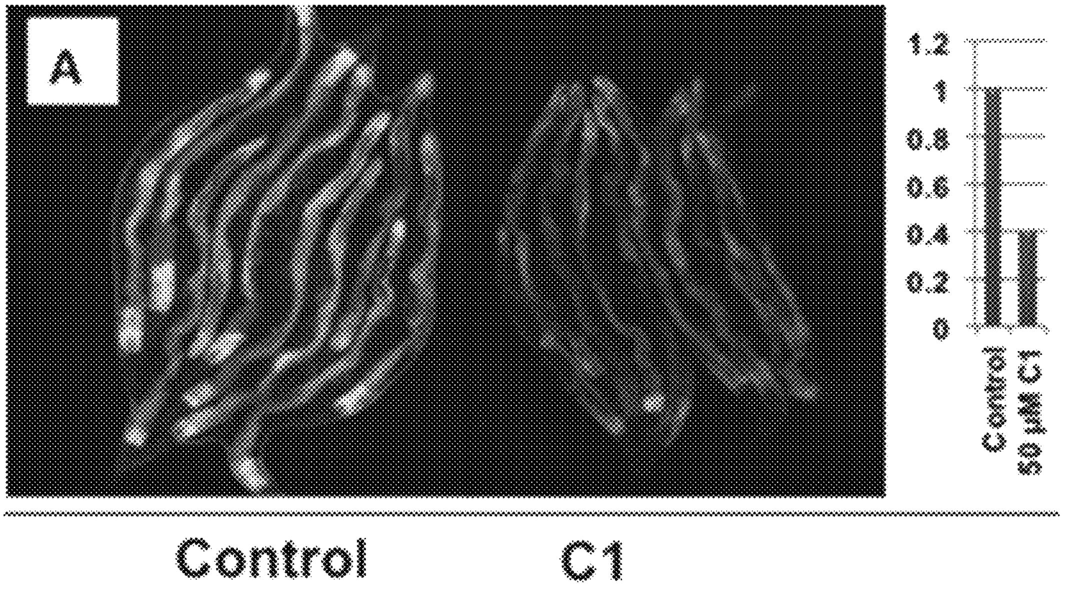
FIGS. 13A-13B illustrate that coumarin 106 (“C1”, “AIC106”) promotes increased indices of mitophagy.
Figure 13B:
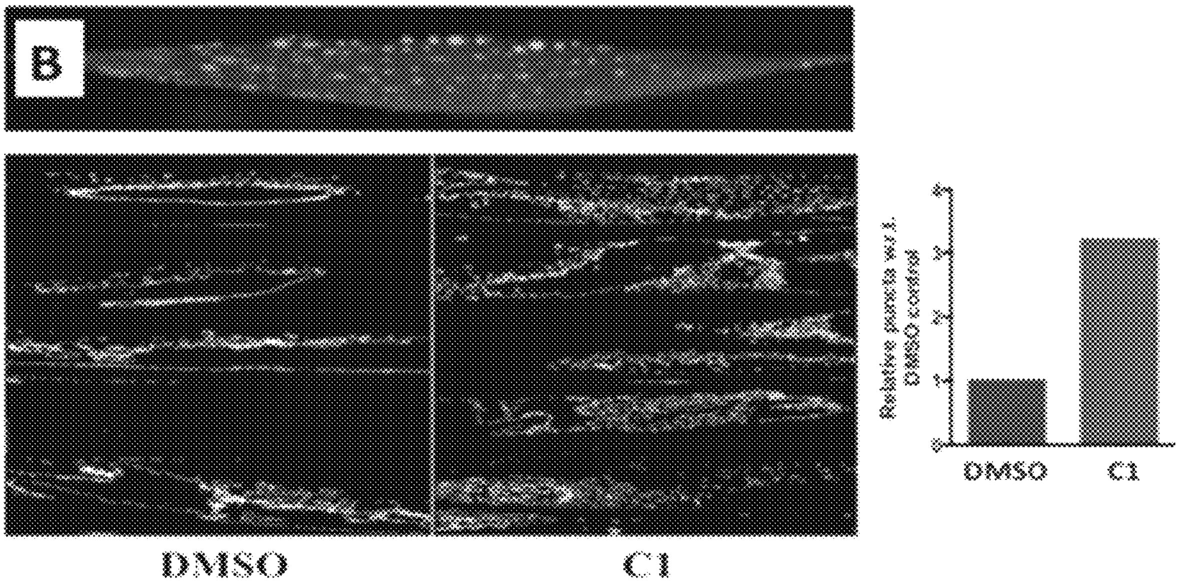
Figure 14A:
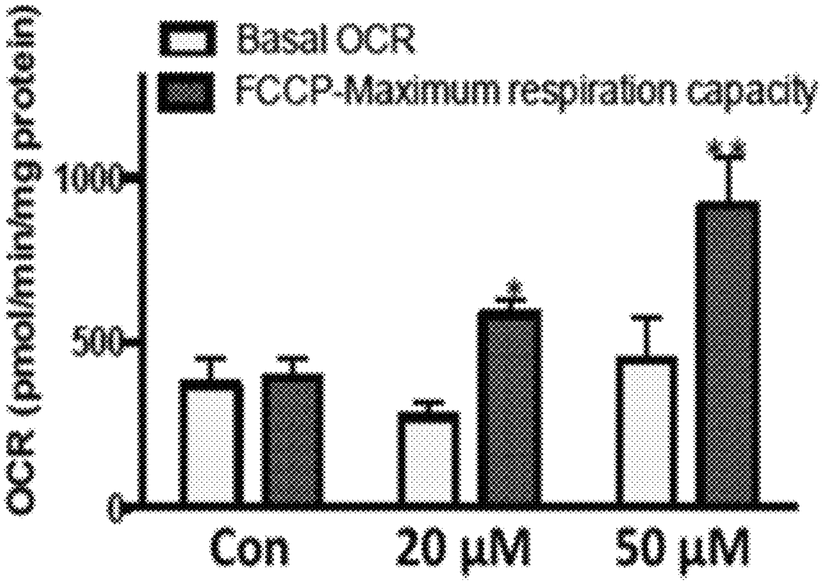
FIGS. 14A-14B illustrate that coumarin 106 ("C1", "AIC106") results in increases in mitochondrial function.
Figure 14B:
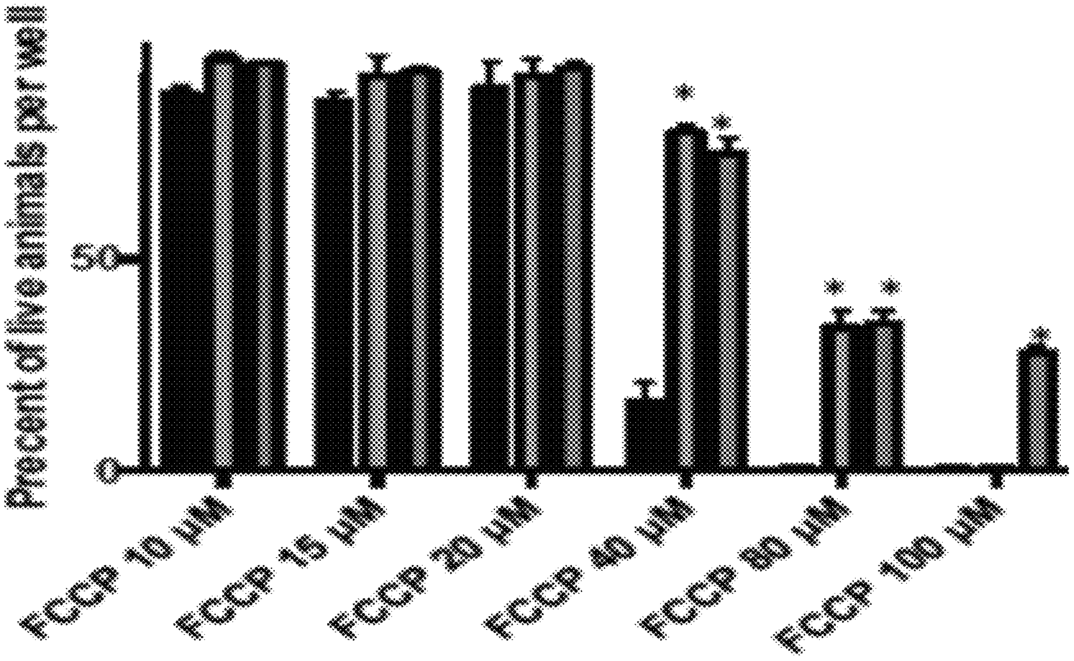

In vivo target validation and efficacy studies: *C. elegans. C. elegans* has a well-defined and genetically tractable nervous system and the experimental benefit of being relatively inexpensive, easily genetically manipulable, possessing a short lifespan and displaying stereotypical behavior phenotypes in existing disease models. Use of these "simple" animals by several laboratories has contributed to our understanding of human age-related diseases in recent years. Taking advantage of the ability to rapidly generate preliminary in vivo data in *C. elegans*, we showed that C1 administration resulted in induction of activity and expression of the worm TFEB homologue HLH-30 (FIG. 9). C1 administration was also found to inhibit activation of the FXR homologue DAF-12 elicited by the endogenous worm agonist dafachronic acid (Df acid), suggesting that FXR activity is evolutionary conserved from worms to mammals (FIG. 10). C1 administration resulted in protection in a TFEB-dependent manner in several neurodegenerative *C. elegans* models, including worms expressing human Abeta and alpha-synuclein (FIG. 11). This was found to correspond with elevations in autophagic function as demonstrated by increased autophagic flux (FIG. 12) elevated mitophagy (FIG. 13) and improvement in mitochondrial health (FIG. 14). Taken together, these preliminary in vivo data imply that C1, in its capacity as an FXR antagonist results in up-regulation of the worm TFEB homologue HLH-30 resulting in increased autophagic function and removal of damaged mitochondria and proteotoxic species.

Figure 15:
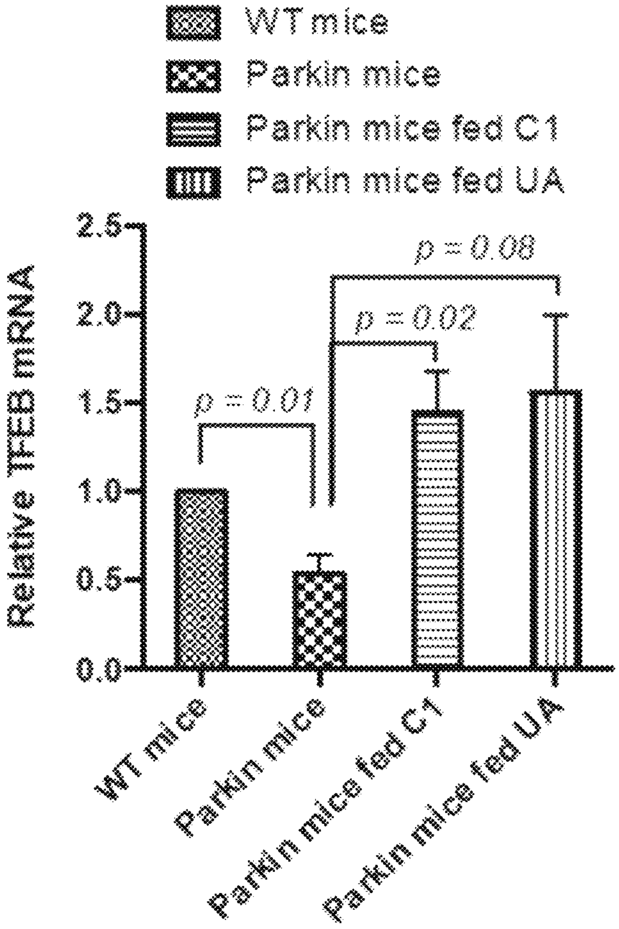
FIG. 15 illustrates that coumarin 106 ("C1", "AIC106") administration in the feed significantly up-regulates TFEB expression in vivo. Relative TFEB expression as assessed by qPCR from mRNA extracted from the SNpc of parkin mutant versus WT littermates administered C1 in the feed versus normal chow; UA was included as a positive control.
Figure 16:
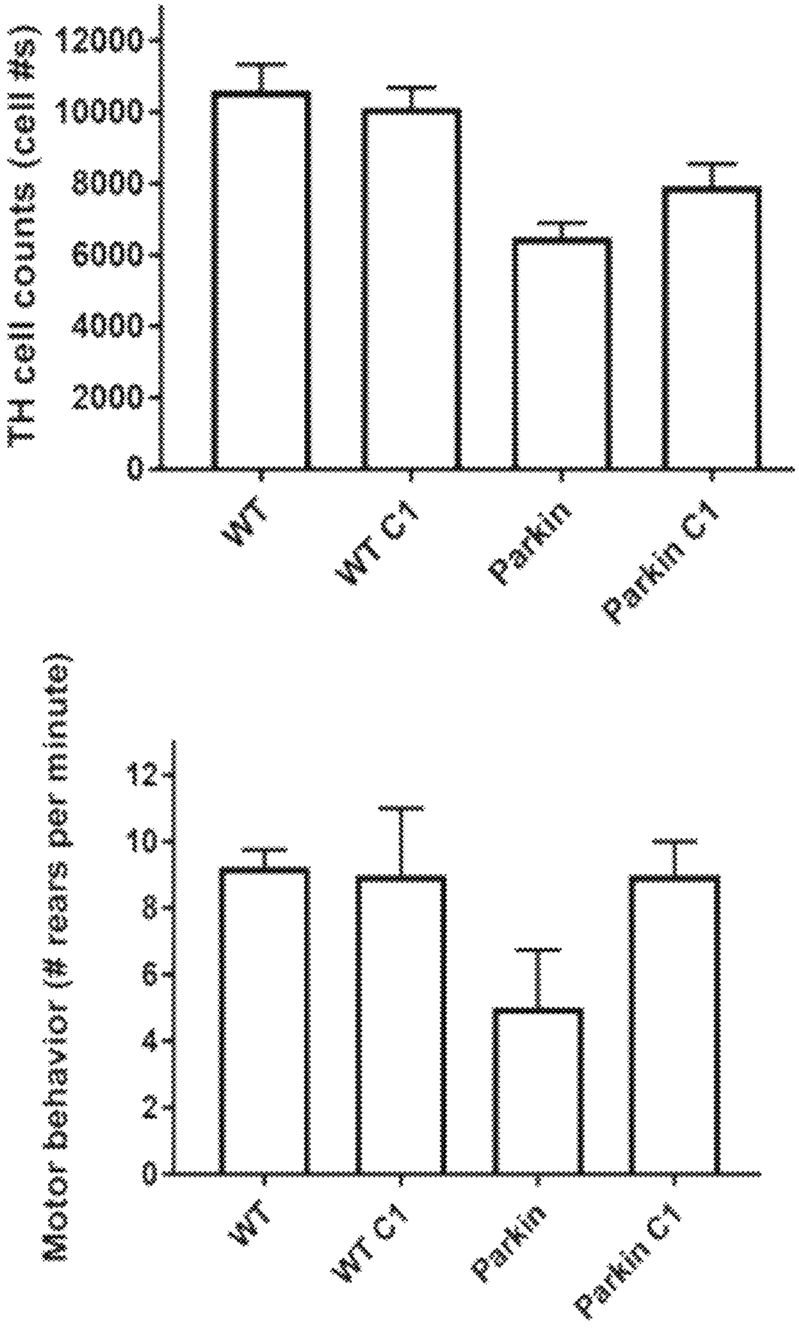
FIG. 16 illustrates that coumarin 106 ("C1", "AIC106") administration in the feed significantly abrogates DAergic SNpc cell loss and motor dysfunction associated with a PD mouse model. Stereological DAergic SNpc counts and motor behavior as assessed by rearing frequency in parkin mutant versus WT littermates administered C1 in the feed versus normal chow.

In vivo target validation and efficacy studies: mice Published data from our laboratory showed that elevation of TFEB activity via rapamycin was able to abrogate several neurodegenerative phenotypes associated with an age-related parkin mutant PD mouse model. We recently generated data demonstrating that oral administration of C1 in the feed starting from the period of first detection of neuropathology (14-16 mo.) for a 6 month period results not only in TFEB target engagement (FIG. 15) but also prevents both neuronal cell loss and motor deficits in this same mouse model (FIG. 16).

Figure 17:
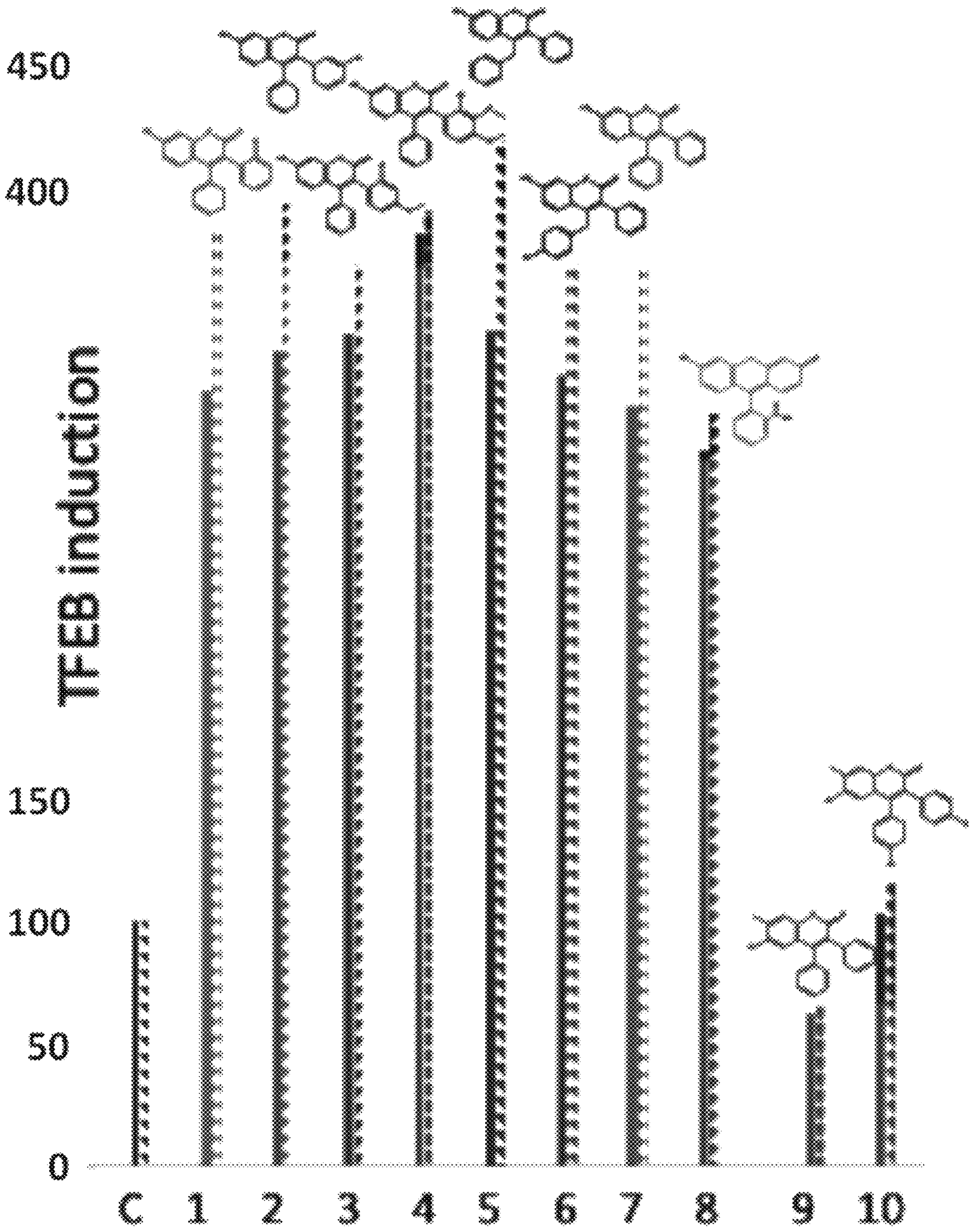
FIG. 17 illustrates that structure-activity-relationship (SAR) analysis of TFEB induction versus structural modification alterations in parent C1 (AIC106) compound. Relative TFEB expression as assessed by luciferase induction in differentiated TFEB promoter-luc expressing SY5Y cells versus vehicle-treated controls. Values represent fold induction versus vehicle. Structures are displayed above applicable TFEB induction curve.
Figure 18A:
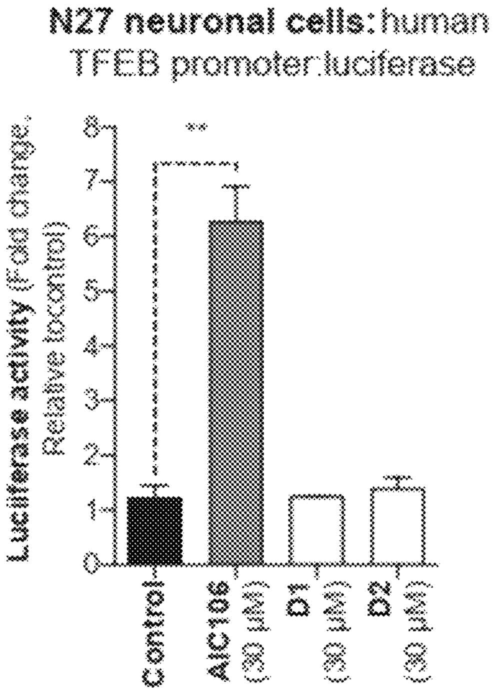
FIG. 18, panels A-F: AIC106 (Autophagy Inducing Coumarin-106) induces transcription of TFEB and its targets in vitro in rat N27 neuronal cells and in vivo in *C. elegans*. Panel A) Relative fold change in TFEB promoter activity compared to DMSO-control was determined by quantifying luciferase activity in supernatants collected from rat N27 neuronal cells post-24 hour treatment with C1 (AIC106), D1 and D2. [n=3 independent experiments (mean±SEM), **p<0.01, by one-way ANOVA with Dunnett's multiple comparisons test]. Panel B) Chemical structure of AIC106 and its structural derivative D1 and D2. Panel C) Relative fold change in mRNA of tfeb and its targets compared to DMSO-control were quantified using qRT-PCR in N27 neuronal cells post-24 hour treatment with AIC106 [N=3 independent experiments (mean±SD). *p<0.05, p<0.01 and p<0.0001, by two-way ANOVA with Sidak's multiple comparisons test]. Panel D) Changes in HLH-30 expression were measured by quantifying GFP intensity in an individual GFP-tagged HLH-30 strain (MAH235) post-24 hours treatment with AIC106 and DMSO-control. [N=3 independent experiments (mean±SD). **p<0.0001, by unpaired t-test]. Panel E) HLH-30; GFP (MAH235) were monitored by fluorescence microscopy. Panel F) Relative fold change in mRNA of hlh-30 and its targets compared to DMSO-control were quantified using qRT-PCR in young adult wild type N2 worms post-24 hours treatment with AIC106. [N=3 independent experiments (mean±SD). *p<0.05, p<0.01 and *p<0.001, by two-way ANOVA with Sidak's multiple comparisons test].
Figure 18B:
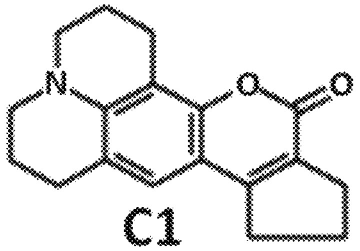
Figure 18B:
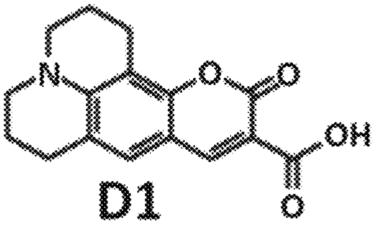
Figure 18B:
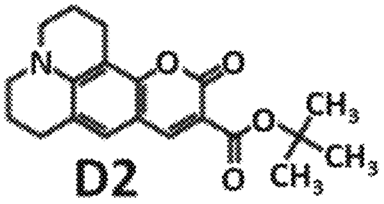
Figure 18C:
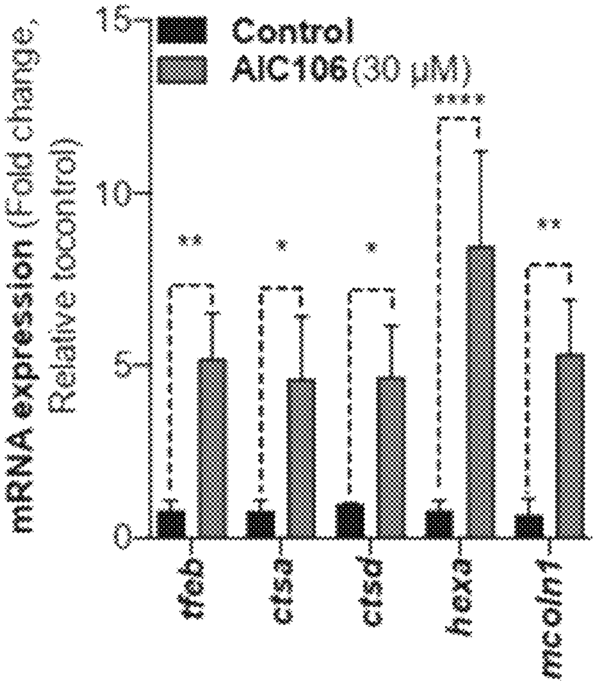
Figure 18D:
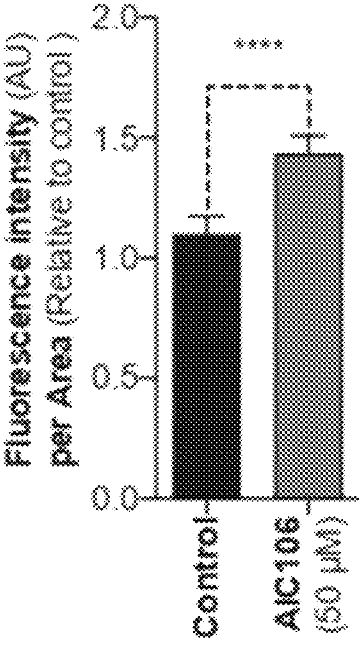
Figure 18E:
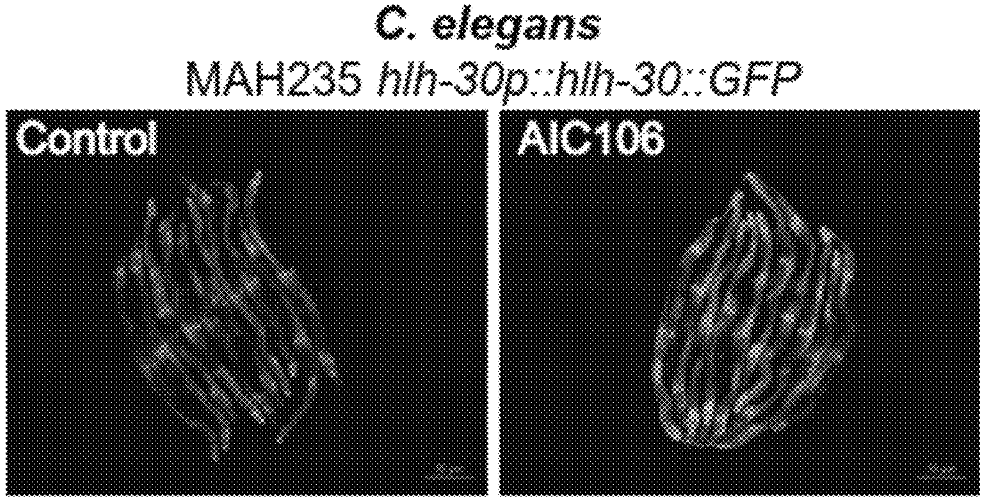
Figure 18F:
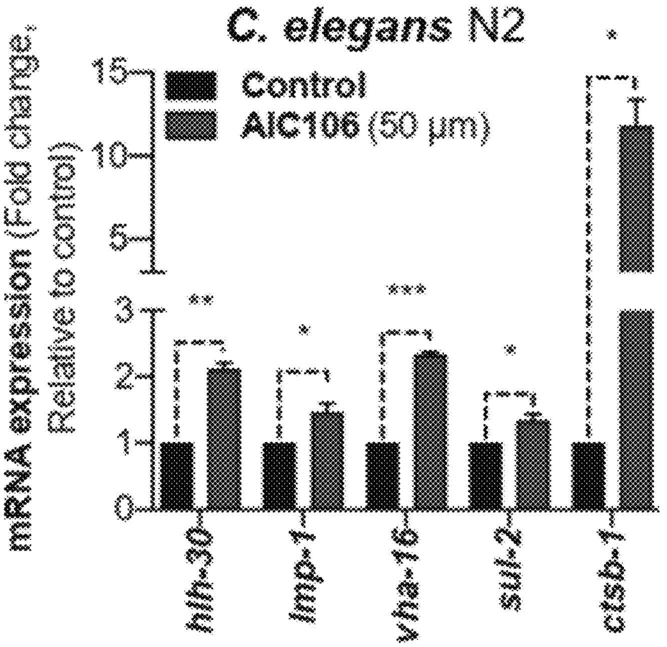
Figure 19A:
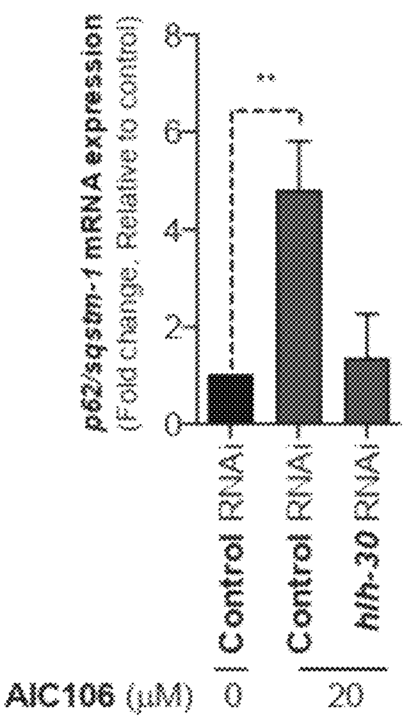
FIG. 19, panels A-G: AIC106 increases autophagic flux and lysosomal function in *C. elegans*. Panel A) Relative fold change in mRNA of autophagosome-specific protein p62/Sqstm-1 compared to DMSO-control was quantified using qRT-PCR in young adult wild-type N2 worms post-24 hours treatment with AIC106. [N=3 independent experiments (mean±SD). *p<0.05 and p<0.01, by one-way ANOVA with Sidak's multiple comparisons test]. Panel B) Changes in p62/SQSTM-1 expression were measured by quantifying GFP intensity in an individual GFP-tagged p62/SQSTM-1 worm (HZ589) post-24 hours treatment with AIC106 and DMSO-control, followed by RNAi treatment. [N=3 independent experiments (mean±SD). p<0.0001, by one-way ANOVA with Tukey's multiple comparisons test]. Panel C) p62/SQSTM-1; GFP (HZ589) was monitored by fluorescence microscopy. Panel D) Changes in lysosomal number were measured by quantifying GFP intensity in an individual GFP-tagged LMP-1 worm (RT258) post-24 hours treatment with AIC106 and DMSO-control. [N=3 independent experiments (mean±SD). p<0.0001, by unpaired t-test]. Panel E) RT258 worms were monitored by fluorescence microscopy. Panel F) Changes in lysosomal number were measured by quantifying fluorescence intensity in an individual Lysotracker Red stained wild type N2 worms post-24 hours treatment with AIC106 and DMSO-control. [N=3 independent experiments (mean±SD). **p<0.0001, by unpaired t-test]. Panel G) Lysotracker Red stained wild type N2 worms were monitored by fluorescence microscopy.
Figure 19B:
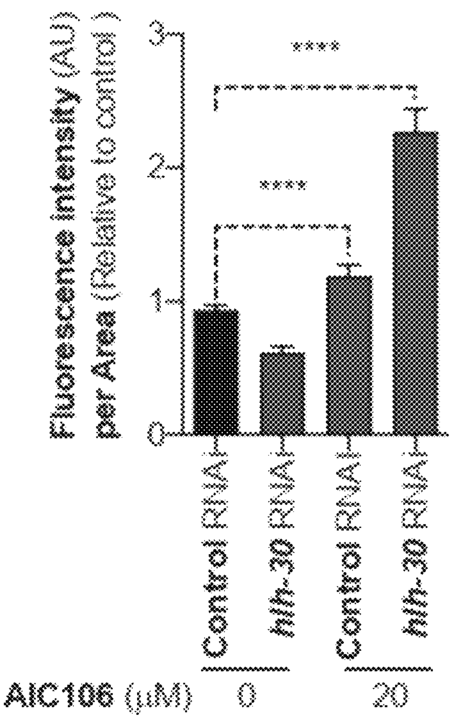
Figure 19C:
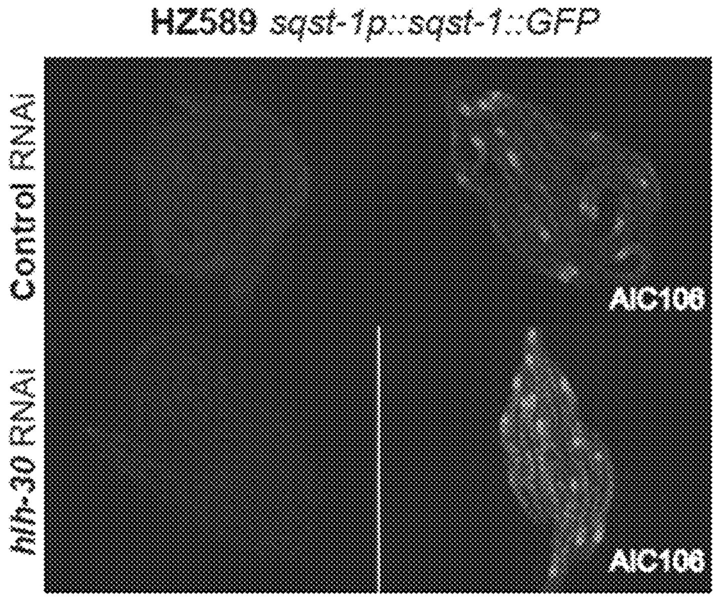
Figure 19D:
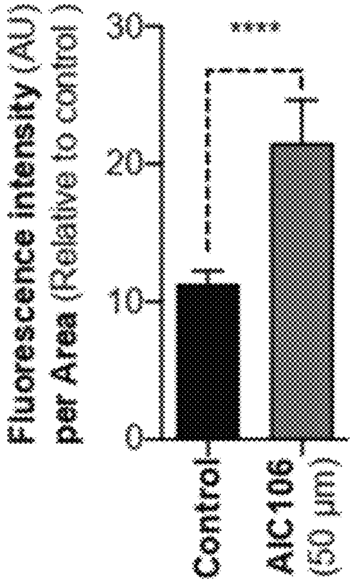
Figure 19E:
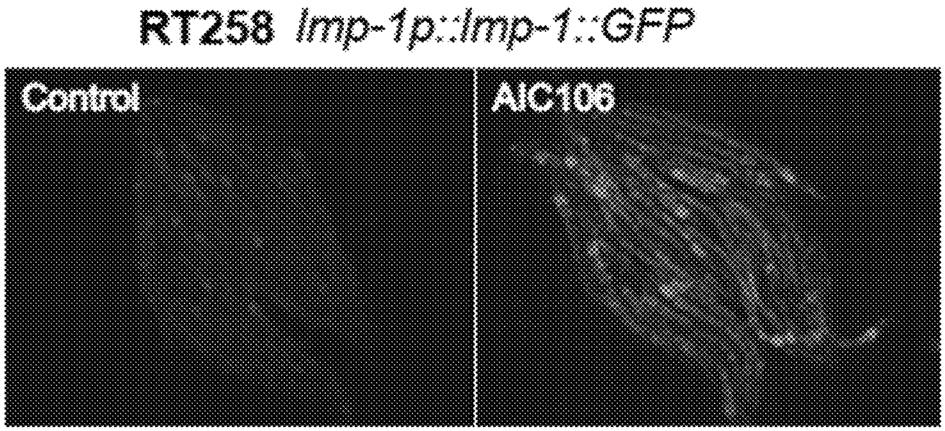
Figure 19F:
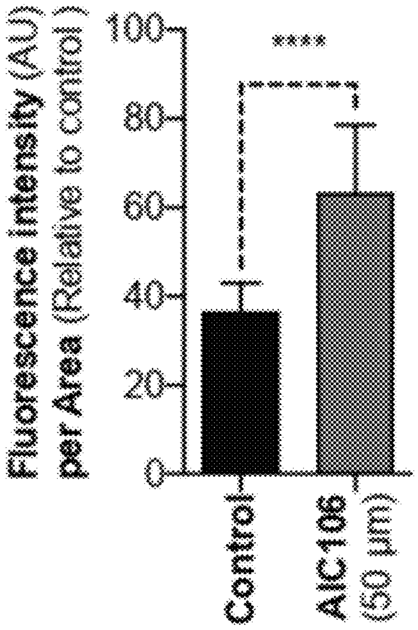
Figure 19G:
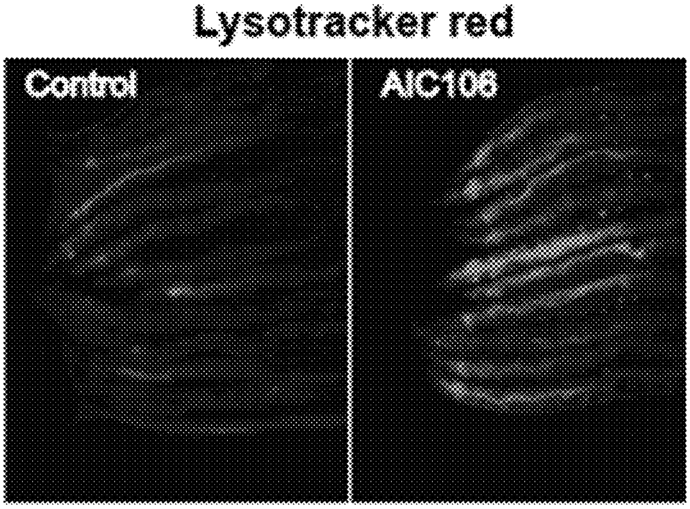
Figure 20A:
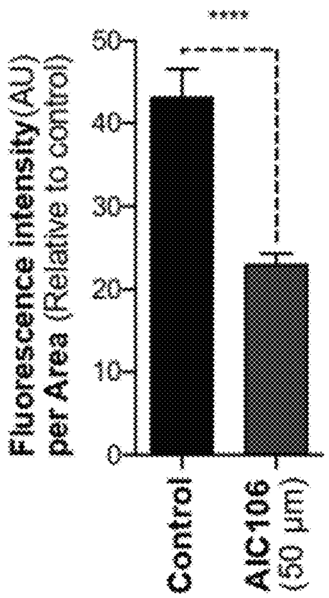
FIG. 20, panels A-H: AIC106 treatment improves mitochondrial health. Panel A) Changes in mitochondrial membrane potential were determined by quantifying fluorescence intensity of individual TMRM stained wild type N2 worms post-24 hours treatment with AIC106 and DMSO-control. [N=3 independent experiments (mean±SD). **p<0.0001, by unpaired t-test]. Panel B) TMRM stained wild type N2 worms were monitored by fluorescence microscopy. Panel C) Mitophagy flux upon AIC106 treatment was determined in DLM14 young adult worms (TOMM-7 tagged to a peptide linked dual-Fluorescent GFP) by quantifying relative fold changes in ratio of monomeric-fluorescent protein (mFP) to dual-fluorescent protein (dFP) compared to DMSO-control. Panel D) Ability of AIC106 to rescue mitochondrial toxin (FCCP) sensitivity was determined as percent survival of 24 hours treated AIC106 and DMSO-control wild type N2 worms. [N=3 independent experiments (mean±SD). **p<0.0001, by two-way ANOVA with Sidak's multiple comparisons test]. Panel E) Ability of AIC106 to rescue enhanced mitochondrial toxin (FCCP, 20 μM) sensitivity in mitophagy deficient parkin/pdr-1 mutant was determined as percent survival of 24 hours treated AIC106 and DMSO-control pdr-1(tm598) and pdr-1 (tm598); hlh-30(tm1978) mutant. [N=3 independent experiments (mean±SD). *p<0.05, by two-way ANOVA with Sidak's multiple comparisons test]. Panel F) Effect of AIC106 on mitochondrial biogenesis was determined by quantifying GFP fluorescence intensity in an individual SJ4143 worm (GFP targeted in mitochondria of intestinal cells) post-72 hours of treatment with AIC106 and DMSO-control. [N=3 independent experiments (mean±SD). ****p<0.0001, by unpaired t-test]. Panel G) SJ4143 worms were monitored by fluorescence microscopy. Panel H) Effects of AIC106 on basal (B) and maximum (M) mitochondrial respiration rate were determined by quantifying oxygen consumption rate (OCR) in wild type N2 and hlh-30(tm1978) mutant strain post-24 hours of treatment with AIC106 and DMSO-control. [N=3 independent experiments (mean±SD). *p<0.05, *p<0.001 and **p<0.0001, by one-way ANOVA with Tukey's multiple comparisons test].
Figure 20B:
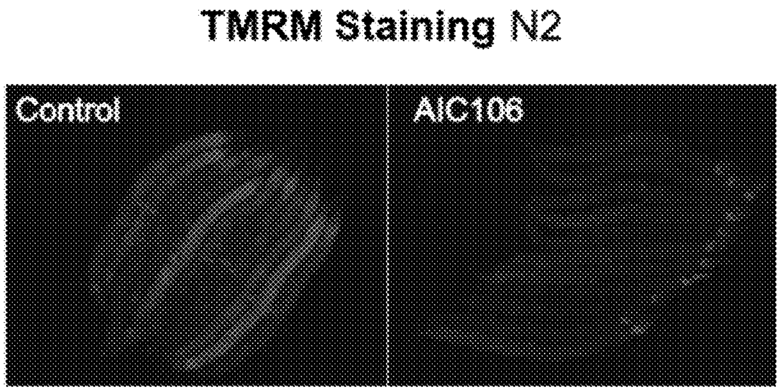
Figure 20C:
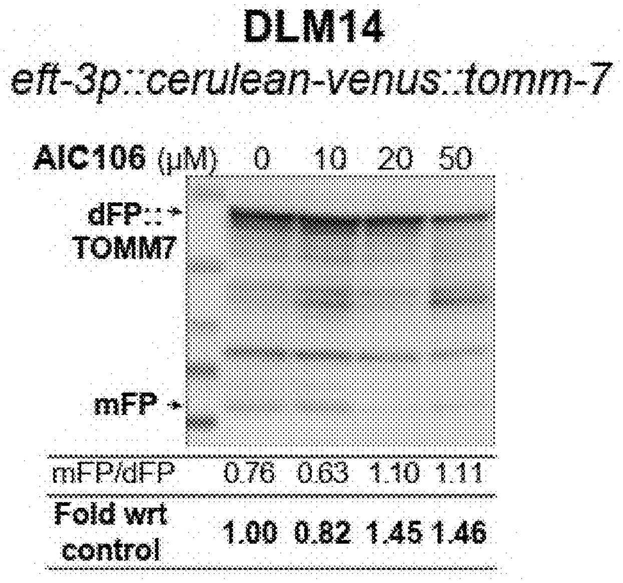
Figure 20D:
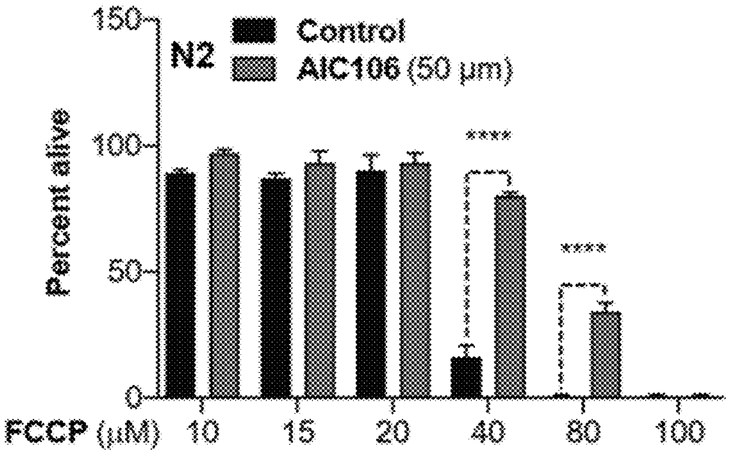
Figure 20E:
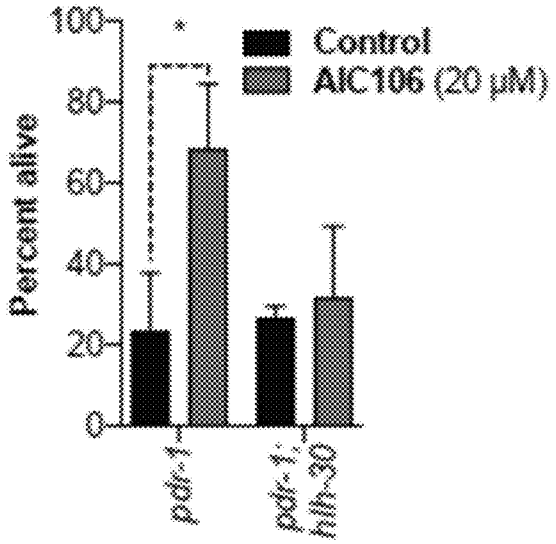
Figure 20F:
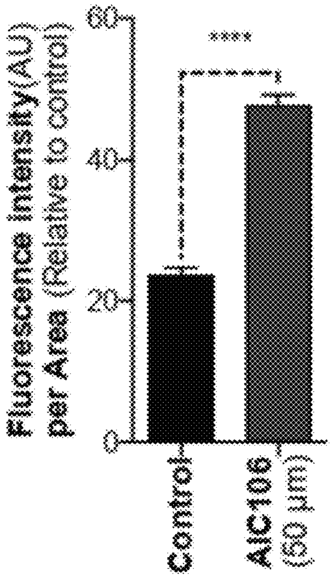
Figure 20G:
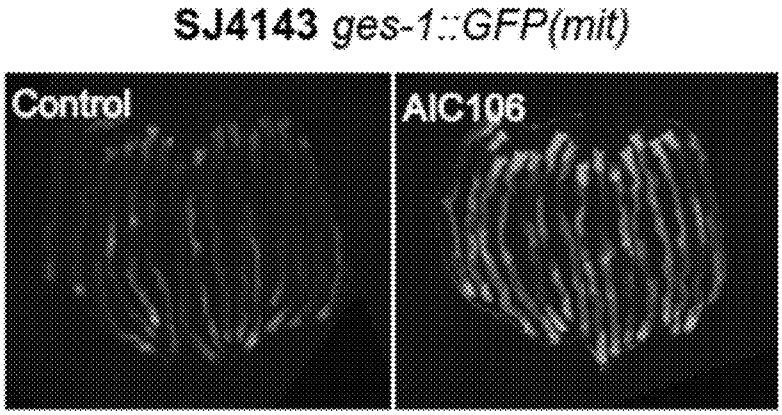
Figure 20H:
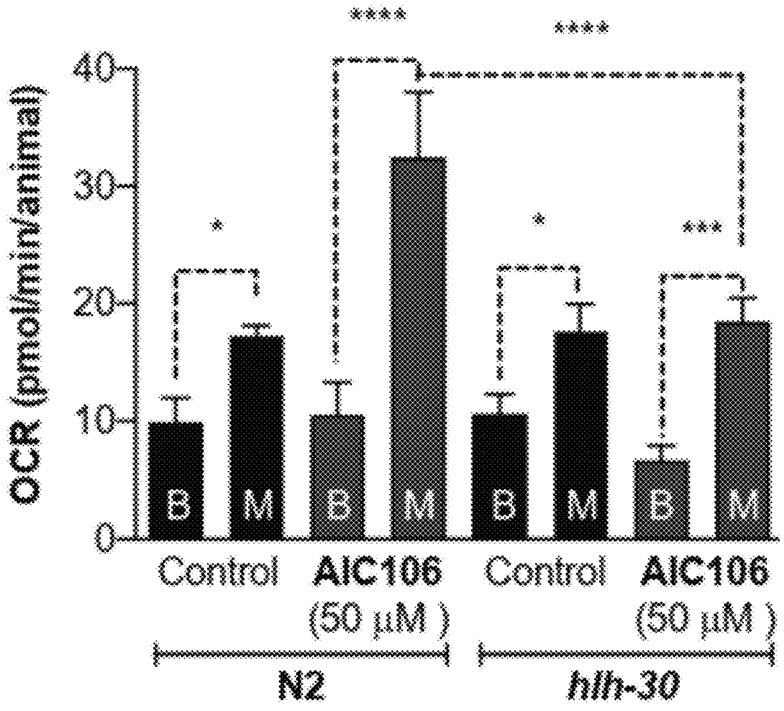
Figure 21A:
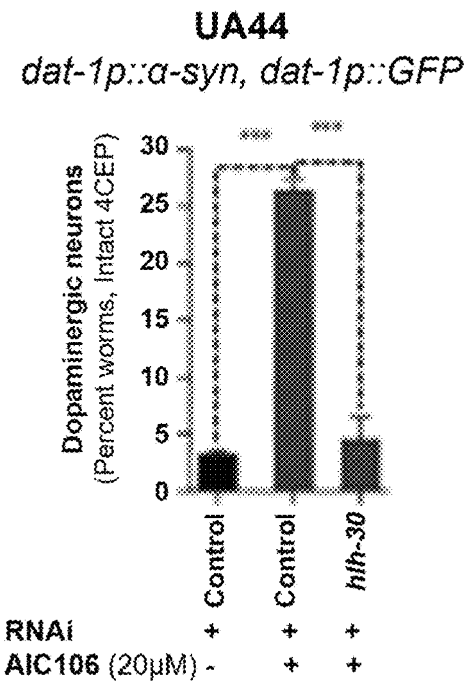
FIG. 21, panels A-F: AIC106 prevents neuronal loss and proteotoxicity in strains expressing human neurotoxic proteins. Panel A) Dopaminergic neuronal loss in day-5 UA44 worms was quantified by scoring percentage of worms with intact 4-CEP neurons in AIC106 and DMSO-control treatment. [N=3 independent experiments (mean±SD). *p<0.001, by one-way ANOVA with Tukey's multiple comparisons test]. Motor function in (panel B) day-7 NL5901 and (panel C) day-5 CL2006 worms were quantified by scoring number of thrashes for an individual worm over the period of 30 seconds (dots) in AIC106 and DMSO-control treatment. [N=3 independent experiments (mean±SD). p<0.01, *p<0.001 and p<0.0001, by one-way ANOVA with Tukey's multiple comparisons test]. Panel D) Motor function in temperature sensitive (enhanced paralysis at 25° C.) CL4176 worms was determined by scoring percent of worms paralyzed in AIC106 and DMSO-control treatment. [N=3 independent experiments (mean±SD). p<0.01, by one-way ANOVA with Tukey's multiple comparisons test]. Panel E) Lifespan analysis of CL6049 worms exposed to AIC106 and DMSO-control. [N=2 independent experiments, Treatment (median survival in days, P value compared to DMSO-control): DMSO-control (12), AIC106 10 μM (15, p<0.01), 20 μM (15, p<0.0001) and 50 μM (17, p<0.0001). P-value calculated by Logrank test]. Panel F) Effect of AIC106 on polyQ$_{40}$ aggregation was determined by scoring number of polyQ$_{40}$-YFP fluorescent puncta in an individual AM141 worm treated with AIC106 and DMSO-control. [N=3 independent experiments (mean±SD). *p<0.05 and ***p<0.001, by one-way ANOVA with Tukey's multiple comparisons test].
Figure 21B:
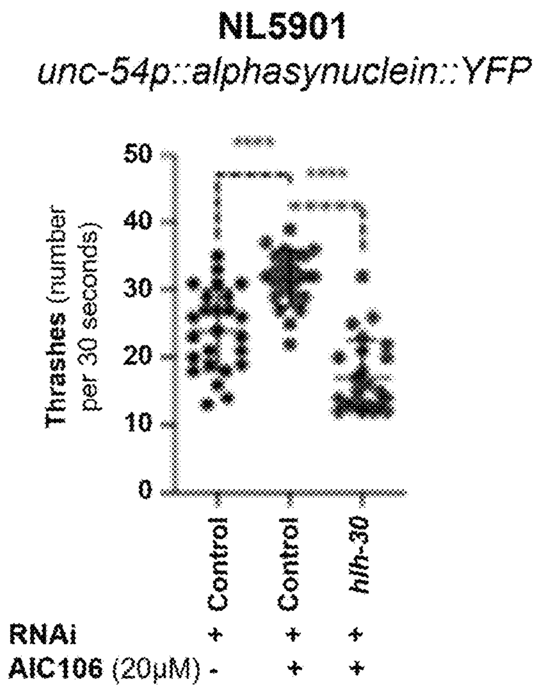
Figure 21C:
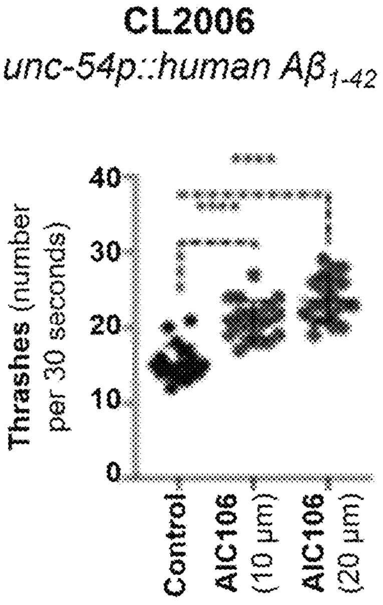
Figure 21D:
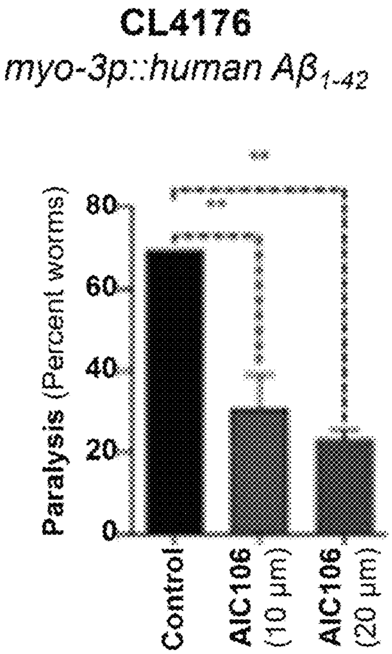
Figure 21E:
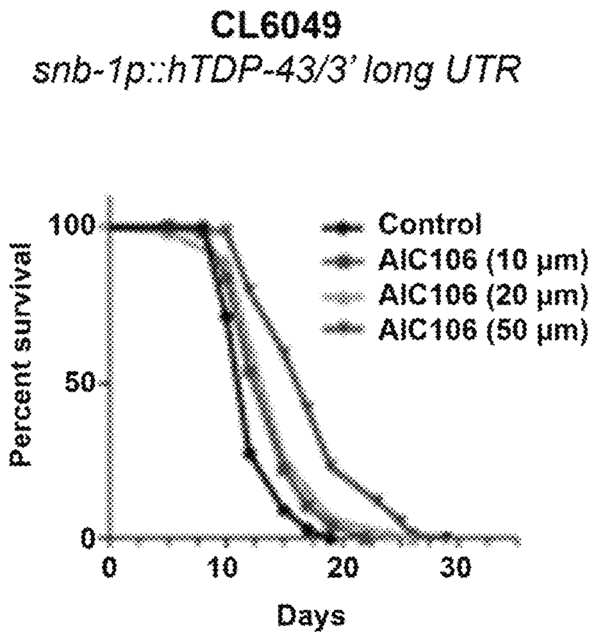
Figure 21F:
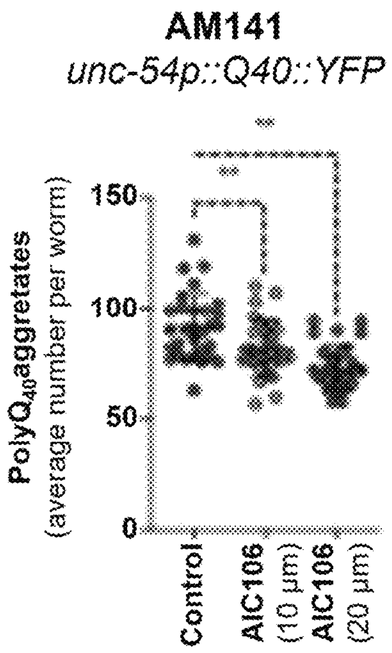
Figure 22B:
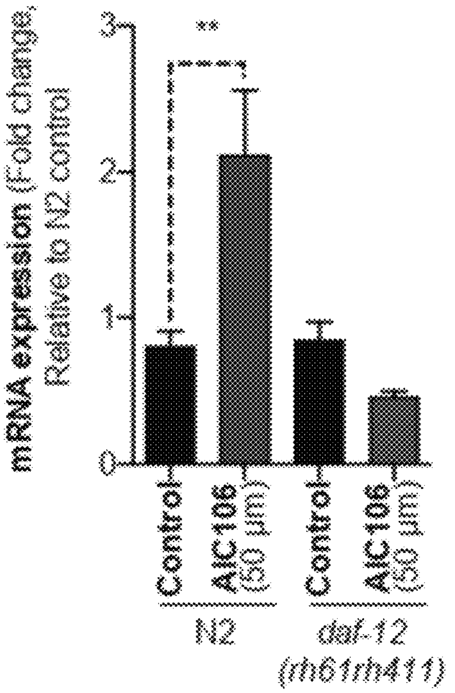
FIG. 22, panels A-H: AIC106-induced HLH-30 expression is mediated by the nuclear hormone receptor DAF-12. Panel A) The upstream promoter region (2 kB) of hlh-30 was analyzed by JASPAR CORE database to determine DAF-12 binding sites (1: SEQ ID NO:1, 2: 1: SEQ ID NO:2, 3: SEQ ID NO:3, 4: SEQ ID NO:4, 5: SEQ ID NO:5, 6: SEQ ID NO:6, 7: SEQ ID NO:7, 8: SEQ ID NO:8, 9: SEQ ID NO:9, 10: SEQ ID NO:10, 11: SEQ ID NO:11, 12: SEQ ID NO:12). Panel B) Relative fold change in mRNA of hlh-30 compared to DMSO-control was quantified using qRT-PCR in young adult wild-type N2 and daf-12(rh61rh411) worms post-24 hours treatment with AIC106. [N=3 independent experiments (mean±SD). **p<0.01, by one-way ANOVA with Sidak's multiple comparisons test]. Panel C) Effects of AIC106 on DAF-12 activity was determined in a mammalian one-hybrid assay by quantifying changes in the luciferase activity of DAF-12 ligand (dafachronic acid, DA) induced treatment. [N=3 independent experiments (mean±SD). *p<0.05 p<0.01 and *p<0.001, by one-way ANOVA with Tukey's multiple comparisons test]. Panel D) Schematic diagram showing that addition of AIC106 or inhibition of DAF-12 ligand synthesis, which leads to un-liganded DAF-12 may result in enhanced HLH-30 expression. Panel E) Dafadine-A (DFA), a specific inhibitor of key enzyme required for synthesis of DAF-12 ligand induces HLH-30 expression. Immunoblot for GFP was performed on protein lysate of HLH-30; GFP (MAH235) young adult worms treated with DFA or DMSO-control for 24 hours. Panel F) Protection against mitochondrial toxin (FCCP) was determined by quantifying survival of young adult worms treated 24 hours with DFA or DMSO-control. [N=3 independent experiments (mean±SD). p<0.01, by two-way ANOVA with Tukey's multiple comparisons test]. Panel G) Motor function in day-7 NL5901 worms were quantified by scoring number of thrashes for an individual worm over the period of 30 seconds (dots) in DFA and DMSO-control treatment. [N=3 independent experiments (mean±SD). p<0.01, by unpaired t-test] Panel H) Mitophagy deficient pdr-1/parkin mutant were genetically engineered to carry heterozygous point mutation in ligand-binding domain (LBD) of DAF-12 protein, pdr-1(tm598); daf-12(lbd$^{m}$+/−.) Mutation, which results in ligand-insensitive DAF-12, shows significant rescue in mitochondrial toxin (FCCP) sensitivity of pdr-1 mutant as determined by increased percent survival. [N=3 independent experiments (mean±SD). *p<0.05, by one-way ANOVA with Tukey's multiple comparisons test].
Figure 22C:
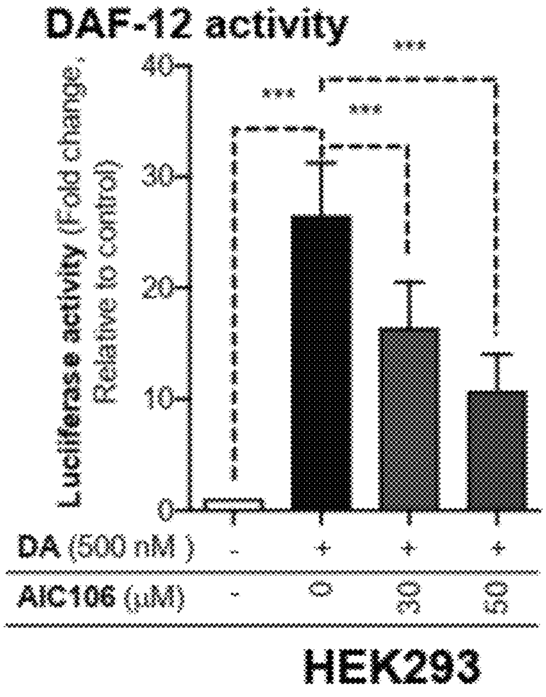
Figure 22D:
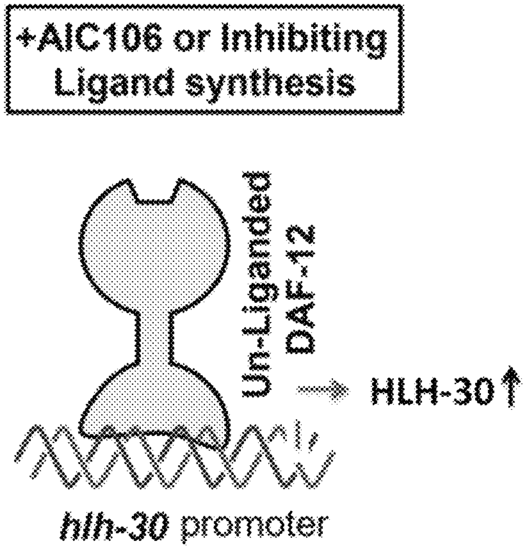
Figure 22E:
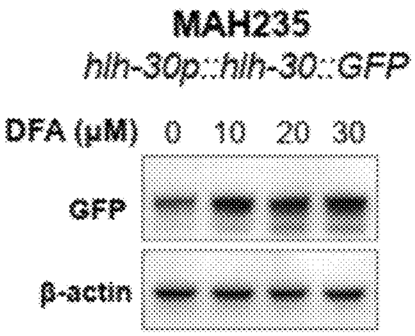
Figure 22F:
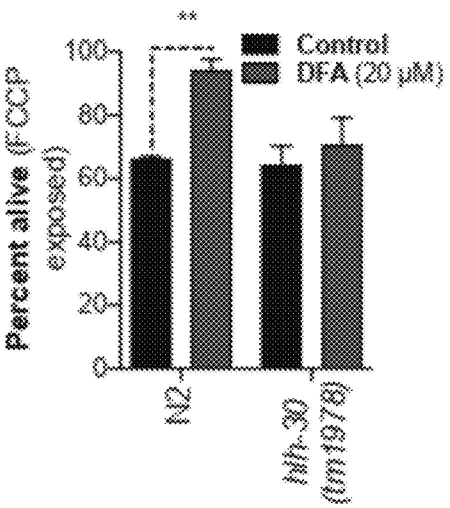
Figure 22G:
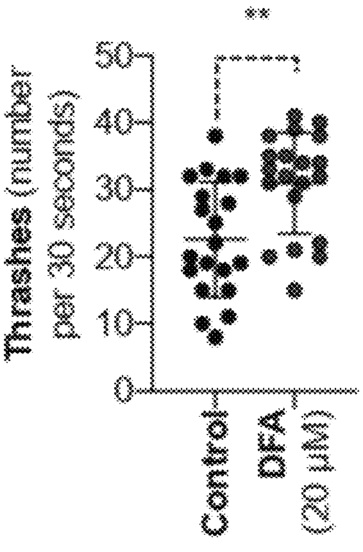
Figure 22H:
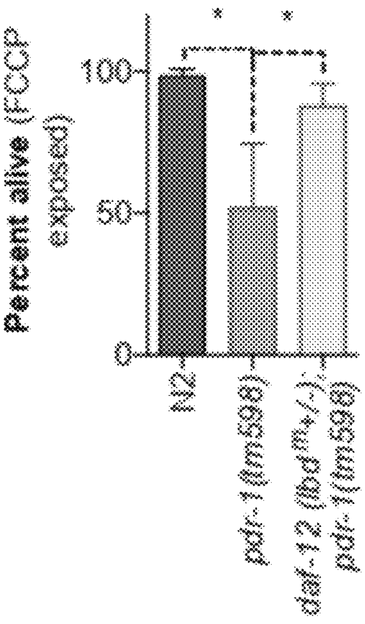
Figure 23A:
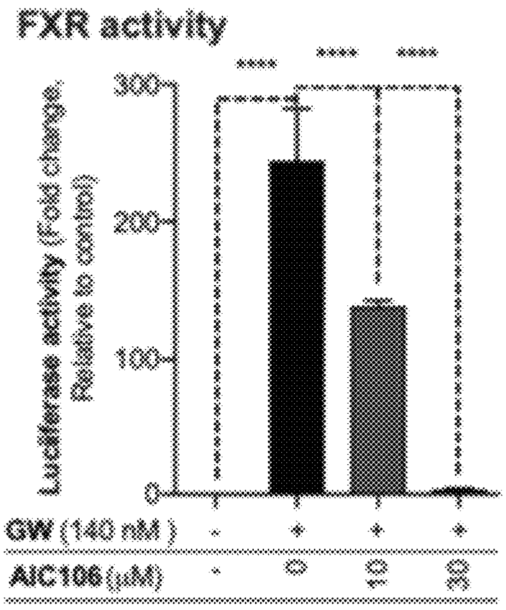
FIG. 23, panels A-H: FXR modulation enhances HLH-30 expression in human neuronal SH-SY5Y cells. Panel A) Effects of AIC106 on human FXR activity was determined in a mammalian one-hybrid based kit assay by quantifying changes in the luciferase activity of FXR ligand (GW4064, GW) induced treatment. [N=3 independent experiments (mean±SD). ****p<0.0001, by one-way ANOVA with Tukey's multiple comparisons test]. Panel B) Protein expression of TFEB, cathepsin-D (CAT-D) and small heterodimer partner-1 (SHP-1) was determined by immunoblot in neuronal SH-SY5Y cells post-24 hours of treatment with AIC106 and DMSO-control. Panel C) AIC106 enhances autophagic flux in neuronal SH-SY5Y cells. Autophagic flux in DMSO-control and AIC106 treated neuronal cells was determined by quantifying levels of autophagosome specific LC3-II protein both in presence and absence of autophagy inhibitor bafliomycin A1 (Baf A, 10 nM). Panel D) Relative fold change in the band intensity of LC3-II protein, normalized to loading control actin. Values are relative to DMSO-control. [N=3 independent experiments (mean±SD). *p<0.05 and ****p<0.0001, by one-way ANOVA with Tukey's multiple comparisons test]. Panel E) Effects of AIC106 treatment for 72 hours on basal TAU and phosphorylated-TAU in differentiated human neuronal SH-SHY5Y and heterozygous TSC1(+/−) mutant SH-SY5Y neuronal cells were quantitated by immunoblotting following total protein extraction. Relative fold change in the band intensity compared to SH-SY5Y control treatment for (panel F) total TAU and (panel G) phosphorylated-TAU, normalized to loading control GAPDH. [N=3 independent experiments (mean±SD). *p<0.05 and **p<0.01, by one-way ANOVA with Sidak's multiple comparisons test]. Panel H) AIC106 treatment improves viability and health of differentiated SH-SY5Y-TSC1(+/−) neuronal cells. Images were taken post-96 hours after treatment of differentiated neuronal cells with AIC106.
Figure 23B:
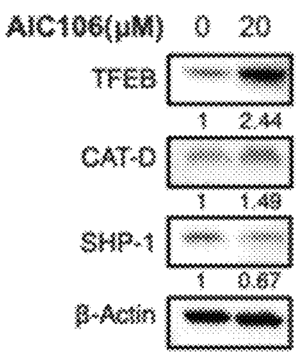
Figure 23C:
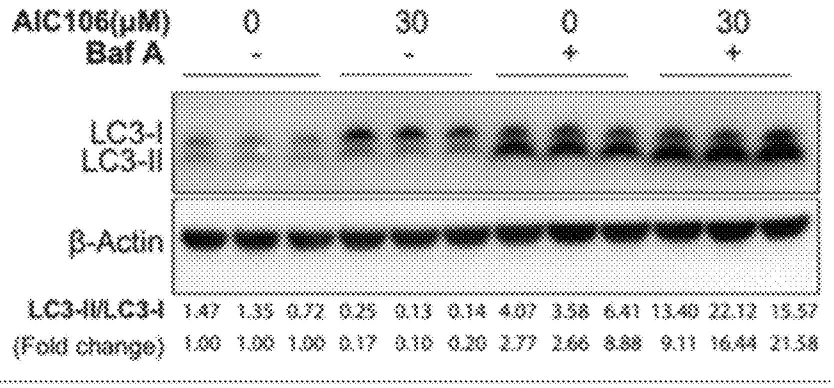
Figure 23D:
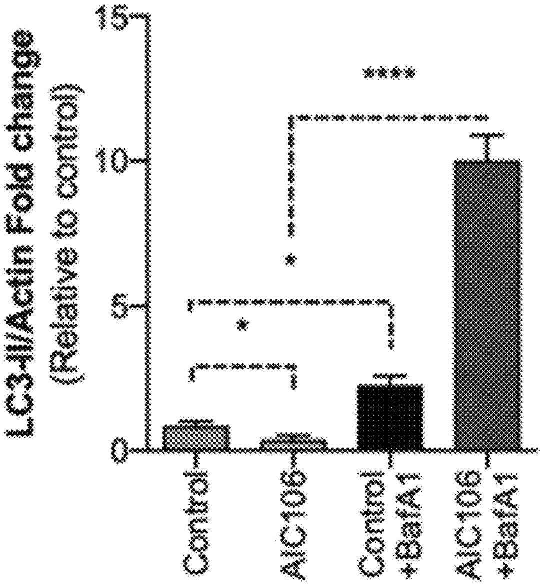
Figure 23E:
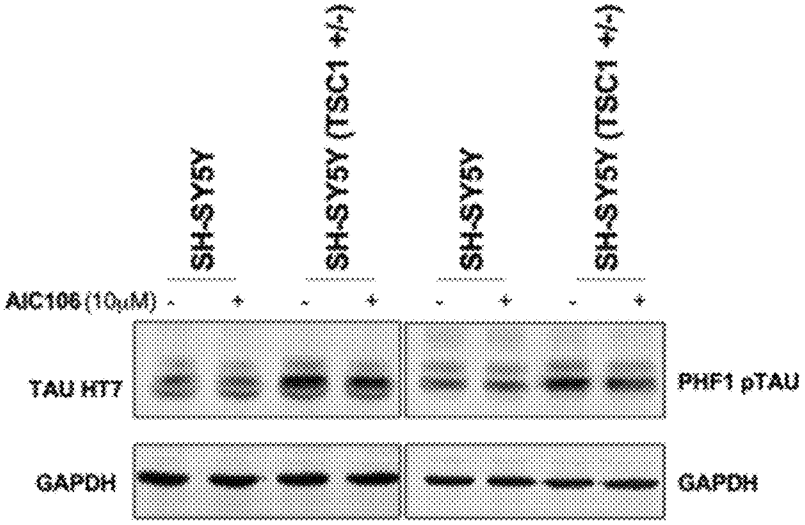
Figure 23F:
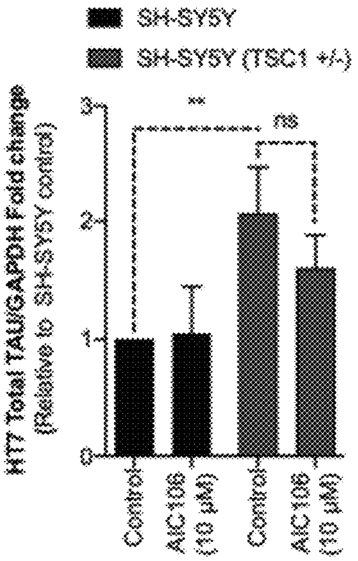
Figure 23G:
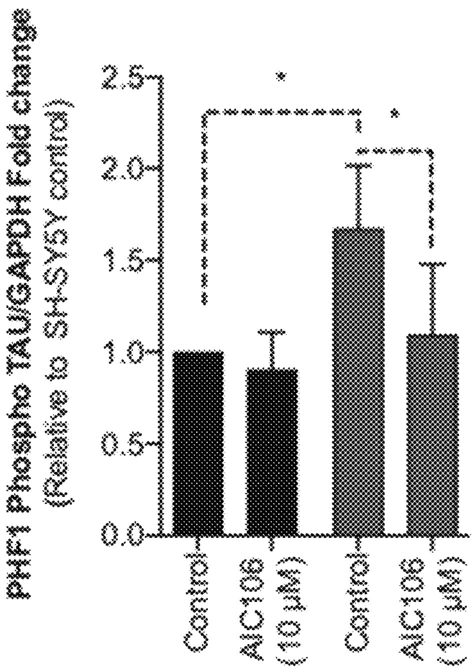
Figure 23H:
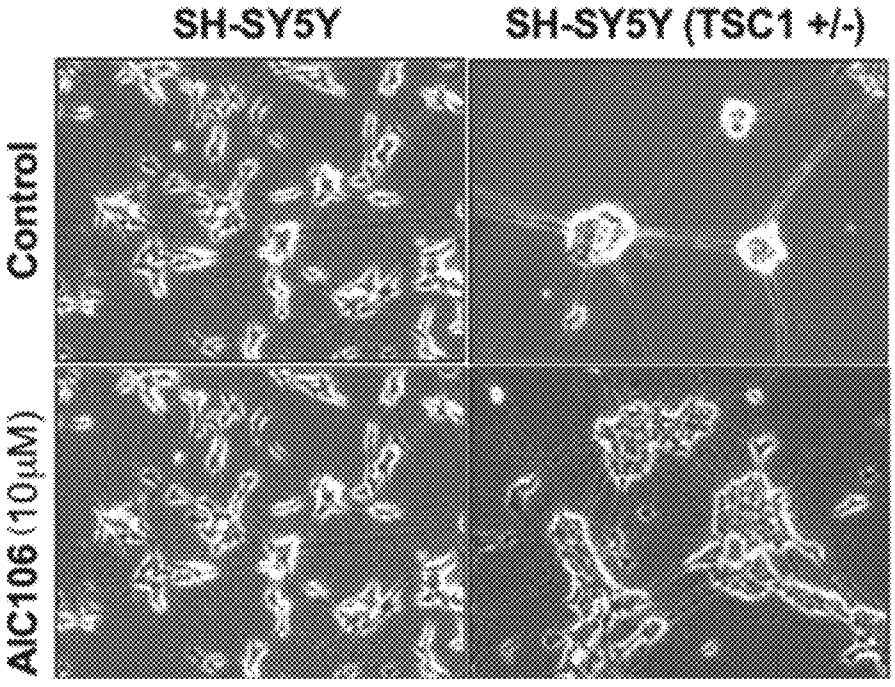

Structure-Activity-Relationship (SAR) studies. As part of our initial screening effort, we identified multiple related structures to C1 that, importantly, displayed various levels of C1 induction (FIG. 17). We have identified multiple related structures to C1 that, importantly, do not induce TFEB that we have used to undertake a rudimentary SAR.

C1 is a promising autophagy-inducing agent for the treatment of chronic age-associated disease. Strong genetic and biochemical evidence has additionally led to the identification of FXR as a target of drug action.

Example 2

Pharmacological Modulation of FXR/DAF-12 Induces TFEB-Dependent Autophagy and Suppresses Neurodegeneration Autophagy is a conserved biological process that helps in clearing up subcellular contents including toxic protein aggregates and damaged organelles. A growing body of evidence suggests that age-related defects in autophagy underlie many neurodegenerative diseases. Consequently, identifying compounds and interventions enhancing autophagy holds great therapeutic potential in mitigating these neurodegenerative diseases. Here we describe a characterization of a novel compound, AIC106 (Autophagy Inducing Coumarin-106), identified in a screen for transcriptional inducers of transcription factor EB (TFEB), a master regulator of autophagy and lysosomal biogenesis. Therapeutic effects of AIC106 were tested across a wide range of proteotoxic disease models in *C. elegans* and cell-based human neuronal tauopathy models. We show that AIC106 prevents several pathologies associated with these models and enhances mitochondrial function and content by transient induction of autophagy including mitophagy. Further, we show that AIC106 modulates activity of DAF-12 (and human homolog FXR) by enhancing their ligand-unbound state, which in turn induces TFEB. Our study highlights the therapeutic potential of FXR-TFEB signaling mediated autophagy in neurodegenerative diseases.

Introduction

A characteristic feature of aging and many age-related diseases is enhanced accumulation of damaged cellular organelles and proteins. Defective autophagy is a major underlying factor in this process (Cuervo, 2008; Leidal et al., 2018). Autophagy acts to clear and recycle damaged, non-functional proteins and cellular organelles within the lysosome. Autophagy is well known for its critical role in cellular and tissue homeostasis (Buszczak and Kramer, 2019; Marino et al., 2011), differentiation and development (Mizushima and Levine, 2010), protein and organelle quality control (Anding and Baehrecke, 2017; Arias and Cuervo, 2011), metabolism (Rabinowitz and White, 2010), immunity (Clarke and Simon, 2019; Levine et al., 2011) and aging (Rubinsztein et al., 2011). Defects in autophagy contribute to several chronic disease states including hearth diseases, cancer, neurodegenerative disease, and diabetes (Levine and Kroemer, 2019). Autophagy is a tightly regulated multistep process requiring close co-ordination between autophagosome and lysosomal function. Genetic mutations affecting either the function of autophagosomes or lysosomes or their fusion renders individuals susceptible to neurological disorders including Alzheimer's and Parkinson's disease (Levine and Kroemer, 2019; Levine et al., 2015; Pan et al., 2008). Despite a clear link between neuronal autophagy and these diseases, we still lack a comprehensive understanding of the signaling events involved in its regulation (Nakamura and Yoshimori, 2017). Several chemical screens have been undertaking in order to identify potent inducers of autophagy (Panda et al., 2019; Zhang et al., 2019). The majority of these screens have utilized autophagosome-specific reporters such as LGG-1 or p62, resulting in compounds that successfully initiate autophagy but are limited in their ability to enhance lysosomal function.

Since its discovery in 2009, the basic helix-loop-helix (hlh) transcription factor TFEB has emerged as an important regulator of both autophagy and lysosomal biogenesis (Sardiello et al., 2009). The ability of TFEB to not only control but co-ordinate expression of genes involved in both processes makes it a potentially important therapeutic target for the treatment of age-related neurodegenerative diseases (Martini-Stoica et al., 2016). Recent studies, including from our own group, have shown that a decline in autophagic activity accompanies reduced TFEB expression in age-related neurodegenerative disease (Cortes et al., 2014; Siddiqui et al., 2015; Tsunemi et al., 2012; Wang et al., 2016b). Conversely, enhancing TFEB expression has been demonstrated to be beneficial in protecting against pathologies associated with these disorders (Decressac et al., 2013; Polito et al., 2014; Torra et al., 2018; Wang et al., 2016a). Classically, TFEB function is regulated via its translocation in and out of the nucleus in response to external stimuli including starvation or heat stress. Transient, nuclear TFEB translocation triggers the downstream expression of several target autophagic and lysosomal genes (Napolitano et al., 2018). Few recent chemical screens designed to identify TFEB inducers have utilized TFEB translocation as screen readout (Song et al., 2016; Wang et al., 2017; Zhang et al., 2019). Surprisingly, despite growing evidence demonstrating reduced expression of TFEB in many diseased conditions, no screens utilizing TFEB expression have been reported (Di Malta et al., 2019).

We undertook a screen of natural product library (TimTech NPL640) for effects on TFEB transcriptional induction and identified a series of compounds that act to induce TFEB gene expression. The top hit from the screen was a coumarin-based compound, which we named Autophagy Inducing Coumarin-106 (AIC106). Using a series of reporter-based assays and models of proteotoxicity in *C. elegans* we found that AIC106 was capable of significantly inducing autophagosome-lysosomal function resulting in enhanced mitochondrial capacity and prevention of proteotoxicity in various models expressing human neurotoxic proteins. Most importantly, we discovered through our characterization of the mechanisms of action of AIC106, a previously unknown role for the nuclear hormone receptor (NHR) DAF-12/FXR in TFEB induction that was conserved in human neuronal cells. This has an important implication for FXR's potential role in neurodegenerative diseases.

Results

Screening for Transcriptional Inducers of TFEB/HLH-30

To identify novel transcriptional inducers of TFEB, we transfected rat neuronal N27 cells with a vector driving expression of secreted-luciferase under control of the human TFEB promoter. We exposed cells to a single dose of compounds from a natural product library (FIG. 25, panel A) and identified AIC106 as a lead compound that significantly enhanced luciferase transcription (6-7 fold, FIG. 18, panel A). AIC106 belongs to a family of coumarin compounds containing an active benzopyrone ring. Other structurally similar compounds (FIG. 18, panel B) belonging to this same coumarin family did not elicit enhanced luciferase expression (FIG. 18, panel A). We validated enhanced TFEB promoter activity by confirming increased TFEB mRNA levels in N27 cells. Enhanced expression of TFEB in AIC106 treated N27 cells were accompanied by increased TFEB activity as shown by increased expression of downstream TFEB target genes (FIG. 18, panel C).

Enhanced HLH-30/TFEB Expression and Autophagic Flux in *C. elegans*

Figure 25A:
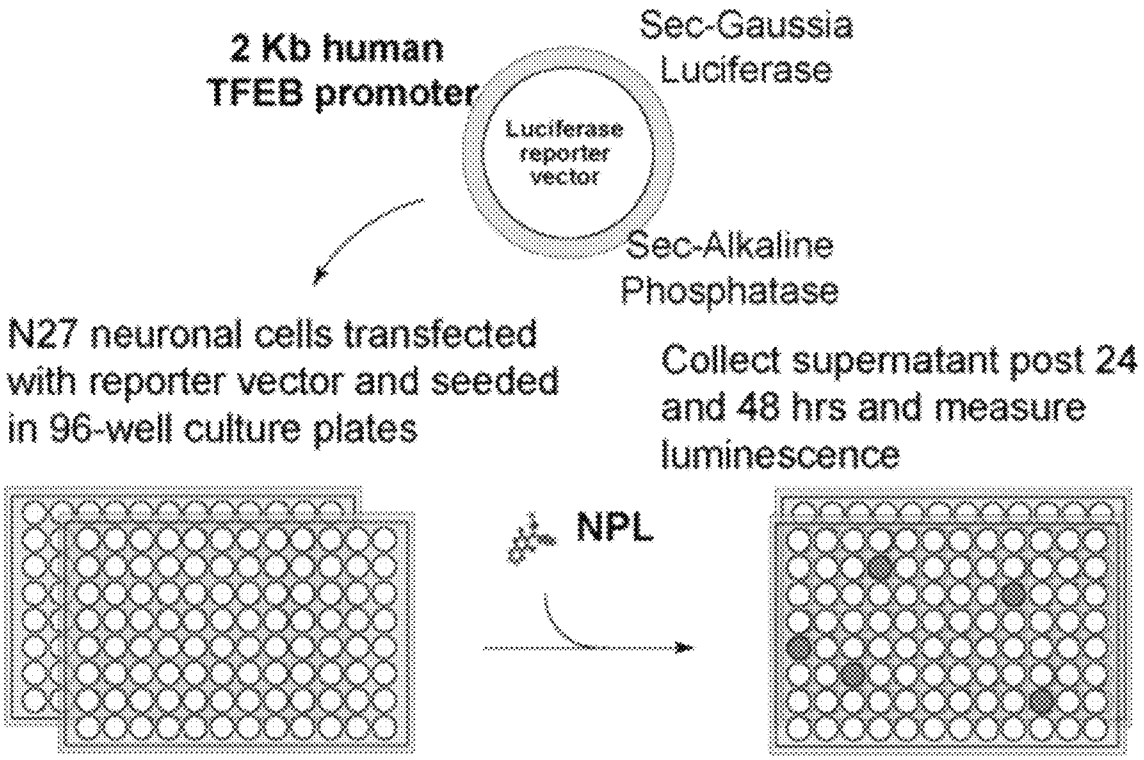
FIG. 25, panels A-B::AIC106 identified as a lead compound in a TFEB-transcription based screen. Panel A) Rat Neuronal N27 cells were transfected with a vector construct driving expression of secreted-*Gaussia* luciferase (Sec-*Gaussia*) in control of 2 kb human TFEB promoter. Next day, cells were seeded into 96-well cell culture plate and exposed to compounds (30 μM) from natural product library (NPL-640) or DMSO-control. After 24 and 48 hours of compound treatment supernatant from the cells was collected and TFEB promoter activity determined by quantifying luciferase activity. Panel B) Effects of AIC106 treatment on HLH-30 expression after 24 hours treatment were determined by immunoblot against GFP in young adult stage of GFP-tagged HLH-30 strain (MAH235) following total protein extraction.
Figure 25B:
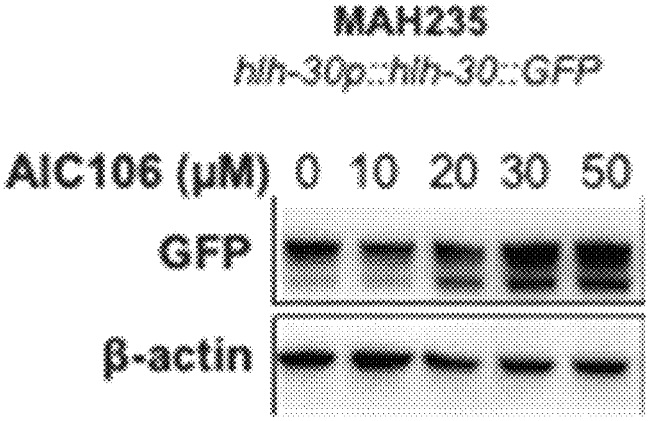

Mammalian TFEB shares significant sequence homology with the *C. elegans* transcription factor HLH-30 (54.2% amino acid sequence identity to mouse TFEB), which itself has been shown to modulate both lifespan and autophagy (Lapierre et al., 2013). We decided therefore to investigate the mechanistic effects of AIC106 utilizing *C. elegans* as a model system. First, using a transgenic reporter expressing GFP tagged HLH-30 protein; we confirmed that AIC106 induces HLH-30 expression in worms (FIG. 18, panels D and E). We validated this by demonstrating increase in HLH-30:GFP protein via immunoblot analysis using a GFP antibody (FIG. 25, panel B). Enhanced HLH-30 expression in AIC106-fed worms was accompanied by enhanced HLH-30 activity, as mRNA levels of several HLH-30 target genes were also increased (FIG. 18, panel F).

Figure 26A:
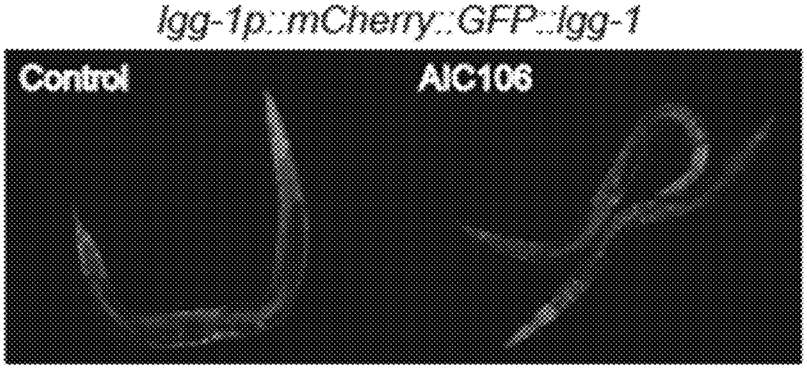
FIG. 26, panels A-B: AIC106 enhances autophagy flux in *C. elegans*. Panel A) Monitoring of tandem reporter lgg-1p::mCherry::GFP::lgg-1 expressing worms was performed by fluorescence microscopy. Panel B) Effects of AIC106 treatment on GFP and mCherry by time were measured by fluorescence microscopy after AIC106 or DMSO-control treatment for 24 h. [N=3 independent experiments (mean±SD). *p<0.05 and **p<0.01, by unpaired t-test].
Figure 26B:
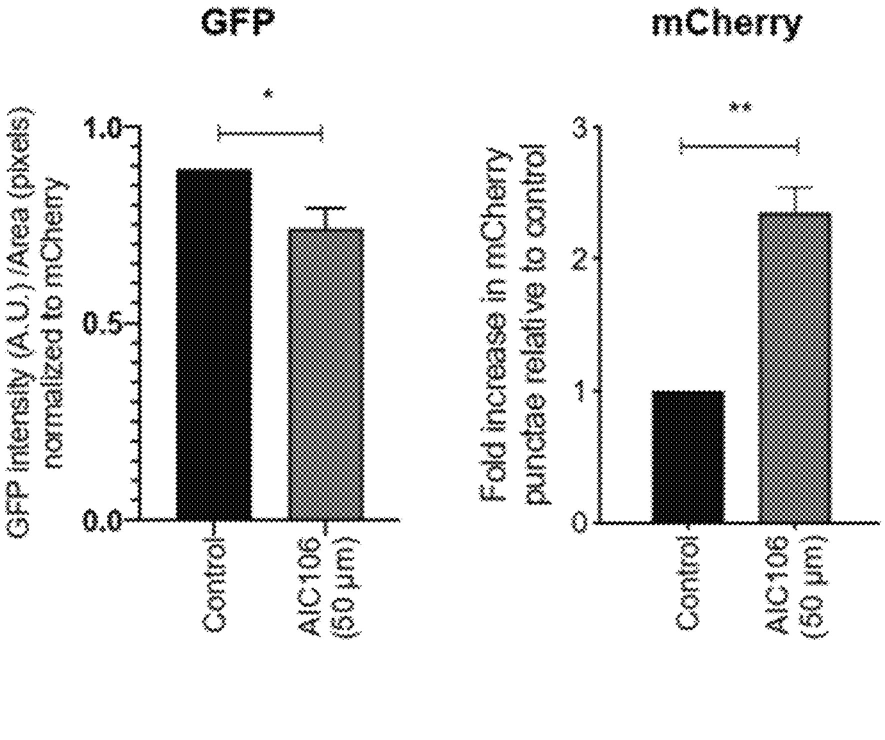

Next, using a strain expressing GFP-tagged p62/SQSTM-1, an autophagosome specific adaptor protein, we quantified autophagic flux in AIC106-treated worms. Based on enhanced GFP expression, AIC106 treatment was found to result in enhanced p62/SQSTM-1 protein levels in the worms (FIG. 19, panels B and C). This increase coincided with increased mRNA levels of p62/Sqstm-1 (FIG. 19, panel A). Post-AIC106 addition, blocking HLH-30 expression via RNAi resulted in increased p62/SQSTM-1 protein levels as indicated by enhanced GFP, despite reductions in levels of p62/Sqstm-1 mRNA (FIG. 19, panel A), indicative of a blockage in the protein's lysosomal degradation. This result suggests that AIC106 induces autophagy and enhances fusion of autophagosomes to lysosomes through the action of HLH-30. To directly monitor autophagosomal-lysosomal fusion, we utilized a transgenic strain expressing autophagosome specific tandem mCherry-GFP-LGG-1 reporter, where GFP fluorescence is pH-sensitive (Chang et al., 2017). Worms treated with AIC106 displayed decreased GFP intensity in conjunction with significant increase in mCherry-only intensity due to degradation of pH-sensitive GFP in the lysosome, consistent with enhanced autophagosomal:lysosomal fusion (FIG. 26, panels A and B). AIC106-treated worms also displayed an increase in lysosomal biogenesis as the expression of the GFP-tagged lysosomal cell surface-specific protein LAMP-1 was enhanced (FIG. 19, panels D and E). This was validated via LysoTracker red staining (FIG. 19, panels F and G). Taken together, these results confirm ability of AIC106 to induce HLH-30 expression and enhance autophagic flux and lysosomal biogenesis in *C. elegans.*

AIC106 Induces Mitophagy and Improves Mitochondrial Capacity in *C. elegans.*

Figure 27A:
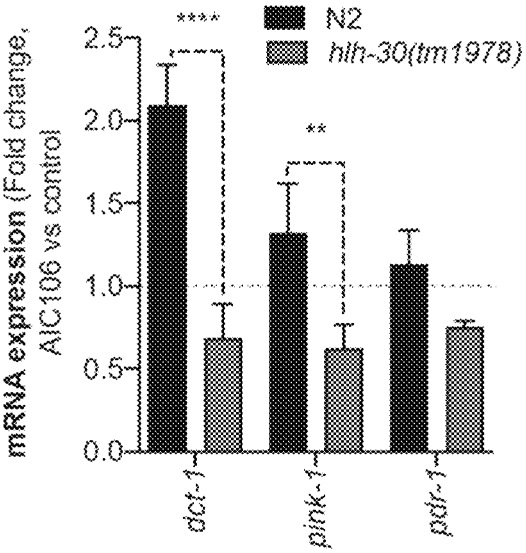
FIG. 27, panels A-C: AIC106 induces mitophagy and increases lifespan. Panel A) Relative fold change in mRNA of key mitophagy genes including dct-1, pink-1 and pdr-1 was quantified by qRT-PCR after DMSO-control and AIC106 24 hours treatment in young adult N2 and hlh-30 (tm1978) mutants. [N=3 independent experiments (mean±SD). p<0.01 and **p<0.0001, by two-way ANOVA with Sidak's multiple comparisons test]. Short exposure (1 week) of AIC106 increased survival of (panel B) wild type N2: DMSO-control (median-12 days), AIC106 50 μM (median-15 days, p<0.0001) and (panel C) mitophagy deficient pdr-1(tm598): mutant DMSO-control (median-15 days), AIC106 50 μM (median −17 days, p<0.001)]. [N=3 independent experiments, P value compared to respective DMSO-control and calculated by Logrank test).
Figure 27B:
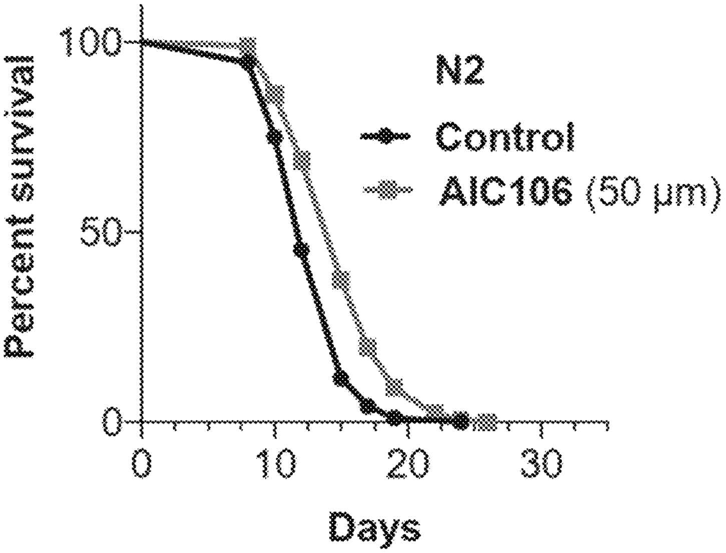
Figure 27C:
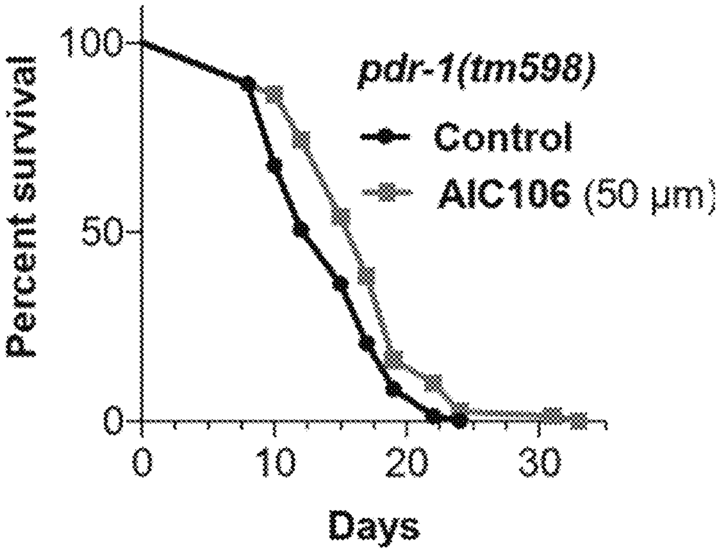

As one of the important beneficial effects of enhanced autophagy flux is its ability to remove damaged mitochondria, we also tested potential of AIC106 to induce mitophagy. One of the initiating steps in mitophagy is depolarization of the mitochondrial membrane potential (MMP). AIC106 treatment was found to result in a significant decrease in the MMP compared to control worms as measured by Tetramethylrhodamine (TMRM) fluorescence (FIG. 20, panels A and B). Consistent with these findings, we also observed elevated mRNA abundance of key mitophagy specific genes including dct-1 and pink-1 in an hlh-30 dependent manner (FIG. 27, panel A). To directly test mitophagy flux, we utilized a worm strain expressing peptide-linked dual fluorescent protein (dFP)-tagged to the mitochondria-specific TOM-7 protein (Chapin et al., 2015). In the presence of lysosomal proteases, dFP is broken down into monomeric-FP (mFP), hence increase in mFP is indicative of enhanced mitochondrial flux to lysosomes. Worms treated with AIC106 show increased mFP expression consistent with enhanced mitophagy (FIG. 20, panel C). We found that worms treated with AIC106 were also more resistant to mitochondrial uncoupler FCCP (FIG. 20, panel D).

We speculated that AIC106 could be beneficial in disease models where mitochondrial function was compromised. We tested AIC106 in a *C elegans* mutant, pdr-1, an ortholog of the human Parkinson's associated gene parkin that is mutated in some familial forms of the disorder (Springer et al., 2005). Parkin is an E3 ubiquitin ligase that associates and cooperates with degradation machinery to mediate ubiquitin conjugation. Worm's mutant for pdr-1 gene display defects in the clearance of damaged mitochondria and, as a consequence, displays enhanced sensitivity towards mitochondrial toxins (FIG. 20, panel E). AIC106 treatment was found to significantly rescue enhanced mitochondrial sensitivity of pdr-1 mutant in an hlh-30 dependent manner (FIG. 20, panel E) consistent with an improvement in the mitochondrial function.

In order to meet increased energy demands, enhanced mitophagy is coupled to mitochondrial biogenesis (Palikaras et al., 2015a, b). To visualize mitochondrial content, we used a strain-expressing mitochondrial targeted-GFP within the intestine (Benedetti et al., 2006). AIC106-treated worms show increased mitochondrial content compared to control worms (FIG. 20, panels F and G). AIC106 treatment was additionally found to increase maximum respiration capacity consistent with the improved mitochondrial function or content (FIG. 20, panel H). This improvement in mitochondrial function was dependent on HLH-30, as hlh-30 mutant worms treated with AIC106 failed to show any increase in the maximum respiration capacity (FIG. 20, panel H). This improvement in mitochondrial function seems to impact overall aging, as short treatment of AIC106 (1 week post-development) was enough to show significant increase in lifespan of both wild type N2 and pdr-1 mutant (FIG. 27, panels B and C). Taken together, these results demonstrate that AIC106 associates and cooperates with a conserved degradation machinery to mediate ubiquitin conjugation and acts to improve mitochondrial health by maintaining the pool of healthy mitochondria.

Figure 28A:
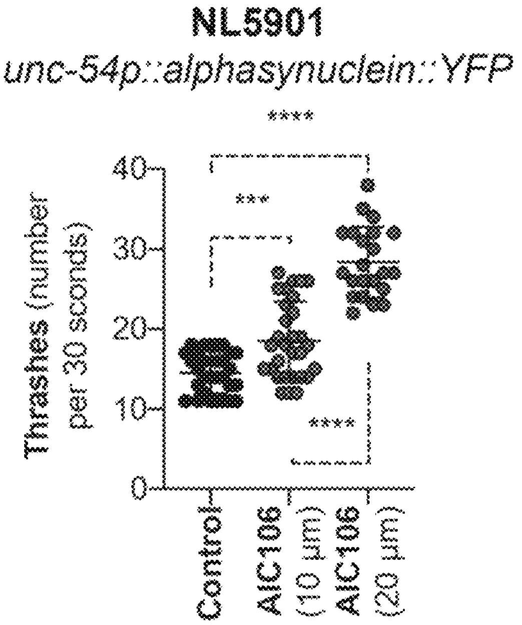
FIG. 28, panels A-B: AIC106 prevents neuronal loss and proteotoxicity in strains expressing human neurotoxic proteins. Panel A) Motor function in day-7 NL5901 were quantified by scoring number of thrashes for an individual worm over the period of 30 seconds (dots) in AIC106 and DMSO-control treatment. [N=3 independent experiments (mean±SD). *p<0.001 and **p<0.0001, by one-way ANOVA with Tukey's multiple comparisons test]. Panel B) Lifespan analysis of CL6049 worms exposed to AIC106 and DMSO-control. [N=2 independent experiments, Treatment (median survival in days, P value compared to DMSO-control): DMSO-control RNAi (18), CL6049-AIC106 control RNAi (21, p<0.0001), CL6049-AIC106 hlh-30 RNAi (17, p<0.0001) and 50 μM (17, p<0.0001). P-value calculated by Logrank test].
Figure 28B:
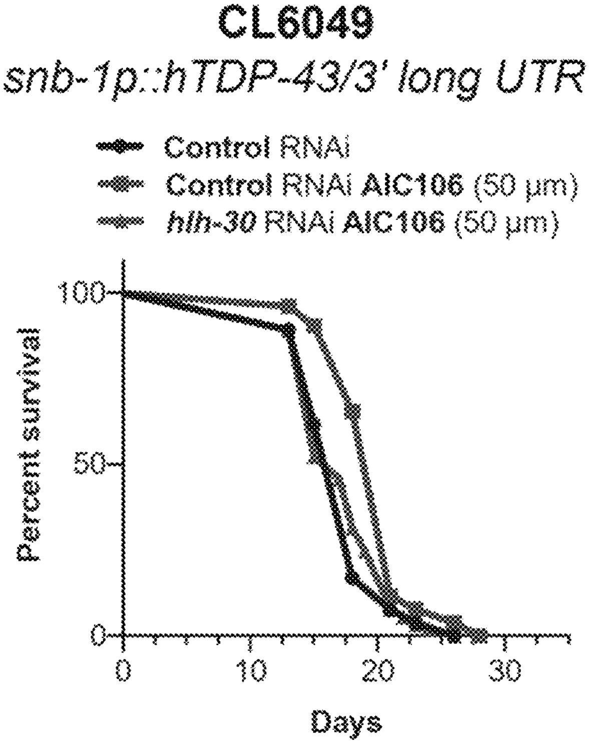

Prevention in Neuronal Loss and Associated Pathologies in Worm Models Expressing Human Neurotoxic Proteins Given the ability of AIC106 to enhance both autophagic flux and to maintain mitochondrial health, we hypothesized that the compound would also likely have beneficial effects in worm strains expressing human neurotoxic proteins. We found AIC106 treatment prevented neuronal loss (FIG. 21, panel A) in a strain expressing human α-synuclein within dopaminergic neurons (Cao et al., 2005). This neuroprotective effect was found to be dependent on HLH-30, as worms treated with hlh-30 RNAi failed to show any neuroprotection (FIG. 21, panel A). AIC106 administration also improved motor function (FIGS. 21, panel B, 28, panel A) in worms expressing human α-synuclein within muscles in an hlh-30 dependent manner as scored by thrashing rate (van Ham et al., 2008). Similar protection against motor (FIG. 21, panels C and D) and neuronal function (FIG. 28, panel C) loss was observed in other strains expressing human Aβ within muscles (Drake et al., 2003; Link, 1995) and GABA neurons (Treusch et al., 2011), respectively. Toxic accumulation of TDP-43 is associated with amylotrophic lateral sclerosis (ALS) disease in humans and its overexpression in worm neurons suppresses lifespan (Ash et al., 2010). We found that AIC106 treatment protected against human TDP-43 toxicity, increasing survival of worms by in a dose dependent manner (FIG. 21, panel E). This increase in lifespan was found to be dependent on hlh-30, as increase in lifespan was completely suppressed in a presence of hlh-30 RNAi (FIG. 28, panel B). Accumulation of poly-glutamine aggregation is a feature of many neurological diseases, the most well-known being Huntington's disease (HD). The number of poly-$Q_{40}$ aggregates within transgenic strains expressing poly-$Q_{40}$ is directly related to the motility (Morley et al., 2002), an important predictor of healthspan (Hahm et al., 2015). AIC106 treatment significantly decreased poly-$Q_{40}$ aggregates in these worms in a dose dependent manner (FIG. 21, panel F). Overall, we found significant beneficial effects of AIC106 treatment in preventing neuronal loss and associated pathologies in worm models expressing human neurotoxic proteins.

AIC106-Induced HLH-30 Expression is Mediated by the Nuclear Hormone Receptor DAF-12

Figure 29B:
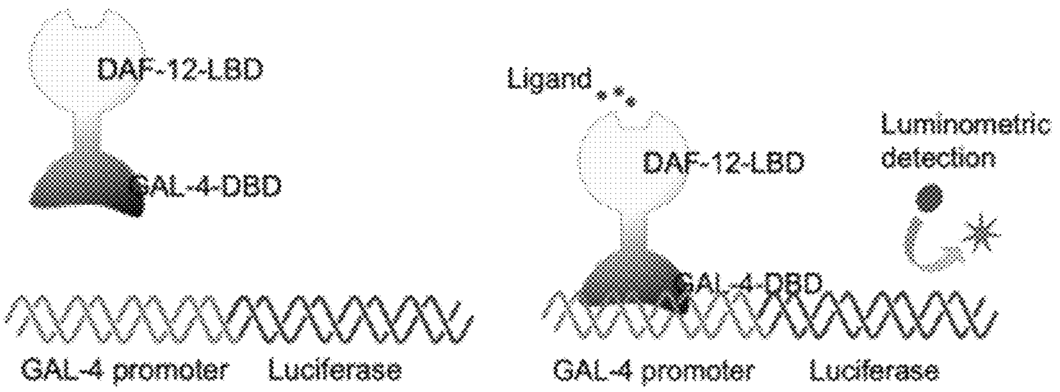
FIG. 29, panels A-C: AIC106 modulates DAF-12 activity. Panel A) Analysis of DAF-12 CHIP data by Hochbaum et al. (Hochbaum et al., 2011) reveals strong DAF-12 binding sites within 2 kb promoter region of many genes involved in autophagy and lysosomal function. Panel B) Schematic of mammalian one-hybrid DAF-12 activity assay. HEK293 cells were transfected with (1) DAF-12 hinge and ligand-binding domains (LBD) fused to the yeast GAL4 DNA binding domain (DBD) and (2) pGL2 vector driving luciferase expression under control of the GAL4 upstream activating sequence (UAS). Luciferase activity was measured to quantify DAF-12 activity. Panel C) Dose dependent increase in DAF-12 activity after treatment with known DAF-12 ligand, dafachronic acid (DA) was determined by quantifying luciferase activity. [N=4 independent experiments (mean±SD). *p<0.001 and **p<0.0001, by one-way ANOVA with Tukey's multiple comparisons test].
Figure 29C:
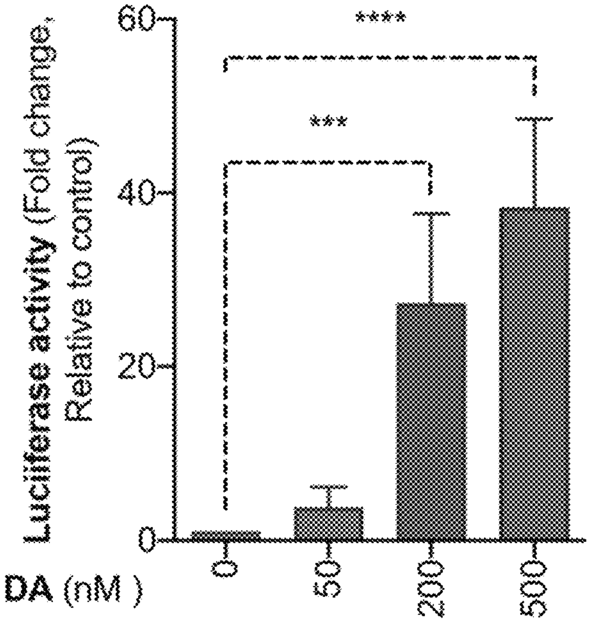

A past study in mammalian hepatocytes reported that during feed-fast cycles, TFEB expression is transcriptionally controlled by a bile acid nuclear hormone receptor, the Farnesoid X receptor (FXR/NR1H4), which in turn regulates autophagic flux (Seok et al., 2014). In worms, FXR shares a close homology with the nuclear hormone receptor DAF-12 (43.5% amino acid sequence identity to mouse FXR/NR1H4). Others and we have previously demonstrated that daf-12 modulates lifespan and reproductive development in worms (Antebi et al., 1998; Fisher and Lithgow, 2006). We interrogated and found the presence of strong DAF-12 binding sites within 2 kb upstream promoter region hlh-30 promoter (FIG. 22, panel A). Analysis of DAF-12 CHIP data by Hochbaum et al. (Hochbaum et al., 2011) also confirms binding of DAF-12 to hlh-30 promoter. Interestingly, not just hlh-30 but many hlh-30 target genes involved in autophagy and lysosomal function show the presence of strong DAF-12 binding sites, with hlh-30 displaying the maximum number of binding sites (FIG. 29, panel A). Therefore, we tested to see whether DAF-12 was required for enhanced HLH-30 expression mediated by AIC106 administration. We found AIC106 failed to induce HLH-30 expression in daf-12(rh61rh411) null mutant (FIG. 22, panel B).

To directly evaluate effect of AIC106 on DAF-12 activity, we tested it in one-hybrid human cell-based DAF-12 activity assay. Specifically, this involved transfection of HEK293T cells with two separate vector constructs containing (FIG. 29, panel B): (1) DAF-12 hinge and ligand-binding domains (LBD) fused to the yeast GAL4 DNA binding domain (DBD) and (2) pGL2 vector driving luciferase expression under control of the GAL4 upstream activating sequence (UAS). In the assay, the known DAF-12 ligand dafachronic acid (DA) (Motola et al., 2006) was found to increase DAF-12 activity in a dose dependent manner, as quantified by enhanced luciferase expression (FIG. 29, panel C). Interestingly, AIC106 treatment did not increase DAF-12 activity but rather resulted in a dose-dependent suppression of DA-induced DAF-12 activity (FIG. 22, panel C). Traditionally, NHRs including DAF-12 regulate expression of their target genes in a manner dependent on the presence or absence of bound ligands. Our results suggested that AIC106 might act to increase HLH-30 expression by acting as a reverse agonist of DAF-12, mimicking a ligand unbound state of the receptor (FIG. 22, panel D).

To this idea further, we employed a specific inhibitor of DAF-12 ligand synthesis, dafadine-A (DFA). DFA is a potent inhibitor of the DAF-9/CYP enzyme, which is essential for the final step in DAF-12 ligand synthesis (Luciani et al., 2011). DFA was found to elicit a significant increase in HLH-30 expression (FIG. 22, panel E). DFA treatment also protected against mitochondrial toxin FCCP (FIG. 22, panel F) and improved motor function of human α-synuclein expressing NL5901 strain (FIG. 22, panel G). We hypothesized that a ligand insensitive mutant of DAF-12 would mimic the beneficial effects of AIC106. We employed CRISPR/CAS-9 mediated engineering of one copy of the daf-12 gene to express ligand-insensitive DAF-12 (Val to Ser mutation of $564^{th}$ amino acid). This manipulation was sufficient to rescue the mitochondrial toxin sensitivity of pdr-1 mutants to almost wild type levels (FIG. 22, panel H).

FXR Modulation Enhances HLH-30 Expression in Human Neuronal SH-SY5Y Cells

Figure 30A:
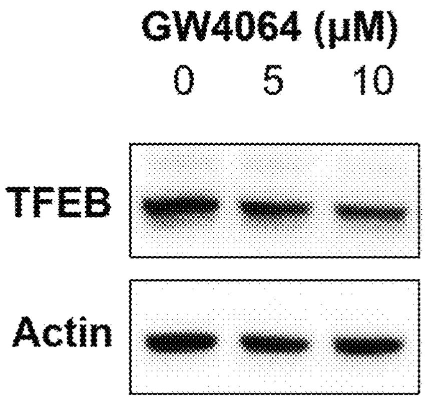
FIG. 30, panels A-B: FXR modulation enhances HLH-30 expression in human neuronal SH-SY5Y cell. Panel A) TFEB expression in SH-SY5Y cells was determined by immunoblot against TFEB in protein lysates collected after 24 hours of treatment with FXR agonist GW4064 and DMSO control. Panel B) Phosphorylated-TAU levels in SH-SY5Y-P301L-TAU cells was determined by immunoblot against (Ser202, Thr205) in protein lysates collected after 24 hours of treatment with known FXR antagonist Z-guggulsterone (z-GG), DY268 and DMSO control.
Figure 30B:
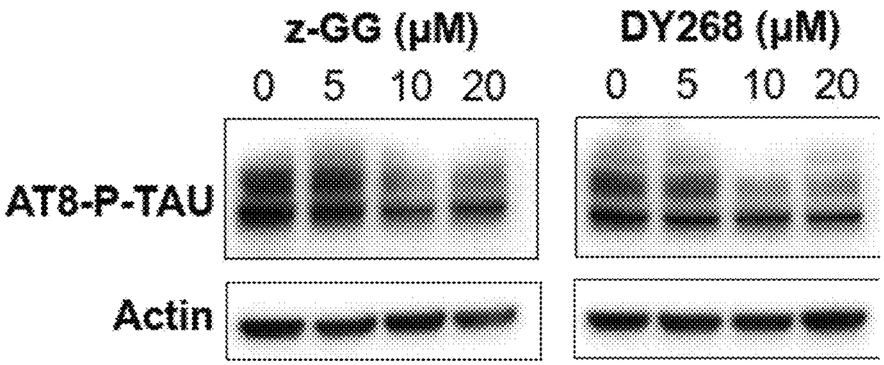

We performed a one-hybrid human cell-based FXR activity assay and confirmed that AIC106 also prevented ligand-induced activation of the human FXR protein (FIG. 23, panel A). AIC106 treatment in human neuronal SH-SY5Y cells resulted in increased expression TFEB protein (FIG. 23, panel B). This increase coincided with enhanced protein expression of TFEB target gene cathepsin D (CATD), involved in lysosomal function and reduced expression of ligand-bound FXR target, small heterodimer partner-1 (SHP-1), suggesting an increase in unbound FXR (FIG. 6B). Down regulation of TFEB in response to ligand-bound FXR is also apparent by reduced TFEB expression in SH-SY5Y cells exposed to the FXR agonist GW4064, which promotes ligand-bound FXR (FIG. 30, panel A) (Goodwin et al., 2000). AIC106 treatment enhanced autophagic flux in human neuronal cells as monitored by quantifying the turnover rate of LC3 protein both in the presence and absence of the autophagy inhibitor bafliomycin A1 (FIG. 23, panel D). Next, we tested neuroprotective role of AIC106 in TSC1+/− human neuronal SH-SY5Y cells, which normally acts as an upstream inhibitor of mTOR activity. Loss in tuberous sclerosis complex, TSC1 function results in selective accumulation of TAU and TAU-phosphorylation leading to cell death (Olney et al., 2017). We found that treating TSC1+/−SH-SY5Y cells with AIC106 results in decrease of phosphorylated-TAU without significantly changing TAU levels (FIG. 23, panels E and F). Physiological we see AIC106 treatment prevented loss in viability and in general health of these cells when differentiated (FIG. 23, panel G). To further confirm the idea that FXR inhibition could suppress accumulation of TAU phosphorylation we tested other known FXR inhibitors DY268 and Z-guugulsterone in human neuronal SH-SySY cells expressing full-length mutant P301L-TAU. We found both DY268 (Yu et al., 2014) and Z-guggulsterone (Urizar et al., 2002) reduced expression of phosphorylated-TAU (FIG. 30, panel B). Overall our findings show potential therapeutic effect of AIC106 in higher mammals and highlights FXR's role in suppressing neurodegeneration.

Discussion

Several recent studies show that autophagic decline in age-related neurodegenerative diseases are closely correlated with reduced expression of the transcription factor TFEB and that TFEB up-regulation protects against neuropathology's associated with these disorders (Cortes et al., 2014; Decressac et al., 2013; Polito et al., 2014; Siddiqui et al., 2015; Torra et al., 2018; Tsunemi et al., 2012; Wang et al., 2016a; Wang et al., 2016b). TFEB up-regulates expression of several genes involved in both autophagy and lysosomal function (Sardiello et al., 2009). Previous small molecule screens have employed autophagic-specific reporters, which, while useful in identifying molecules involved in initiation of autophagy, do not identify compounds acting at the later autophagosomal-lysosomal stage. In order to identify such compounds as potential therapeutics for neurodegenerative diseases, we conducted a small molecule screen utilizing a natural product library to assay for induction of a human TFEB promoter-luciferase construct in the context of in vitro neuronal N27 cells. The top hit from this screen, a coumarin-based compound we called AIC106 (Autophagy Inducing Coumarin), was found to elicit up-regulation of both TFEB gene expression and activity in these same cells. In subsequent experiments, AIC106 was shown to not only significantly enhance autosomal flux and lysosomal function but to improve mitochondrial function and prevent proteotoxicity and neuronal loss in several *C. elegans* models of human neurodegenerative disease. Our experiments in human neuronal SY5Y cells and rat neuronal cells suggest AIC106 is effective in mammals.

Importantly, characterization of AIC106 led us to a novel observation of a role for the nuclear hormone receptor DAF-12/FXR in neuronal HLH-30/TFEB induction. DAF-12 is the most studied nuclear receptor in *C. elegans*, which is expressed in almost all major tissues including neurons and muscles (Antebi et al., 2000). The DAF-12 is involved in regulation of wide variety of *C. elegans* biology including developmental timing, metabolism and longevity making it an important nuclear receptor (Antebi et al., 1998; Fisher and Lithgow, 2006; Wang et al., 2015). HLH-30 has independently been demonstrated to impact lifespan and healthspan via its ability to restore age-related losses in lysosomal autophagy (Lapierre et al., 2013). DAF-12 shares close homology with the human bile acid receptor FXR (Antebi, 2015). AIC106 was confirmed to prevent ligand-mediated FXR activation in human neuronal SH-SY5Y cells as well as the induction of TFEB. Treatment of cells with AIC106 resulted in increased autophagic flux and reduction in insoluble phospho-tau levels in neuronal cells harboring neurodegenerative pathogenic mutation in TSC-1 complex.

Figure 24:
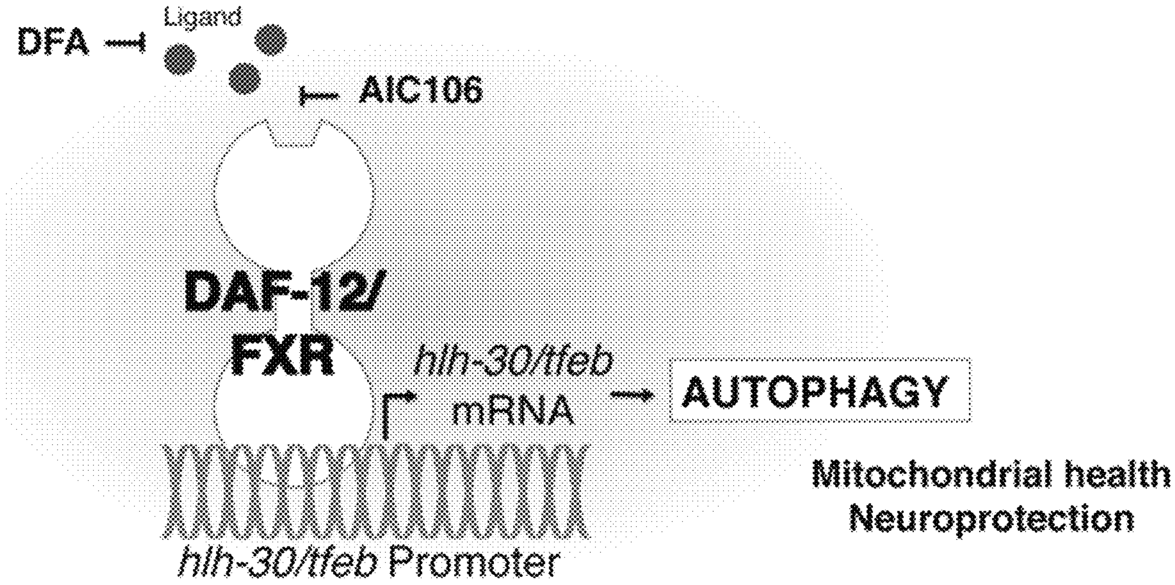
FIG. 24. Modulation of DAF-12/FXR towards ligand-unbound state enhances TFEB-dependent autophagy impacting mitochondrial and neuronal health. Inhibiting DAF-12 ligand synthesis by Dafadine A (DFA) or preventing ligand-induced activation of DAF-12/FXR by AIC106 enhances HLH-30/TFEB expression leading to increased autophagy, improved mitochondrial health and suppression of neurodegeneration.

AIC106 inhibits ligand-induced activity of DAF-12 and requires functional DAF-12 for HLH-30 expression (FIG. 22, panels B and C). These results primarily suggest that it's the presence of ligand-unbound DAF-12/FXR that benefits the organism by inducing autophagy. These results are in line with our previous findings showing that mutant worms carrying ligand-insensitive mutation of daf-12(rh64) are long lived and stress resistance (Fisher and Lithgow, 2006). And on contrary daf-12(rh61rh411) null mutants are short lived and sensitive to thermal and oxidative stresses (Fisher and Lithgow, 2006). Although not established, but autophagy and mitochondrial functions are likely to play an important role in these differences. Evidently, mammalian studies shows that FXR knockout mice are defective in autophagy and their mitochondria are particularly sensitive to stress (Manley et al., 2014a; Manley et al., 2014b). Altogether, we propose a model suggesting that genetic or pharmacological interventions promoting ligand-unbound state of DAF-12/FXR are likely to provide therapeutic benefits in multiple neurodegenerative diseases by inducing autophagy and improving mitochondrial function (FIG. 24).

The known role for mammalian FXR signaling is in maintaining lipid homeostasis in response to circulating bile acids in the liver and gut. FXR is also expressed in other cholesterol-rich tissues including the brain (Huang et al., 2016). This may have important implications for the modulation of FXR beyond its established role in the regulation of cholesterol metabolism. Hepatic encephalopathy in response to peripheral liver injury has been shown to elicit increased uptake of the serum bile acid derivative chenodeoxycholic acid (CDCA) into the brain, resulting in increased FXR expression within neurons (McMillin et al., 2016). This was found to coincide with increased neuronal damage that was prevented by genetic inhibition of FXR expression in vivo.

The known FXR antagonist ursodeoxycholic acid (UDCA) and its taurine derivative TUDCA have been reported to be neuroprotective in both cellular and in vivo models of PD (Abdelkader et al., 2016; Mortiboys et al., 2015; Rosa et al., 2018), including in *C. elegans* (Ved et al., 2005). UDCA is an FDA-licensed drug that has been in clinical use for several decades for treatment of primary biliary cirrhosis and TUDCA is currently undergoing clinical trial for neuromotor disease (Elia et al., 2016; Rudic et al., 2012). Both UDCA and TUDCA are orally available and blood-brain-barrier (BBB) permeable. The mode of action of these compounds in these previous studies was attributed to their antioxidant and anti-apoptotic properties (Rosa et al., 2017). Surprisingly, the possible involvement of FXR in the observed neuroprotection was not considered nor the potential downstream signaling pathways involved. Effects of FXR modulation are likely to be tissue-specific and dependent on disease type and state, pathologic stimuli, and/or energy status (Han, 2018). Results from our studies indicate that neuronal FXR inhibition, via its ability to induce TFEB-mediated autophagy, is protective against neuropathologies associated with age-related neurodegenerative diseases and, as such, may constitute a novel potential therapeutic target for these disorders. It also has important implications for potential off-target effects of systemic FXR agonists as treatments for liver and metabolic diseases in other organs including the brain (Ali et al., 2015).

Experimental Procedures

*C. elegans* Strains

All *C. elegans* strains were maintained under standard laboratory conditions. Unless described otherwise, all experiments were performed at 20° C. All strains used in the study include are (also listed in Key Resources Table): N2 Wild type Bristol isolate, MAH235 sqIs19 [hlh-30p::hlh-30::GFP+rol-6(su1006)], HZ589 him-5(e1490) V; bpIs151 [sqst-1p::sqst-1::GFP+unc-76(+)], RT258 unc-119(ed3) III; pwIs50 [lmp-1::GFP+Cbr-unc-119(+)], MAH215 sqIs11 [lgg-1p::mCherry::GFP:lgg-1+rol-61 JIN1375 hlh-30 (tm1978) IV, N2 Wild type Bristol isolate (control for hlh-30(tm1978) IV), DLM14 ttTi5605 II; unc-119(ed3) III; uwaEx8 [eft-3p::CERULEAN-VENUS::tomm-7+unc-119 (+)], SJ4143 zcIs 17 [ges-1::GFP(mit)], pdr-1(tm598) III, CL2006 dvIs2 [pCL12(unc-54/human Abeta peptide 1-42 minigene)+pRF4], CL4176 smg-1(cc546) I; dvIs27 [myo-3p::A-Beta (1-42)::let-851 3'UTR)+rol-6(su1006)] X, NL5901 pkIs2386 [unc-54p::alphasynuclein::YFP+unc-119 (+)], UA44 UA44(baIn11 [Pdat-1::α-syn, Pdat-1::GFP1), CL6049 dvIs62 [snb-1p::hTDP-43/3' long UTR+mtl-2p::GFP] X, AM141 rmIs133 [unc-54p::Q40::YFP], AA86 daf-12(rh61rh411) X.

Strains generated for the study: PHX569+/szT1[lon-2 (e678)]I; pdr-1(tm598) III; daf-12(syb569)/szT1, PHX835+/szT1[lon-2(e678)]I; pdr-1(tm598) III; szT1/+X, GLXX pdr-1(tm598) III; hlh-30(tm1978) IV Plate Preparation and Compound Treatment NGM agar plates (35 mm) were prepared under sterile conditions in a laminar flow hood at room temperature (22° C.). To these plates, 100 μl of *E. coli* Op50 was added to form a circular bacterial lawn on the center of each plate. Plates were then left inside the hood (lid closed) for drying. A 100 mM stock of compound was prepared in DMSO and stored in small aliquots at −20° C. From the stock solution, 130 μl of the working compound solution (e.g. 100 μM AIC106), was prepared by mixing 3.0 μl of stock solution and 130 μl of sterile water and added to the top of the 35 mm NGM plates (with 3 mL NGM agar) 48 hours post bacterial seeding. Compound was distributed over the entire plate surface and allowed to dry in a sterile hood with the lid open for at least 1 hour. Plates were then allowed to sit at 20° C. for 24 hours before use. For all worm experiments, treatment was performed as follows: a synchronous population of worms was obtained by a 2-hour egg lay from gravid adult hermaphrodites, after which the adults were removed and the eggs left to develop into adults at 20° C. On their first day of adulthood, worms were transferred to DMSO control (0.1%) or compound-treated plates for experiment analysis.

Lifespan Assays

Lifespan assays for CL6049 and pdr-1(tm598) strains was performed after treating day-1 adult worms with DMSO or AIC106. A synchronized 35-40 young day-1 adult worms were transferred to each 35 mm compound-treated plates supplemented with FuDR containing control DMSO or AIC106 and kept at 20° C. Worms were scored as alive, dead, or lost every alternate day. Worms that failed to display touch-provoked movement were scored as dead. Worms that died from causes other than aging, such as sticking to the plate walls, internal hatching of eggs (bagging), or gonadal extrusion were censored as lost. Worms were transferred to fresh-drugged plates every 3-5 days. All lifespan experiments were performed at 20° C.

RNAi Knockdown of Gene Expression

HT115 bacterial RNAi strains expressing double-stranded RNA targeting specific gene were cultured and used as previously described.

Worm Paralysis Assays

Synchronized populations of CL4176 [dvIs27[myo::Aβ (3-42)-let 3'UTR(pAF29); pRF4 (rol-6(su1006))] worms were grown from eggs at 15° C. until the L4 larval stage and then transferred to fresh 35 mm plates treated with compound or DMSO control. Worms were immediately shifted to 25° C. and paralysis was scored 48 hours after the temperature shift. Worms were scored as paralyzed if they failed to move during observation and exhibited 'halos' of cleared bacteria around their heads (indicative of insufficient body movement to access food), eggs accumulated close to the body, or if they failed to respond to touch-provoked movement with a platinum wire.

Thrashing Assay for Motor Function

Synchronized populations of NL5901 pkIs2386 [unc-54p::alphasynuclein::YFP+unc-119 or CL2006 dvIs2 [pCL12(unc-54/human Abeta peptide 1-42 minigene)+pRF4] worms were grown at 20° C. until the young adult larval stage and then transferred to fresh 35 mm FUdR plates treated with compound or DMSO control. Worms were maintained at 20° C. and thrashing was measured at day-6. Thrashing was measured on a sterile unseeded NGM agar plate by transferring a single worm in a 10 μl drop of 1×M9.

The worms were allowed to acclimate to the environment for 30 seconds and then thrashing scored for the next 30 sec. A movement of the worm's head and/or tail to the same side was counted as one thrash. Worm which curls up or do not show any movement were not included in the analysis.

Stress Assays

Synchronized populations of young day-1 adult worms were exposed for 24 hours to compound or DMSO plates supplemented with FuDR. For FCCP stress assay, following 24 hours of compound or DMSO treatment, worms were exposed to FCCP for 1-2 hours in S-basal buffer. Experiments were performed in flat-bottom 96-well plates containing 10-15 worms in 40 μl of S-basal in each well. Worms that failed to display touch-provoked movement were scored as dead.

Microscopy and Fluorescence Quantification

Synchronized populations of day-1 adult worms expressing reporter GFP transgene or stained with a dye/stain (Lysotracker and TMRM) and grown at 20° C. were transferred to compound or DMSO plates. Fluorescence expression was analyzed at the time specified for each individual strain (see figure legends). Worms were paralyzed in 2 mM levamisole, mounted on 2% agarose pads with glass cover slips, and imaged immediately with an Axio Zeiss microscope. Appropriate filters were used to visualize GFP, Lysotracker red and TMRM were visualized under rhodamine filter. Approximately 20-40 worms per treatment were used. Fluorescence intensity normalized to worm area was measured using NIH ImageJ software. Transgenic reporters used in the study are HZ589 him-5(e1490) V; bpIs151[sqst-1p::sqst-1::GFP+unc-76(+)], RT258 unc-119(ed3) III; pwIs50 [lmp-1::GFP+Cbr-unc-119(+)], UA44 UA44 (baIn11[Pdat-1::α-syn, Pdat-1::GFP]), AM141 rmIs133 [unc-54p::Q40::YFP]LAMP-1:GFP.

Lysotracker Red Staining

Synchronized day-1 adult N2 worms were transferred to DMSO control or compound treated plates for 24 hours at 20° C. On day-2, worms were transferred to 35 mm OP50 seeded assay plates treated with compound or DMSO plates overlaid with 1 μM LysoTracker™ Red DND-99 (Molecular Probes) for 24 hours at 20° C. Post-24 hours on LysoTracker stain, worms were picked and washed in a fresh drop of 1×M9 medium to remove excess stain and mounted on 2% agarose pad slides for microscopic visualization. Worm images were taken in a Zeiss Imager Z1 fluorescence microscope using rhodamine filters. Image analysis was performed by measuring mean LysoTracker fluorescence of each worm using Image J (NIH) software.

Measurement of Mitochondrial Membrane Potential Using Tetramethylrhodamine (TMRM)

Synchronized day-1 adult N2 worms were transferred to DMSO control or compound treated plates for 24 hours at 20° C. On day-2, worms were transferred to 35 mm OP50 seeded assay plates treated with compound or DMSO overlaid with 150 nM of TMRM for 24 hours at 20° C. covered in a aluminum foil (TMRM is light sensitive). Post-24 hours worms were transferred to non-TMRM compound plates for at least 1 hour to remove any excess TMRM attached to body from outside. About 20-40 worms per condition were prepared for imaging and imaged under Axio Zeiss fluorescence microscope using rhodamine filter. TMRM intensity was measured using NIH ImageJ software and plotted as fluorescence intensity normalized to worm area.

RNA Isolation and Quantitative Real-Time PCR (qRT-PCR) from *C. elegans*

RNA was isolated from 200 day-1 adult worms treated with compound or DMSO control and grown at 20° C. The worms were washed with 1×M9 buffer to get rid of any attached bacteria and finally collected in 300 μL of RNA lysis buffer supplied with a Zymogen RNA isolation kit. RNA was isolated according to the supplier protocol. The RNA concentration was quantified using NanoDrop 2000 Spectrophotometer. A total of 1000 ng RNA was subsequently reverse-transcribed to cDNA using iScript cDNA Synthesis Kit. Real time PCR was then performed using SYBR green master mix (PCR condition xxxx) in a Light cycler 480II system. The relative gene expression was calculated by $2^{-\Delta\Delta Ct}$ method. The sequence of the qRT primers used for the analysis is provided in a table 1 and were obtained from the previously published study.

Worm Protein Lysate Preparation and Western Blot Analysis

Synchronized day-1 adult N2 worms were transferred to compound or DMSO control treated plates at 20° C. Following compound exposure, 100 worms from each treatment condition were collected in 1×M9 solution. Worms were washed twice to remove any attached bacteria and suspended in 50 μL RIPA lysis buffer supplied with protease inhibitor cocktail. To prepare protein lysates, worm pellets were sonicated for 10 cycles at maximum intensity in a Bioruptor® (Diagenode). Lysates were then centrifuged at 1000 g for 1 minute to pellet debris and the supernatant transferred to a fresh tube. Protein quantification was performed and proteins of interest were analyzed by running lysate on a denaturing SDS-PAGE gel followed by transfer to a nitrocellulose membrane. Pixel intensity of the protein bands was quantified using NIH Image J software.

Mammalian One-Hybrid Assay to Measure DAF-12 Activity

HEK293T cells were transfected and treated with DAF-12 agonist dafachronic acid alone or in combination with AIC106. Co-transfections were performed in 96-well plates using 13 ng of pBIND-DAF-12, 12 ng pMAX GFP, 40 ng pG5Luc reporter (Promega, Corp) and control plasmid to maintain 100 ng/well. Twenty-four hours after transfection the medium was replaced with DMEM+10% charcoal stripped fetal bovine serum (Life Technologies). Positive control dafachronic acid (Sigma) was added alone or in combination with AIC106 in triplicate. After 24 hours, cells were lysed and GFP fluorescence was measured using Perkin Elmer Universal microplate analyzer Fusion-Alpha FPHT (Perkin Elmer). Luciferase activity was measured in the Enspire 2300 Multi label Reader (Perkin Elmer) using the Luciferase Assay System (Promega Corp.). Luciferase activity was normalized to the GFP values. Results are expressed as mean+SEM for three experiments.

Measurement of Oxygen Consumption Rate (OCR)

Statistic analysis: p-value legends (*$p \leq 0.05$, $p \leq 0.01$, *$p \leq 0.001$, ****$p \leq 0.0001$, ns—not significant)

Cell Lines and Culture Conditions

The rat dopaminergic cell line $1RB_3AN_{27}$ (N27) was grown in RPMI 1640 medium supplemented with 10% fetal calf serum (Invitrogen), 100 U/ml penicillin, and 100 μg/ml streptomycin. SH-SY5Y TSC1+/− lines were generated as described previously (Olney et al., 2017). Briefly, the SH-SY5Y neuroblastoma cell line (ATCC, #CRL-2266), was subjected to lentiviral CRISPR/Cas9 genome editing of the TSC1 locus (Doudna and Charpentier, 2014; Sanjana et al., 2014; Shalem et al., 2014). Targeted single RNA guide (gRNA) sequence against the exon 3 of the TSC1 gene (5'-GGCCCAACAAGCAAATGTCG-3', SEQ ID NO:13) was introduced into the LentiCRISPRv2 (addgene 52961) vector following the lentiviral CRISPR plasmid generation protocol (Shalem et al., 2014). Lentivirus particles were produced by co-transfection of the LentiCRISPRv2 plasmid containing the gRNA sequence with the packaging plasmids psPAX2 (AddGene 12260) and pCMV-VSV-G (AddGene 18454) into HEK293FT. Then, SH-SY5Y cells were infected with virus particles and, after the antibiotic selection, individual clones were isolated, expanded and sequenced. Once generated, the TSC1+/− cells were cultured in EMEM:F12 medium supplemented with 10% (v/v) heat-inactivated fetal bovine serum (FBS) and 1% penicillin/streptomycin.

SH-SY5Y Neuronal Differentiation

SH-SY5Y cell lines were differentiated into neurons by treatment with 10 μM of retinoic acid (RA) for 6 days in EMEN/F12 media supplemented with 10% of FBS and 1% Penicillin-Streptomycin, followed by another 4 days of treatment with 50 ng/mL of BDNF in EMEN/F12 media supplemented only with 1% Penicillin-Streptomycin (Encinas et al., 2000).

Treatments, Cell Lysates and Western Blotting

After RA-induced neuronal differentiation, control and TSC1+/−SH-SY5Y cells were treated with 10 uM of compound xx for 72 hours. Then, cell lysates were collected using 1×RIPA buffer (Thermo Scientifics) supplemented with a cocktail of proteases and phosphatases inhibitors (Roche). Total protein concentration was quantified using Pierce™ BCA Protein Assay kit (Thermo Scientifics). Proteins were separated using Novex NuPage SDS-Page gel system (Thermo Scientifics followed by western blot using antibodies against anti-human tau HT7 (Thermo Scientific, #MN1000, 1:500) and monoclonal mouse anti-tau phospho-Ser396/Ser404 (PHF-1) (Peter Davies lab, Litwin Zucker Center for Alzheimer's Research, Long Island, USA, 1:500), LC3B (Sigma, 1:500) and Lamp2 (Lamp 2 H4B4, DSHB, 1:1000). Imaging and quantification of the band intensity was performed on a LI-COR Odyssey Infrared System. Three biological replicates were performed for each experiments and results were averaged for quantification. Statistical analyses were performed with Graph Pad Prism 6 (La Jolla, CA, USA). All the statistical data are presented as mean±standard error of the mean (SEM). Statistical significance was estimated by two-way analysis of variance (ANOVA) followed by the Bonferroni's test for multiple comparisons. A value of $p \leq 0.05$ was considered significant.

Human FXR Antagonist Reporter Assay:

Antagonistic activity of the AIC106 on human FXR was determined using a commercially available FXR Human reporter assay kit (Cayman) according to the supplied manual. Briefly, reporter cells provided in the kit were plated in a 96-well plate. After 24 hours cells were treated with the known agonist GW4064 alone or in combination with AIC106. Luminescence was quantified. Average Relative Light Units (RLU) and corresponding standard deviation was determined for each condition and values are represented as fold changes with respect to no treatment control.

REFERENCES

Abdelkader, N. F., Safar, M. M., and Salem, H. A. (2016). Ursodeoxycholic Acid Ameliorates Apoptotic Cascade in the Rotenone Model of Parkinson's Disease: Modulation of Mitochondrial Perturbations. Mol Neurobiol 53, 810-817.

Ali, A. H., Carey, E. J., and Lindor, K. D. (2015). Recent advances in the development of farnesoid X receptor agonists. Ann Transl Med 3, 5.

Anding, A. L., and Baehrecke, E. H. (2017). Cleaning House: Selective Autophagy of Organelles. Dev Cell 41, 10-22.

Antebi, A. (2015). Nuclear receptor signal transduction in *C. elegans* (Jun. 9, 2015), WormBook, ed. The *C. elegans* Research Community, WormBook, WormBook, ed. edn.

Antebi, A., Culotti, J. G., and Hedgecock, E. M. (1998). daf-12 regulates developmental age and the dauer alternative in *Caenorhabditis elegans*. Development 125, 1191-1205.

Antebi, A., Yeh, W. H., Tait, D., Hedgecock, E. M., and Riddle, D. L. (2000). daf-12 encodes a nuclear receptor that regulates the dauer diapause and developmental age in *C. elegans*. Genes Dev 14, 1512-1527.

Arias, E., and Cuervo, A. M. (2011). Chaperone-mediated autophagy in protein quality control. Curr Opin Cell Biol 23, 184-189.

Ash, P. E., Zhang, Y. J., Roberts, C. M., Saldi, T., Hatter, H., Buratti, E., Petrucelli, L., and Link, C. D. (2010). Neurotoxic effects of TDP-43 overexpression in *C. elegans*. Hum Mol Genet 19, 3206-3218.

Benedetti, C., Haynes, C. M., Yang, Y., Harding, H. P., and Ron, D. (2006). Ubiquitin-like protein 5 positively regulates chaperone gene expression in the mitochondrial unfolded protein response. Genetics 174, 229-239.

Buszczak, M., and Kramer, H. (2019). Autophagy Keeps the Balance in Tissue Homeostasis. Dev Cell 49, 499-500.

Cao, S., Gelwix, C. C., Caldwell, K. A., and Caldwell, G. A. (2005). Torsin-mediated protection from cellular stress in the dopaminergic neurons of *Caenorhabditis elegans*. J Neurosci 25, 3801-3812.

Chang, J. T., Kumsta, C., Hellman, A. B., Adams, L. M., and Hansen, M. (2017). Spatiotemporal regulation of autophagy during *Caenorhabditis elegans* aging. Elife 6.

Chapin, H. C., Okada, M., Merz, A. J., and Miller, D. L. (2015). Tissue-specific autophagy responses to aging and stress in *C. elegans*. Aging (Albany NY) 7, 419-434.

Clarke, A. J., and Simon, A. K. (2019). Autophagy in the renewal, differentiation and homeostasis of immune cells. Nat Rev Immunol 19, 170-183.

Cortes, C. J., Miranda, H. C., Frankowski, H., Batlevi, Y., Young, J. E., Le, A., Ivanov, N., Sopher, B. L., Carromeu, C., Muotri, A. R., et al. (2014). Polyglutamine-expanded androgen receptor interferes with TFEB to elicit autophagy defects in SBMA. Nat Neurosci 17, 1180-1189.

Cuervo, A. M. (2008). Autophagy and aging: keeping that old broom working. Trends Genet 24, 604-612.

Decressac, M., Mattsson, B., Weikop, P., Lundblad, M., Jakobsson, J., and Bjorklund, A. (2013). TFEB-mediated autophagy rescues midbrain dopamine neurons from alpha-synuclein toxicity. Proc Natl Acad Sci USA 110, E1817-1826.

Di Malta, C., Cinque, L., and Settembre, C. (2019). Transcriptional Regulation of Autophagy: Mechanisms and Diseases. Front Cell Dev Biol 7, 114.

Drake, J., Link, C. D., and Butterfield, D. A. (2003). Oxidative stress precedes fibrillar deposition of Alzheimer's disease amyloid beta-peptide (1-42) in a transgenic *Caenorhabditis elegans* model. Neurobiol Aging 24, 415-420.

Elia, A. E., Lalli, S., Monsurro, M. R., Sagnelli, A., Taiello, A. C., Reggiori, B., La Bella, V., Tedeschi, G., and Albanese, A. (2016). Tauroursodeoxycholic acid in the treatment of patients with amyotrophic lateral sclerosis. Eur J Neurol 23, 45-52.

Fisher, A. L., and Lithgow, G. J. (2006). The nuclear hormone receptor DAF-12 has opposing effects on *Cae-*

*norhabditis elegans* lifespan and regulates genes repressed in multiple long-lived worms. Aging Cell 5, 127-138.
Goodwin, B., Jones, S. A., Price, R. R., Watson, M. A., McKee, D. D., Moore, L. B., Galardi, C., Wilson, J. G., Lewis, M. C., Roth, M. E., et al. (2000). A regulatory cascade of the nuclear receptors FXR, SHP-1, and LRH-1 represses bile acid biosynthesis. Mol Cell 6, 517-526.
Hahm, J. H., Kim, S., DiLoreto, R., Shi, C., Lee, S. J., Murphy, C. T., and Nam, H. G. (2015). *C. elegans* maximum velocity correlates with healthspan and is maintained in worms with an insulin receptor mutation. Nat Commun 6, 8919.
Han, C. Y. (2018). Update on FXR Biology: Promising Therapeutic Target? Int J Mol Sci 19.
Hochbaum, D., Zhang, Y., Stuckenholz, C., Labhart, P., Alexiadis, V., Martin, R., Knolker, H. J., and Fisher, A. L. (2011). DAF-12 regulates a connected network of genes to ensure robust developmental decisions. PLoS Genet 7, e1002179.
Huang, C., Wang, J., Hu, W., Wang, C., Lu, X., Tong, L., Wu, F., and Zhang, W. (2016). Identification of functional farnesoid X receptors in brain neurons. FEBS Lett 590, 3233-3242.
Lapierre, L. R., De Magalhaes Filho, C. D., McQuary, P. R., Chu, C. C., Visvikis, O., Chang, J. T., Gelino, S., Ong, B., Davis, A. E., Irazoqui, J. E., et al. (2013). The TFEB orthologue HLH-30 regulates autophagy and modulates longevity in *Caenorhabditis elegans*. Nat Commun 4, 2267.
Leidal, A. M., Levine, B., and Debnath, J. (2018). Autophagy and the cell biology of age-related disease. Nat Cell Biol 20, 1338-1348.
Levine, B., and Kroemer, G. (2019). Biological Functions of Autophagy Genes: A Disease Perspective. Cell 176, 11-42.
Levine, B., Mizushima, N., and Virgin, H. W. (2011). Autophagy in immunity and inflammation. Nature 469, 323-335.
Levine, B., Packer, M., and Codogno, P. (2015). Development of autophagy inducers in clinical medicine. J Clin Invest 125, 14-24.
Link, C. D. (1995). Expression of human beta-amyloid peptide in transgenic *Caenorhabditis elegans*. Proc Natl Acad Sci USA 92, 9368-9372.
Luciani, G. M., Magomedova, L., Puckrin, R., Urbanus, M. L., Wallace, I. M., Giaever, G., Nislow, C., Cummins, C. L., and Roy, P. J. (2011). Dafadine inhibits DAF-9 to promote dauer formation and longevity of *Caenorhabditis elegans*. Nat Chem Biol 7, 891-893.
Manley, S., Ni, H. M., Kong, B., Apte, U., Guo, G., and Ding, W. X. (2014a). Suppression of autophagic flux by bile acids in hepatocytes. Toxicol Sci 137, 478-490.
Manley, S., Ni, H. M., Williams, J. A., Kong, B., DiTacchio, L., Guo, G., and Ding, W. X. (2014b). Farnesoid X receptor regulates forkhead Box O3a activation in ethanol-induced autophagy and hepatotoxicity. Redox Biol 2, 991-1002.
Marino, G., Madeo, F., and Kroemer, G. (2011). Autophagy for tissue homeostasis and neuroprotection. Curr Opin Cell Biol 23, 198-206.
Martini-Stoica, H., Xu, Y., Ballabio, A., and Zheng, H. (2016). The Autophagy-Lysosomal Pathway in Neurodegeneration: A TFEB Perspective. Trends Neurosci 39, 221-234.
McMillin, M., Frampton, G., Quinn, M., Ashfaq, S., de los Santos, M., 3rd, Grant, S., and DeMorrow, S. (2016). Bile Acid Signaling Is Involved in the Neurological Decline in a Murine Model of Acute Liver Failure. Am J Pathol 186, 312-323.
Mizushima, N., and Levine, B. (2010). Autophagy in mammalian development and differentiation. Nat Cell Biol 12, 823-830.
Morley, J. F., Brignull, H. R., Weyers, J. J., and Morimoto, R. I. (2002). The threshold for polyglutamine-expansion protein aggregation and cellular toxicity is dynamic and influenced by aging in *Caenorhabditis elegans*. Proc Natl Acad Sci USA 99, 10417-10422.
Mortiboys, H., Furmston, R., Bronstad, G., Aasly, J., Elliott, C., and Bandmann, O. (2015). UDCA exerts beneficial effect on mitochondrial dysfunction in LRRK2(G2019S) carriers and in vivo. Neurology 85, 846-852.
Motola, D. L., Cummins, C. L., Rottiers, V., Sharma, K. K., Li, T., Li, Y.,
Suino-Powell, K., Xu, H. E., Auchus, R. J., Antebi, A., et al. (2006). Identification of ligands for DAF-12 that govern dauer formation and reproduction in *C. elegans*. Cell 124, 1209-1223.
Nakamura, S., and Yoshimori, T. (2017). New insights into autophagosome-lysosome fusion. *J Cell Sci* 130, 1209-1216.
Napolitano, G., Esposito, A., Choi, H., Matarese, M., Benedetti, V., Di Malta, C., Monfregola, J., Medina, D. L., Lippincott-Schwartz, J., and Ballabio, A. (2018). mTOR-dependent phosphorylation controls TFEB nuclear export. Nat Commun 9, 3312.
Olney, N. T., Alquezar, C., Ramos, E. M., Nana, A. L., Fong, J. C., Karydas, A. M., Taylor, J. B., Stephens, M. L., Argouarch, A. R., Van Berlo, V. A., et al. (2017). Linking tuberous sclerosis complex, excessive mTOR signaling, and age-related neurodegeneration: a new association between TSC1 mutation and frontotemporal dementia. Acta Neuropathol 134, 813-816.
Palikaras, K., Lionaki, E., and Tavernarakis, N. (2015a). Coordination of mitophagy and mitochondrial biogenesis during ageing in *C. elegans*. Nature 521, 525-528.
Palikaras, K., Lionaki, E., and Tavernarakis, N. (2015b). Coupling mitogenesis and mitophagy for longevity. Autophagy 11, 1428-1430.
Pan, T., Kondo, S., Le, W., and Jankovic, J. (2008). The role of autophagy-lysosome pathway in neurodegeneration associated with Parkinson's disease. Brain 131, 1969-1978.
Panda, P. K., Fahrner, A., Vats, S., Seranova, E., Sharma, V., Chipara, M., Desai, P., Torresi, J., Rosenstock, T., Kumar, D., et al. (2019). Chemical Screening Approaches Enabling Drug Discovery of Autophagy Modulators for Biomedical Applications in Human Diseases. Front Cell Dev Biol 7, 38.
Polito, V. A., Li, H., Martini-Stoica, H., Wang, B., Yang, L., Xu, Y., Swartzlander, D. B., Palmieri, M., di Ronza, A., Lee, V. M., et al. (2014). Selective clearance of aberrant tau proteins and rescue of neurotoxicity by transcription factor EB. EMBO Mol Med 6, 1142-1160.
Rabinowitz, J. D., and White, E. (2010). Autophagy and metabolism. Science 330, 1344-1348.
Rosa, A. I., Duarte-Silva, S., Silva-Fernandes, A., Nunes, M. J., Carvalho, A. N., Rodrigues, E., Gama, M. J., Rodrigues, C. M. P., Maciel, P., and Castro-Caldas, M. (2018). Tauroursodeoxycholic Acid Improves Motor Symptoms in a Mouse Model of Parkinson's Disease. Mol Neurobiol 55, 9139-9155.
Rosa, A. I., Fonseca, I., Nunes, M. J., Moreira, S., Rodrigues, E., Carvalho, A. N., Rodrigues, C. M. P., Gama, M.

J., and Castro-Caldas, M. (2017). Novel insights into the antioxidant role of tauroursodeoxycholic acid in experimental models of Parkinson's disease. Biochim Biophys Acta Mol Basis Dis 1863, 2171-2181.

Rubinsztein, D. C., Marino, G., and Kroemer, G. (2011). Autophagy and aging. Cell 146, 682-695.

Rudic, J. S., Poropat, G., Krstic, M. N., Bjelakovic, G., and Gluud, C. (2012). Ursodeoxycholic acid for primary biliary cirrhosis. Cochrane Database Syst Rev 12, CD000551.

Sardiello, M., Palmieri, M., di Ronza, A., Medina, D. L., Valenza, M., Gennarino, V. A., Di Malta, C., Donaudy, F., Embrione, V., Polishchuk, R. S., et al. (2009). A gene network regulating lysosomal biogenesis and function. Science 325, 473-477.

Seok, S., Fu, T., Choi, S. E., Li, Y., Zhu, R., Kumar, S., Sun, X., Yoon, G., Kang, Y., Zhong, W., et al. (2014). Transcriptional regulation of autophagy by an FXR-CREB axis. Nature 516, 108-111.

Siddiqui, A., Bhaumik, D., Chinta, S. J., Rane, A., Rajagopalan, S., Lieu, C. A., Lithgow, G. J., and Andersen, J. K. (2015). Mitochondrial Quality Control via the PGC1alpha-TFEB Signaling Pathway Is Compromised by Parkin Q311X Mutation But Independently Restored by Rapamycin. J Neurosci 35, 12833-12844.

Song, J. X., Sun, Y. R., Peluso, I., Zeng, Y., Yu, X., Lu, J. H., Xu, Z., Wang, M. Z., Liu, L. F., Huang, Y. Y., et al. (2016). A novel curcumin analog binds to and activates TFEB in vitro and in vivo independent of MTOR inhibition. Autophagy 12, 1372-1389.

Springer, W., Hoppe, T., Schmidt, E., and Baumeister, R. (2005). A *Caenorhabditis elegans* Parkin mutant with altered solubility couples alpha-synuclein aggregation to proteotoxic stress. Hum Mol Genet 14, 3407-3423.

Torra, A., Parent, A., Cuadros, T., Rodriguez-Galvan, B., Ruiz-Bronchal, E., Ballabio, A., Bortolozzi, A., Vila, M., and Bove, J. (2018). Overexpression of TFEB Drives a Pleiotropic Neurotrophic Effect and Prevents Parkinson's Disease-Related Neurodegeneration. Mol Ther 26, 1552-1567.

Treusch, S., Hamamichi, S., Goodman, J. L., Matlack, K. E., Chung, C. Y., Baru, V., Shulman, J. M., Parrado, A., Bevis, B. J., Valastyan, J. S., et al. (2011). Functional links between Abeta toxicity, endocytic trafficking, and Alzheimer's disease risk factors in yeast. Science 334, 1241-1245.

Tsunemi, T., Ashe, T. D., Morrison, B. E., Soriano, K. R., Au, J., Roque, R. A., Lazarowski, E. R., Damian, V. A., Masliah, E., and La Spada, A. R. (2012). PGC-1alpha rescues Huntington's disease proteotoxicity by preventing oxidative stress and promoting TFEB function. Sci Transl Med 4, 142ra197.

Urizar, N. L., Liverman, A. B., Dodds, D. T., Silva, F. V., Ordentlich, P., Yan, Y., Gonzalez, F. J., Heyman, R. A., Mangelsdorf, D. J., and Moore, D. D. (2002). A natural product that lowers cholesterol as an antagonist ligand for FXR. Science 296, 1703-1706.

van Ham, T. J., Thijssen, K. L., Breitling, R., Hofstra, R. M., Plasterk, R. H., and Nollen, E. A. (2008). *C. elegans* model identifies genetic modifiers of alpha-synuclein inclusion formation during aging. PLoS Genet 4, e1000027.

Ved, R., Saha, S., Westlund, B., Perier, C., Burnam, L., Sluder, A., Hoener, M., Rodrigues, C. M., Alfonso, A., Steer, C., et al. (2005). Similar patterns of mitochondrial vulnerability and rescue induced by genetic modification of alpha-synuclein, parkin, and DJ-1 in *Caenorhabditis elegans*. J Biol Chem 280, 42655-42668.

Wang, C., Niederstrasser, H., Douglas, P. M., Lin, R., Jaramillo, J., Li, Y., Oswald, N. W., Zhou, A., McMillan, E. A., Mendiratta, S., et al. (2017). Small-molecule TFEB pathway agonists that ameliorate metabolic syndrome in mice and extend *C. elegans* lifespan. Nat Commun 8, 2270.

Wang, H., Wang, R., Carrera, I., Xu, S., and Lakshmana, M. K. (2016a). TFEB Overexpression in the P301S Model of Tauopathy Mitigates Increased PHF1 Levels and Lipofuscin Puncta and Rescues Memory Deficits. eNeuro 3.

Wang, H., Wang, R., Xu, S., and Lakshmana, M. K. (2016b). Transcription Factor EB Is Selectively Reduced in the Nuclear Fractions of Alzheimer's and Amyotrophic Lateral Sclerosis Brains. Neurosci J 2016, 4732837.

Wang, Z., Stoltzfus, J., You, Y. J., Ranjit, N., Tang, H., Xie, Y., Lok, J. B., Mangelsdorf, D. J., and Kliewer, S. A. (2015). The nuclear receptor DAF-12 regulates nutrient metabolism and reproductive growth in nematodes. PLoS Genet 11, e1005027.

Yu, D. D., Lin, W., Forman, B. M., and Chen, T. (2014). Identification of trisubstituted-pyrazol carboxamide analogs as novel and potent antagonists of farnesoid X receptor. Bioorg Med Chem 22, 2919-2938.

Zhang, L., Huang, R., Ding, W. X., and Xia, M. (2019). Abstract 985: Development and validation of cell-based TFEB translocation assay in a high-content and high-throughput screening format. Cancer Research 79, 985-985.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of promoting autophagy in cells, said method comprising:

contacting said cells with an effective amount of one or more compounds that promote autophagy, where said compounds are selected from the group consisting of 2,3,6,7,10,11-Hexahydro-1H,5H-cyclopenta(3,4)(1)benzopyrano(6,7,8-ij)quinolizin-12(9H)-one (Coumarin 106; CAS Registry No. 41175-45-5, also known as AIC106), (C3)

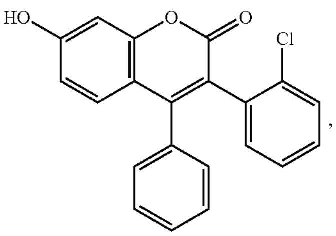

-continued (H2)

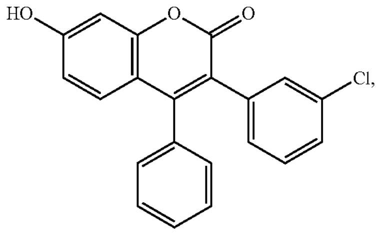

(F2)

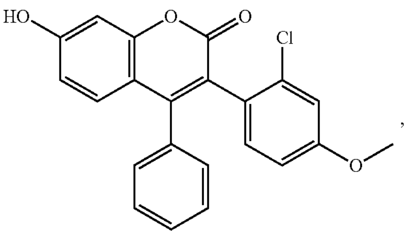

-continued
(D3)
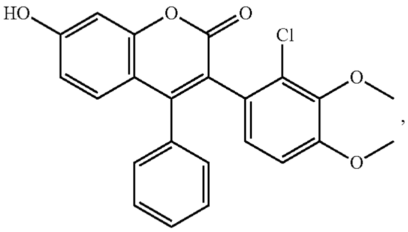
(G2)
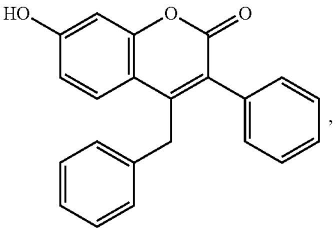
(A3)
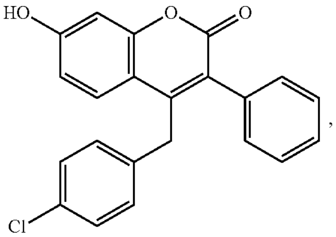
(C2)
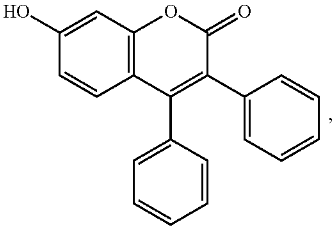
(A2)
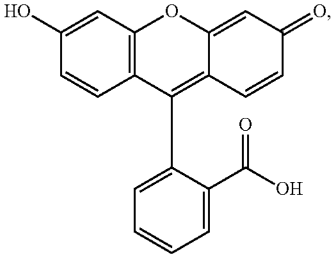
(A5)
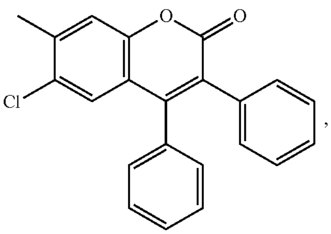
-continued
(D5)
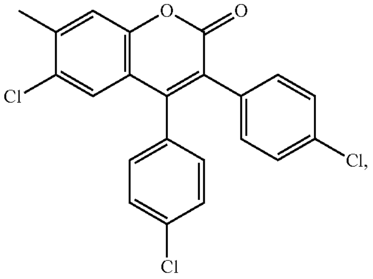
(A6)
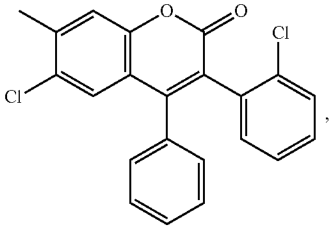
(A4)
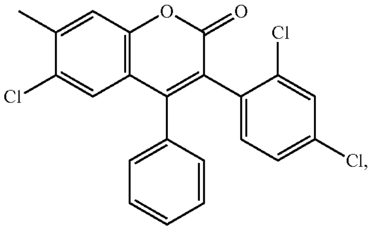
(D6)
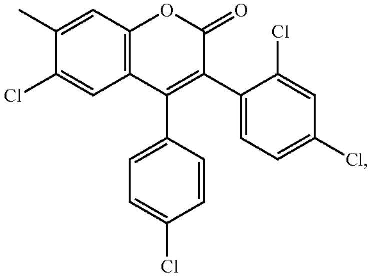
(H5)
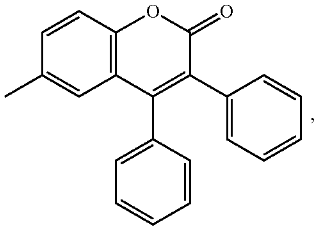
(B6)
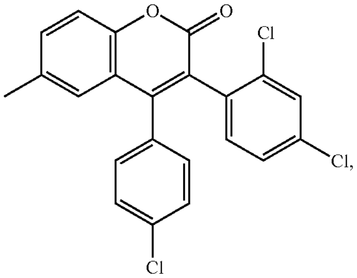

-continued
(C5)
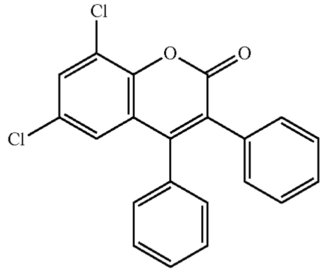
,
(F5)
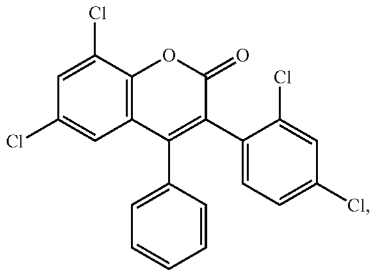
(C6)
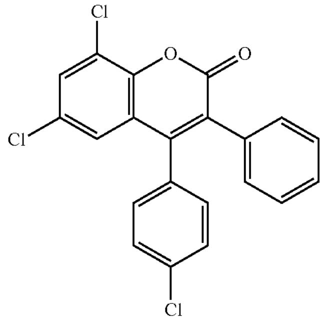
,
(D4)
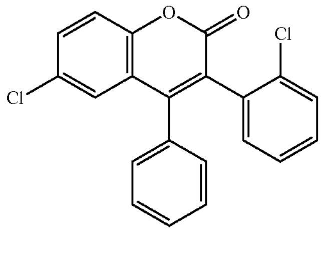
,
(B5)
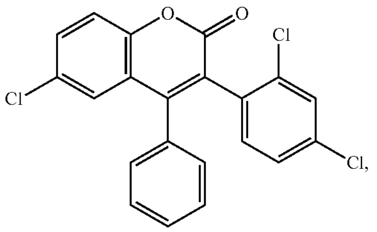
-continued
(H3)
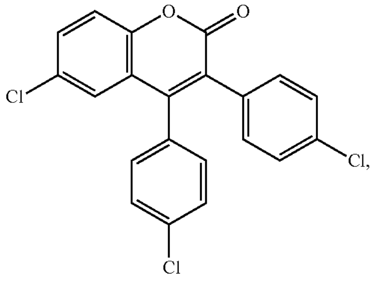
(B3)
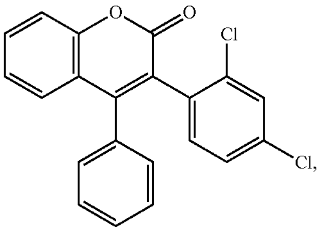
(G5)
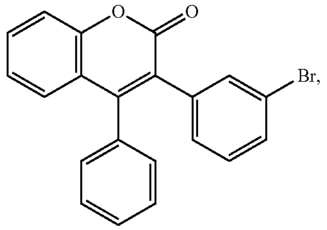
(E5)
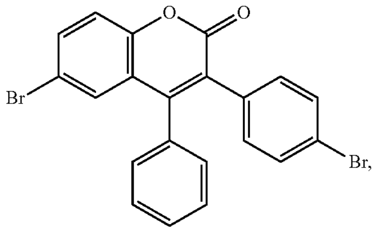
(B4)
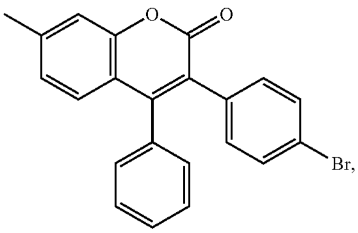
(E4)
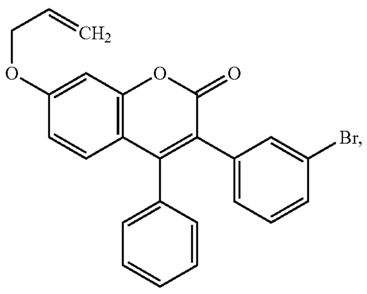

(G4)
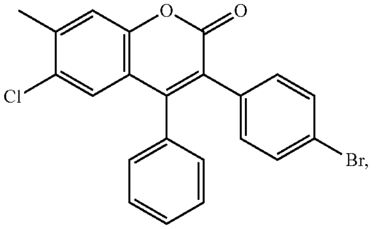
(F4)
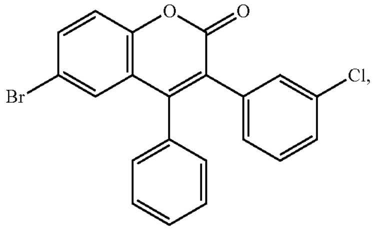
(E3)
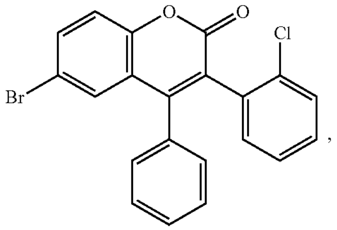
(B2)
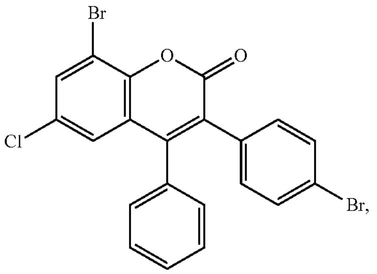
(G3)
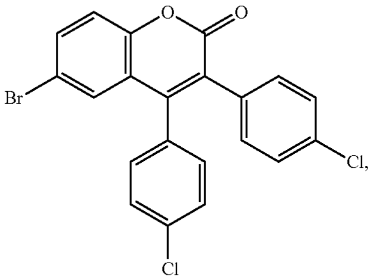
(F3)
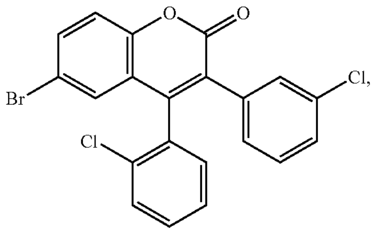
(C4)
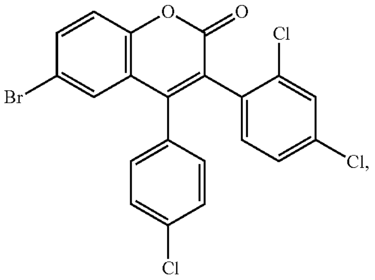
(H4)
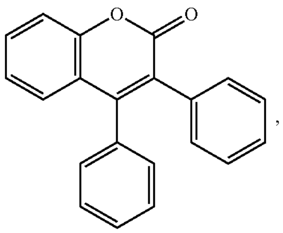
(D2)
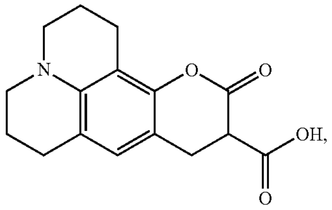
(C3)
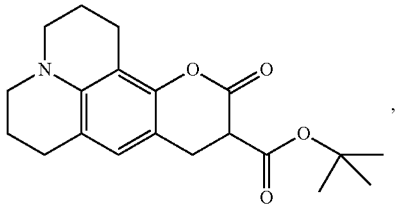
(E2)
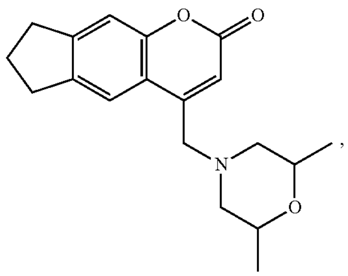
and
(E6)
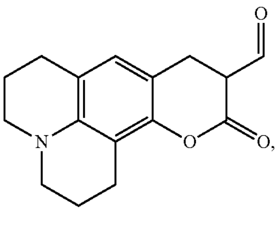
or a pharmaceutically acceptable salt thereof.

2. The method of claim 1, wherein the cells are in vivo in a mammal and the method comprises administering said compounds to said mammal.

* * * * *